(12) United States Patent
Willis et al.

(10) Patent No.: US 7,497,865 B2
(45) Date of Patent: Mar. 3, 2009

(54) METHOD AND APPARATUS FOR PERFORMING ANASTOMOSIS WITH EVERSION OF TISSUE EDGES AND JOINING OF EXPOSED INTIMA OF THE EVERTED TISSUE

(75) Inventors: Geoffrey H. Willis, Redwood City, CA (US); Thomas A. Kramer, San Carlos, CA (US); Paul A. Spence, Louisville, KY (US); George T. Christakis, Toronto (CA); Timothy J. McCoy, San Carlos, CA (US); John W. Davis, Mountain View, CA (US); Bradley D. Blackwood, San Carlos, CA (US); Peter Callas, Redwood City, CA (US); Michael Francis Wei, San Mateo, CA (US); Jonathan L. Podmore, San Francisco, CA (US); Andrew Knight, San Francisco, CA (US); Thomas J. Ward, Grandview Heights, OH (US); Warren P. Williamson, IV, Loveland, OH (US)

(73) Assignee: MAQUET Cardiovascular, LLC, San Jose, CA (US)

( * ) Notice: Subject to any disclaimer, the term of this patent is extended or adjusted under 35 U.S.C. 154(b) by 698 days.

(21) Appl. No.: 10/855,604

(22) Filed: May 26, 2004

(65) Prior Publication Data

US 2004/0220597 A1    Nov. 4, 2004

Related U.S. Application Data

(60) Division of application No. 09/654,605, filed on Sep. 1, 2000, now Pat. No. 6,811,555, and a continuation-in-part of application No. 09/641,284, filed on Aug. 17, 2000, now Pat. No. 6,565,581, and a continuation-in-part of application No. 09/200,796, filed on Nov. 27, 1998, now Pat. No. 6,254,617, which is a division of application No. 08/714,615, filed on Sep. 16, 1996, now Pat. No. 5,868,763.

(60) Provisional application No. 60/152,001, filed on Sep. 1, 1999, provisional application No. 60/150,033, filed on Aug. 20, 1999.

(51) Int. Cl.
*A61B 17/08* (2006.01)
*A61B 17/10* (2006.01)
*A61B 17/04* (2006.01)

(52) U.S. Cl. ............ 606/153; 606/142; 227/175.1

(58) Field of Classification Search ............ 606/142, 606/153, 219, 139; 227/175.1, 180.1, 181.1
See application file for complete search history.

(56) References Cited

U.S. PATENT DOCUMENTS

| | | |
|---|---|---|
| 3,155,095 A | 11/1964 | Brown |
| 3,166,072 A | 1/1965 | Sullivan, Jr. |
| 3,254,650 A | 6/1966 | Collito |
| 3,258,012 A | 6/1966 | Nakayama et al. |
| 3,606,888 A | 9/1971 | Wilkinson |
| 3,657,744 A | 4/1972 | Ersek |
| 3,683,926 A | 8/1972 | Suzuki |
| 3,774,615 A | 11/1973 | Lim et al. |
| 3,908,662 A | 9/1975 | Rasgulov et al. |
| 3,938,528 A | 2/1976 | Bucalo |
| 3,973,570 A | 8/1976 | Razgulov et al. |
| 3,974,835 A | 8/1976 | Hardy, Jr. |
| 3,993,078 A | 11/1976 | Bergentz et al. |
| 4,055,186 A | 10/1977 | Leveen |
| 4,214,586 A | 7/1980 | Maricle |
| 4,214,587 A | 7/1980 | Sakura, Jr. |
| 4,233,981 A | 11/1980 | Schomacher |
| 4,345,600 A | 8/1982 | Rothfuss |
| 4,368,736 A | 1/1983 | Kaster |
| 4,474,181 A | 10/1984 | Schenck |
| 4,523,592 A | 6/1985 | Daniel |
| 4,587,202 A | 5/1986 | Borysko |
| 4,657,019 A | 4/1987 | Walsh et al. |
| 4,676,245 A | 6/1987 | Fukuda |
| 4,681,110 A | 7/1987 | Wiktor |
| 4,747,407 A | 5/1988 | Liu et al. |
| 4,777,096 A | 10/1988 | Borysko |
| 4,787,386 A | 11/1988 | Walsh et al. |

| | | | |
|---|---|---|---|
| 4,872,874 A | 10/1989 | Taheri | |
| 4,873,975 A | 10/1989 | Walsh et al. | |
| 4,899,744 A | 2/1990 | Fujitsuka et al. | |
| 4,930,502 A | 6/1990 | Chen | |
| 4,930,674 A | 6/1990 | Barak | |
| 4,950,283 A | 8/1990 | Dzubow et al. | |
| 4,957,499 A | 9/1990 | Lipatov et al. | |
| 4,979,954 A | 12/1990 | Gwathmey et al. | |
| 4,997,439 A | 3/1991 | Chen | |
| 5,035,702 A | 7/1991 | Taheri | |
| 5,037,428 A | 8/1991 | Picha et al. | |
| 5,057,401 A | 10/1991 | Borysko et al. | |
| 5,078,735 A | 1/1992 | Mobin-Uddin | |
| 5,089,008 A | 2/1992 | Chen | |
| 5,123,908 A | 6/1992 | Chen | |
| 5,188,638 A | 2/1993 | Tzakis | |
| 5,234,447 A | 8/1993 | Kaster et al. | |
| 5,250,057 A | 10/1993 | Chen | |
| 5,263,973 A | 11/1993 | Cook | |
| 5,336,233 A | 8/1994 | Chen | |
| 5,346,501 A | 9/1994 | Regula et al. | |
| 5,366,462 A | 11/1994 | Kaster et al. | |
| 5,403,333 A | 4/1995 | Kaster et al. | |
| 5,456,714 A | 10/1995 | Owen | |
| 5,486,187 A | 1/1996 | Schenck | |
| 5,501,689 A | 3/1996 | Green et al. | |
| 5,562,690 A | 10/1996 | Green et al. | |
| 5,653,743 A | 8/1997 | Martin | |
| 5,669,918 A * | 9/1997 | Balazs et al. | 606/153 |
| 5,683,453 A | 11/1997 | Palmaz | |
| 5,693,454 A | 12/1997 | Munoz | |
| 5,695,504 A | 12/1997 | Gifford, III et al. | |
| 5,702,048 A | 12/1997 | Eberlin | |
| 5,707,380 A | 1/1998 | Hinchliffe et al. | |
| 5,741,274 A | 4/1998 | Lenker et al. | |
| 5,752,966 A | 5/1998 | Chang | |
| 5,762,811 A | 6/1998 | Munoz | |
| 5,792,180 A | 8/1998 | Munoz | |
| 5,868,763 A | 2/1999 | Spence et al. | |
| 5,879,371 A | 3/1999 | Gardiner et al. | |
| 5,904,697 A | 5/1999 | Gifford, III et al. | |
| 5,938,696 A | 8/1999 | Goicoechea et al. | |
| 5,957,973 A | 9/1999 | Quiachon et al. | |
| 5,976,159 A | 11/1999 | Bolduc et al. | |
| 5,976,178 A | 11/1999 | Goldsteen et al. | |
| 6,030,392 A | 2/2000 | Dakov | |
| 6,036,703 A | 3/2000 | Evans et al. | |
| 6,068,637 A | 5/2000 | Popov et al. | |
| 6,152,937 A | 11/2000 | Peterson et al. | |
| 6,176,413 B1 | 1/2001 | Heck et al. | |
| 6,179,849 B1 | 1/2001 | Yencho et al. | |
| 6,241,742 B1 * | 6/2001 | Spence et al. | 606/153 |
| 6,428,550 B1 * | 8/2002 | Vargas et al. | 606/153 |

FOREIGN PATENT DOCUMENTS

| | | |
|---|---|---|
| DE | 2822 603 A1 | 11/1979 |
| DE | 29713335 U1 | 11/1997 |
| EP | 0 539 237 A1 | 10/1992 |
| GB | 1181563 | 2/1967 |
| WO | WO 95/17127 | 6/1995 |
| WO | WO 95/17128 | 6/1995 |
| WO | WO 95/35065 | 12/1995 |
| WO | WO 98/02099 | 1/1998 |
| WO | WO 98/19630 | 5/1998 |
| WO | WO 99/21491 | 5/1999 |

OTHER PUBLICATIONS

C.A.F. Tulleken et al., "End-to-End Anastomosis of Small Vessels Using an ND:YAG Laser with a Hemispherical Contract Probe," Technical Note, *Journal of Neurosurgery*, vol. 76, Mar. 1992, pp. 546-549.

Robin H. Heijmen et al., A Novel One-Shot Anastomotic Stapler Prototype for Coronary Bypass Grafting on the Beating Heart: Feasbility in the Pig, *The Journal of Thoracic and Cardiovascular Surgery*, Jan. 1999, pp. 117-125.

* cited by examiner

*Primary Examiner*—Julian W Woo
(74) *Attorney, Agent, or Firm*—Law Office of Alan W. Cannon

(57) ABSTRACT

A ring for use in anastomosis. Preferably, the ring is integrally formed from metal, and includes a ring portion and tines and docking members that extend from the ring portion. The ring portion and tines are malleable, and preferably also the docking members are malleable. The ring portion and tines are malleable in the sense that once deformed from a first shape into a second shape, they will not relax back into the first shape from the second. To install the ring in a vessel with the ring portion extending around an incision or other orifice, the tines pierce the tissue around the orifice and are curled against an anvil. The action of curling the tines inverts the tissue near the orifice edges to expose the inside surface of the vessel or organ. Other aspects of the invention are a method and apparatus for installing an anastomosis ring in an incision or other orifice in a vessel or other organ, a method and apparatus for precisely aligning two anastomosis rings (each installed in an incision or other orifice of a different organ) and fastening the aligned rings together. The clips can be crimped onto the aligned rings, or they can be spring clips which are sprung onto the aligned rings to clamp the rings together by spring force. Also within the scope of the invention are crimping and spring clips for use in listening together two aligned anastomosis rings. In other embodiments, the invention is a method for performing an anastomosis by installing an anastomosis ring in an orifice in an organ, installing another anastomosis ring in an orifice in another organ, precisely aligning the two installed anastomosis rings, and fastening the aligned rings together.

13 Claims, 40 Drawing Sheets

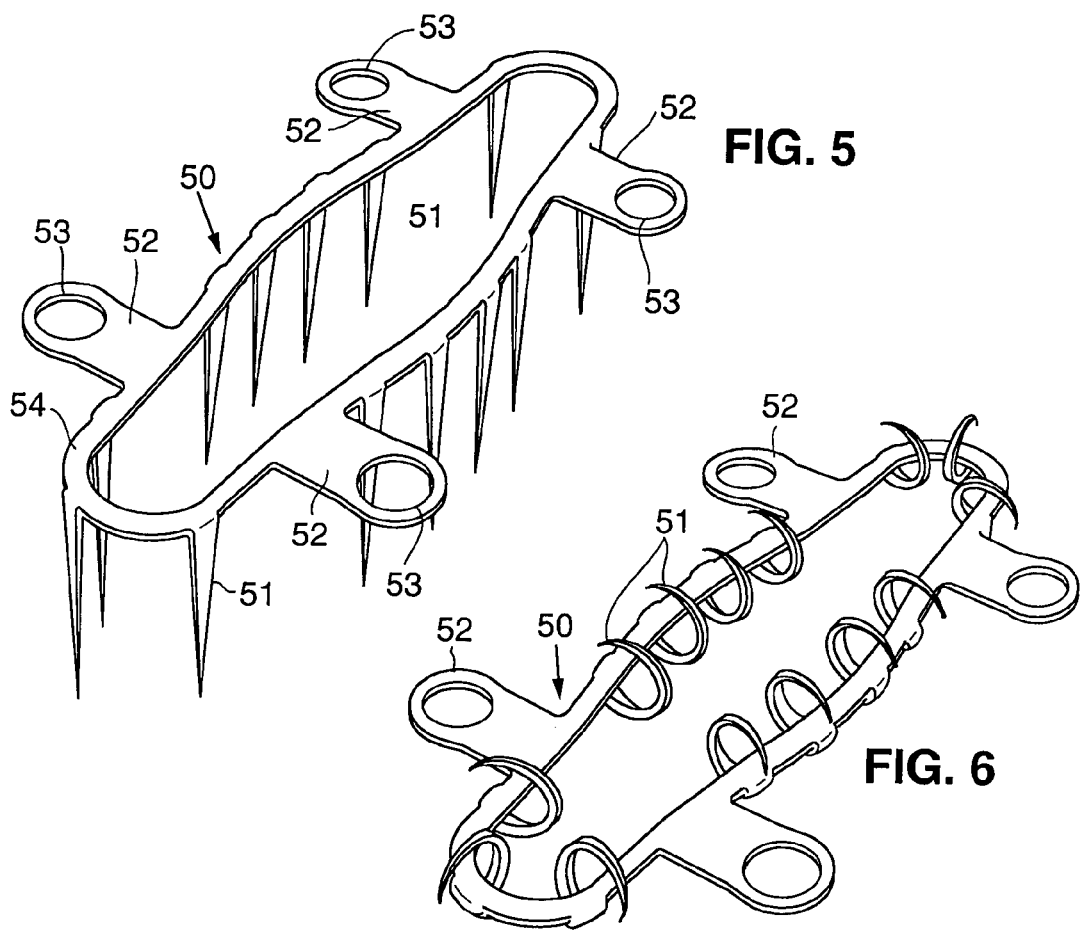
FIG. 5
FIG. 6
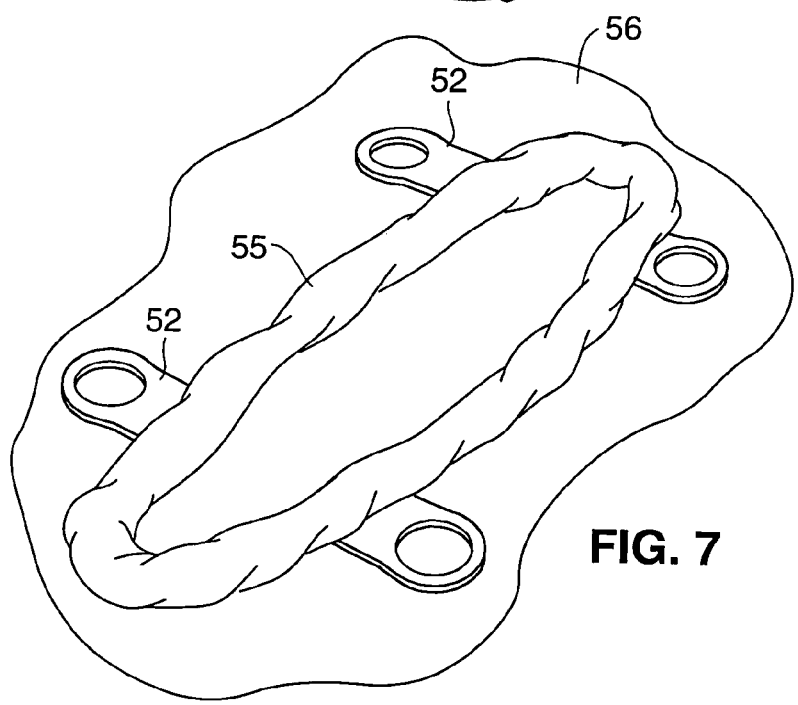
FIG. 7

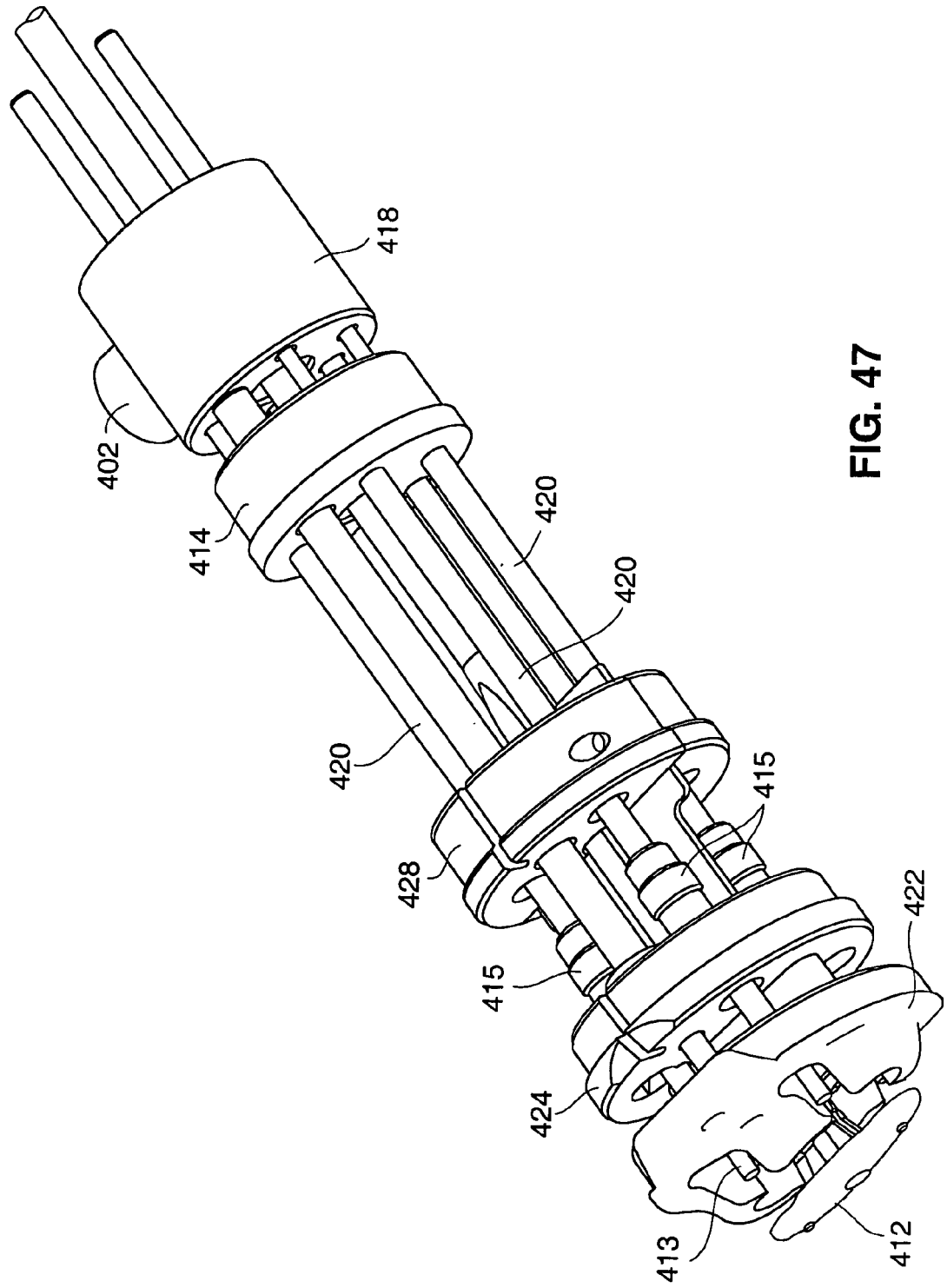

METHOD AND APPARATUS FOR PERFORMING ANASTOMOSIS WITH EVERSION OF TISSUE EDGES AND JOINING OF EXPOSED INTIMA OF THE EVERTED TISSUE

This application is a divisional of application Ser. No. 09/654,605, filed on Sep. 1, 2000, now U.S. Pat. No. 6,811,555, which claims the benefit of U.S. Provisional Application No. 60/152,001, filed on Sep. 1, 1999, and is a continuation-in-part of U.S. patent application Ser. No. 09/641,284 filed on Aug. 17, 2000, now U.S. Pat. No. 6,565,581, which in turn claims the benefit of U.S. Provisional Application No. 60/150,033, filed on Aug. 20, 1999, and is a continuation-in-part of U.S. patent application Ser. No. 09/200,796, filed on Nov. 27, 1998, now U.S. Pat. No. 6,254,617, which is a divisional of U.S. patent application Ser. No. 08/714,615, filed on Sep. 16, 1996, now U.S. Pat. No. 5,868,763. Each of U.S. application Ser. Nos. 09/654,605; 60/152,001; 09/641,284; 60/150,033; 09/200,796; and 08/714,615; and U.S. Pat. Nos. 6,811,555; 6,565,581; 6,254,617; and 5,868,763 are hereby incorporated herein in their entireties, by reference thereto, and to which application we claim priority under 35 U.S.C. §§ 119 and 120, respectively.

TECHNICAL FIELD OF THE INVENTION

The present invention relates to the art of surgery. More specifically, it relates to the field of apparatus and methods for performing anastomosis without hand-suturing.

BACKGROUND OF THE INVENTION

In the United States, many coronary artery bypass graft (CABG) procedures performed on patients annually. Each of these procedures may include one or more graft vessels which are hand sutured. Until recently, coronary artery bypass procedures have been performed with the patients on cardiopulmonary bypass while the heart is stopped with cardioplegia and the surgery is performed on an exposed, stationary heart.

The vast majority of CABG procedures performed currently are accomplished by opening the chest wall to gain access to the coronary vessels. Through the use of heart lung bypass machines and a drug to protect the heart muscle, the heart is stopped and remains still during the procedure. In this setting, the surgeon has ample time and access to the vessels to manipulate hand suturing instruments such as forceps, needle holders and retractors.

However, with increasing costs of hospital stays and increased awareness by patients of other minimally invasive surgical procedures interest in developing a minimally invasive CABG procedure is increasing hospitals need to reduce costs of procedures and patients would like less post-operative pain and speedier recovery times.

With an increased incentive to reduce costs, there is a renewed interest in redesigning cardiothoracic procedures. A few pioneering surgeons are now performing minimally invasive procedures whereby the coronary artery bypass is performed through a small incision in the chest wall. There are some surgeons that believe that the best way to perform a minimally invasive coronary artery bypass procedure is to perform the procedure on a beating heart, i.e., without heart-lung bypass and cardioplegia. This minimizes the time it takes to perform the procedure and reduces the cost of the operation by eliminating the heart lung bypass machine.

In the case of minimally invasive procedures on a beating heart, the surgeon starts by making a mini-thoracotomy between the fourth and fifth ribs and, sometimes, removing the sternal cartilage between the fourth or fifth rib and the sternum. The space between the fourth and fifth ribs is then spread to gain access to the internal mammary artery (IMA) which is dissected from the wall of the chest. After dissection, it is used as the blood supply graft to the left anterior descending artery of the heart (LAD). Below the IMA lies the pericardium and the heart. The pericardium is opened exposing the heart. At this point, the LAD may be dissected from the fissure of the heart and suspended up with soft ligatures to isolate the artery from the beating heart.

Typically, a special retractor gently applies pressure to the heart muscle to damp movement at the LAD. A small arteriotomy is performed in the LAD and the graft IMA is sutured to the LAD.

Traditionally, to gain access to the cardiac vessels to perform this procedure the sternum is sewn in half and the chest wall is separated. Although this procedure is well perfected the patient suffers intense pain and a long recovery.

Until recently all bypass graft procedures have been performed by hand suturing the tiny vessels together with extremely fine sutures under magnification. The skills and instruments required to sew extremely thin fragile vessel walls together have been perfected over the last twenty years and are well known to the surgical community that performs these procedures.

FIG. 1 shows a conventional anastomosis using hand-sutures, in which coronary artery 10 and graft vessel 12 are connected in side-to-side fashion One end (13) of vessel 12 is tied closed, and the side wall of vessel 12 near this closed end is to be attached to artery 10. The opposite end of vessel 12 (not shown) is to be attached to an aorta or IMA. In typical cardiopulmonary bypass procedures, one end of a graft vessel is grafted to a coronary artery (at a "distal" graft site) and the other end of the graft vessel is grafted to the aorta (at a "proximal" graft site). FIG. 1 shows a distal graft site. An incision 14 is made in artery 10 and a corresponding incision 16 is made in graft 12. The surgeon aligns the incisions and hand-sutures the aligned edges of the incisions together using sutures 18 and 20. Hand-suturing can also be used to perform an end-to-side anastomosis, in which an open end of the graft vessel is aligned with an incision in the sidewall of another vessel (e.g., an aorta) and the aligned tissue is hand-sutured together. The present invention can be used to perform either end-to-side or side-to-side anastomosis without hand-suturing.

There is a need (which is addressed by the present invention) for methods and apparatus useful for performing anastomosis during CABG surgery on a beating heart. When performing anastomosis during such surgery on a beating heart, use of hand-suturing to attach the graft vessel is very imprecise due to the translation of movement from the beating heart to the suspended artery. This motion may cause imprecise placement of the suture needles. Any imprecise placement of the sutures may cause a distortion of the anastomosis which may cause stenosis at this junction. The sutures used for this procedure are extremely fine (0.001" in diameter) and are placed less than 1 mm apart.

As one can imagine it is difficult enough to place suture needles the size of a small eyelash into a vessel wall with placement accuracy of better than 1 mm. To accomplish this feat of precision on a moving target is extremely difficult. To make matters worse, the site is often bloody due to the fact that the heart has not been stopped. During beating heart surgery, the surgeon can attempt to minimize the deleterious effects of the beating heart motion by using suspension or retraction techniques, but it is impossible to isolate all such movement (and attempts to minimize the motion can damage the vessel being restrained or cause myocardial injury). Even when performing anastomosis in an 'open chest' surgical setting in which the surgeon has adequate access and vision of the surgical site to manipulate the anatomy and instruments, it is difficult to perform the hand-suturing required in traditional methods. When performing anastomosis in a minimally invasive procedure access to (and vision of) the site is more limited and the hand-suturing is more difficult.

If the sutures are not placed correctly in the vessel walls, bunching or leaks will occur. During a minimally invasive procedure this is disastrous, usually resulting in the conversion to an open chest procedure to correct the mistake. Any rough handling of the vessel walls is detrimental as inflammation can cause further postoperative complications.

An anastomosis must seal without leaking to prevent exsanguination. Therefore, any anastomosis technique which does not require hand sutures must provide a leak free seal in a very confined space, while providing proper flow area in the vessel after healing is complete.

Although minimally invasive CABG procedures are taking place now with hand-sutured anastomosis they require superlative surgical skills and are therefore not widely practiced. There is a need for methods and apparatus which permit the forming of a precise anastomosis without requiring the stopping of a beating heart, during either minimally invasive or open chest surgery, and without requiring hand suturing.

Several techniques have been proposed for performing anastomosis of blood vessels. However, the prior art techniques often require the vessels to be severely deformed during the procedure. The deformation may be required to fit the vessels together or to fit a vessel to an anchoring device.

For example, some prior art anastomosis techniques have used rigid rings to join two vessels together. In one such technique (indicated by FIG. 2), rigid ring 30' is positioned around the edges of an incision in the sidewall of artery 31 in a manner that inverts the tissue near the incised edges (by everting the tissue) to expose the inside lining (intima) of the vessel walls. The incised edges can be anchored on a flange (not shown) on ring 30'. Rigid ring 30" is positioned around the open end of graft vessel 31 in a manner that inverts the tissue at the open end (by everting the tissue), thereby exposing the intima of vessel 31. Then, rings 30' and 30" are moved into alignment with each other and fastened together (e.g., by a clamp) so that the intima of the vessels are clamped together in contact with each other.

In another such technique (indicated by FIG. 3), rigid ring 30 is positioned around the open end of vessel 33 in a manner that inverts the tissue at the open end (by everting the tissue), thereby exposing the intima of vessel 33. Then, the open end of vessel 34 is fitted over (and fastened to) the ring-containing end of vessel 33.

However, it may be undesirable to simply slit side-wall tissue of a vessel and pull the incised edges through a ring (as in FIG. 2) to anchor them on a flange (or to invert and pull tissue at the end of a vessel over a ring as in FIG. 3). Pulling or stretching the vessel walls can produce an unpleasant and unexpected result. Vessel walls are made of tissue fibers that run in the radial direction in one layer and the longitudinal direction in another layer. In addition the elasticity of the tissue fibers in the longitudinal direction is greater than those that run radially. Therefore, the tissue will not stretch as easily in the radial or circumferential direction and results in a narrowing or restriction when pulled or stretched in the prior art devices. Vessel walls also have a layer of smooth muscle cells that can spasm if treated harshly. Such manhandling will result in restrictions and stenotic junctions because the vessel walls will react poorly to being treated in such a rough manner and the stretching of the vessel wall will telegraph up the vessel wall due to the high radial stiffness of the vessel structure, causing restrictions and spasms in the vessel wall.

Additionally, prior art methods and apparatus for anastomosis without hand-suturing do not adequately ensure hemostasis to avoid leakage from the anastomosis junction under pressure, and they attempt to accomplish hemostasis through excessive clamping forces between clamping surfaces or stretching over over-sized fittings.

In order to effect good healing, healthy vessel walls must be brought into intimate approximation. This intimate approximation can be accomplished by the skilled hands of a surgeon with sutures. A vascular surgeon is taught how to suture by bringing the vessel edges together with just the right knot tightness. If the edges are tied too loosely, the wound will leak and have trouble healing causing excessive scar tissue to form. If the edges are tied too tightly, the sutures will tear through the delicate tissue at the suture hole causing leaks. The key is to bring the edges together with just the right amount of intimate approximation without excessive compression.

Conventional junctions that include rings are anatomically incorrect both for blood flow and for healing. A well made anastomotic junction is not made in a single plane and should accurately follow blood vessel geometry. The junction is more of a saddle shape, and the cross section is not necessarily a circle. The junction where the vessel units join is not a constant cross section angle, but an angle that varies continuously throughout with respect to any linear reference. In addition, the length of the junction should be many times the width of the opening in order to assure a low blood flow pressure gradient in the junction and to assure a proper flow area. In fact, the best results are obtained if the confluence area is actually oversized. The prior art junctions do not account for such flow characteristics and parameters and are thus deficient. There is a need for an anastomotic technique which can establish proper flow characteristics and parameters and that accurately preserves blood vessel geometry, specifically the plural planar nature in which the junction occurs. Furthermore, most anastomoses are made between vessels that are not similar in size. It is therefore necessary to provide a means and method which allow for the accommodation and joining of dissimilarly sized vessels.

After attachment of a graft vessel by anastomosis, the supply vessels grow in diameter to accommodate their new role in providing oxygenated blood to the heart. Therefore, there is a need to provide a junction that will accommodate any increase in the dimension of the graft vessel size. With a rigid ring that is a singular circular cross section of the graft, the fitting does not allow the vessel to provide this increase in flow as the vessels expand to meet the needs of the heart muscle. Still further, the inside lining of the vessel walls (intima) should make contact with each other (for a variety of reasons). The walls of the joined vessels must come together with just the right amount of approximation to promote good healing and prevent leakage and formation of false lumens. If the incised edges are too far apart scarring will occur causing restrictions. The walls cannot be compressed tightly between two hard surfaces which will damage the vessels. The prior art teaches plumbing-like fittings clamped onto vascular structures. However, clamping and compressing the vessel walls too tightly will cause necrosis of the vessel between the clamps. If necrosis occurs the dead tissue will become weak and most likely cause a failure of the joint. Still further Such rings and tubes used to clamp vessels together do not follow the correct anatomical contours to create an unrestricted anastomosis. Failing to account for the way healing of this type of junction occurs, and not accounting for the actual situation may cause a poor result.

A suture technique has the advantage of having the surgeon making on-the-fly decisions to add an extra suture if needed to stop a leak in the anastomosis. In a mechanical minimally invasive system it will not be possible to put in an 'extra suture throw' so the system must provide a way to assure complete hemostasis. Approximation using a mechanical system will not be perfect. If the design errs on the side of not overcompressing the tissue, there may be very small areas that may present a leak between the edges of the vessel walls. Healing with prior art techniques using mechanical joining means is not as efficient as it could be. There is a need for an anastomotic technique that accounts for the way healing actually occurs and provides proper structural support during the healing process.

Many times when a CABG operation is undertaken, the patient has multiple clogged arteries. At the present time, the average number of grafts is 3.5 per operation. When multiple grafts are performed, there is sometimes the opportunity to use an existing or newly added supply vessel or conduit for more than one bypass graft. This is known as a jump graft, whereby the conduit, at the distal end thereof is terminated in a side-to-side anastomosis first, with an additional length of conduit left beyond the first junction. Then, an end of the conduit is terminated in an end-to-end junction. This saves time and resources and may be necessary if only short sections or a limited amount of host graft material is available.

Conventional means and methods of performing an anastomosis do not permit the formation of multiple anastomotic sites on a single graft vessel such as at both proximal and distal ends. Thus a surgeon will have to use multiple tools to perform multiple anastomoses. This will be either impossible or very expensive. Therefore, there is a need for a means and a method for performing an anastomosis which will lend itself to efficient and cost-effective multiple by-pass techniques.

There is also a need for a means and method for performing an anastomosis which will lend itself to efficient and cost-effective jump graft techniques.

As noted above, performing anastomosis in a minimally invasive manner while the patient's heart is beating requires an extremely high degree of dexterity. Any apparatus used in such a procedure must therefore be as easy and efficient to use as possible so that a surgeon can focus most of his or her attention on the anastomosis site.

Further, any apparatus used for anastomosis without hand-suturing should be amenable to efficient manufacture.

U.S. Pat. No. 5,868,763, issued Feb. 9, 1999, teaches methods and apparatus for accomplishing anastomosis without hand-suturing in a manner overcoming many of the disadvantages of conventional anastomosis methods and apparatus such as those described above. The apparatus of U.S. Pat. No. 5,868,763 includes a flexible "cuff" having tines configured to pierce a vessel or other organ (e.g., to penetrate tissue around the edges of an incision in the side-wall of a blood vessel) to attach the cuff to the vessel or organ. When deformed, the cuff remains in the deformed configuration until physically moved into another configuration. The cuff can be mounted to a vessel (or other organ) around an incision, and then deformed to open or close the incision as desired.

When implementing side-to-side anastomosis (to attach the side wall of one vessel to the side wall of another vessel), one cuff is attached around an incision in the side wall of the first vessel and another cuff is typically attached around an incision in the side wall of the other vessel. The cuffs are then aligned and fastened together. However, the cuffs are designed (and attached to the vessels) such that when the two cuffs are aligned, the incised tissue edges of the two vessels are placed in edge-to-edge contact (so that there is a risk that the anastomosis will be completed without the intima of the two vessels being in direct contact with each other at all locations where the vessels meet each other).

In embodiments in which a single cuff is used to implement side-to-side anastomosis, the cuff is attached (by a first set of times) around an incision in the side wall of one vessel, the cuff is aligned with an incision in the side wall of a second vessel, and the cuff is attached to the second vessel (by a second set of times extending around the second vessel). However, the cuff is designed (and attached to the first vessel) such that when the cuff is aligned with the second vessel, the incised tissue edges of the two vessels are placed in edge-to-edge contact (so that there is a risk that the anastomosis will be completed without achieving direct intima-to-intima contact at all locations where the vessels meet each other).

FIG. 4 shows a side-to-side anastomosis which connects vessel 10 to vessel 12, as implemented by two cuffs 40 and 45 of the type described in U.S. Pat. No. 5,868,763. Cuff 40 has an oval shaped (the oval extending in a horizontal plane perpendicular to the plane of FIG. 4), flexible metal body 41 having tines 42. Sheet 98 (which is preferably made of woven fabric suitable for use in surgery) is attached to the metal body. A generally oval opening extends through metal body 41 and sheet 98, so that cuff 40 can be attached around an incision in vessel 10 with the opening providing access to the incision.

Similarly, cuff 45 has an oval shaped, flexible metal body 43 having tines 44. Sheet 99 (preferably made of woven fabric suitable for use in surgery) is attached to metal body 43. A generally oval opening extends through body 43 and sheet 99, so that cuff 45 can be attached around an incision in the side wall of vessel 12 with the opening providing access to the incision.

To perform the anastomosis shown in FIG. 4, an anvil (not shown) is inserted through an incision in artery 10, and cuff 40 (with each of the tines 42 in a straight configuration) is positioned in the incision with the sharp tips of tines 42 engaging the tissue surrounding the incision. An installing instrument (not shown) is then operated to force the tines 42 against the anvil, thus causing the tines 42 to penetrate through the tissue into contact with the anvil and to bend into the bent configuration shown in FIG. 4 (so as to attach cuff 40 to the tissue of artery 10 surrounding the incision). An anvil (not shown) is also inserted through an incision in artery 12, and cuff 45 (with each of the tines 44 in a straight configuration) is positioned in the incision with the sharp tips of tines 44 engaging the tissue surrounding the incision. A cuff-installing instrument (not shown) is then operated to force tines 44 against the anvil, thus causing tines 44 to penetrate through the tissue into contact with the anvil and to bend into the bent configuration shown in FIG. 4 (so as to attach cuff 45 to the tissue of artery 12 surrounding the incision). Then, cuff 40 is aligned with cuff 45, and body 98 of cuff 40 is attached to body 99 of cuff 45 by fasteners 114 (as shown in FIG. 4).

When cuffs 40 and 45 are so aligned, the incised tissue edges of vessels 10 and 12 are placed in edge-to-edge contact at locations "A." There is some risk that the intima of vessels 10 and 12 (the very thin tissue layer lining the inner diameter of each vessel) may not be placed in direct contact with each other at all locations where the vessels meet each other. For example, there may be a gap where the central portion of one incised tissue edge (rather than the thin intima at the inner end of the edge) comes into direct contact with the central portion of the other incised tissue edge. Since the intima tissue provides lubricity and a low friction surface against which blood can flow, failure to accomplish uniform intima-to-intima contact between the two vessels has several disadvantages, including the following: blood flowing from one joined vessel to the other may encounter a "gap" in the intima layer to which it is exposed (a hole in an otherwise continuous intima layer at which intima tissue is missing) so that the blood comes into direct contact with the tissue that is normally shielded from the blood by intima tissue. If this occurs, the flowing blood can create a false lumen by separating tissue layers of one or both of the vessels, or the flowing blood can otherwise cause damage at the anastomosis site which hinders healing or results in leakage.

In addition to achieving the noted advantages of direct intima-to-intima contact (relative to "incised edge"-to-"incised edge" contact as in FIG. 4), the present invention also allows the elimination of hemostatic media (e.g., bodies 98 and 99) from rings which are employed to facilitate anastomosis. Thus, in contrast with the FIG. 4 apparatus (in which fabric bodies 98 and 99 line the outer sidewalls of the joined vessels 10 and 12), the invention facilitates anastomosis with direct intima-to-intima contact, without hand-suturing, and without provision of hemostatic media for pressing against the joined vessels at the anastomosis site.

The present invention, like the apparatus disclosed in U.S. Pat. No. 5,868,763, can be used to perform end-to-end anastomosis (in which the open end of one vessel is attached to the open end of another vessel, for example, with vessel geometry as in FIG. 3) or end-to-side anastomosis (in which the open end of one vessel is attached in fluid communication with an incision in the side wall of another vessel), as well as side-to-side anastomosis (with vessel geometry as in FIGS. 1 and 4). However, unlike the apparatus disclosed in U.S. Pat. No. 5,868,763, the apparatus of the present invention allows direct and uniform intima-to-intima contact to be achieved in all three cases.

SUMMARY OF THE INVENTION

In a class of preferred embodiments, the invention is a ring (for use in anastomosis) that is integrally formed from metal, and includes a ring portion and tines and docking arms that extend from the ring portion. The ring portion and tines are malleable, and preferably also the docking arms are flexible. The ring portion and tines are malleable in the sense that once deformed from a first shape into a second shape., they will not relax back into the first shape from the second. In some preferred embodiments, the flexible docking arms are elastic and in other preferred embodiments they are malleable (the term "flexible" is used in a broad sense encompassing both the narrower terms "malleable" and "elastic"). The ring is designed for use without a fabric body (or other hemostatic media) being attached thereto.

To install the ring in a vessel (or other organ) with the ring portion extending around an incision (or other orifice), the tines pierce the tissue around the orifice and are curled against an anvil. The action of curling the tines inverts the tissue near the orifice edges (by everting such tissue) to expose the inside surface of the organ (so that such exposed inside surface can be joined to tissue of another vessel or organ). In typical use, the ring is installed with the ring portion extending around an incision in the side wall of a blood vessel, and the action of curling the tines everts the incised edges of the orifice to expose the inside lining (intima) of the blood vessel.

In variations, the ring has a malleable ring portion and tines (and docking arms that can but need not be flexible), but the ring is not integrally formed from metal. In some variations, it is assembled from component parts which are connected together (e.g., by welding). In other variations, it is made of material other than metal, but which has the required mechanical properties.

In other embodiments, the invention is a method and apparatus for installing an anastomosis ring in an incision (or other orifice) in a vessel or other organ. In other embodiments, the invention is a method and apparatus for precisely aligning two anastomosis rings, each installed in an incision (or other orifice) of a different vessel or other organ, and fastening the aligned rings together. The clips can be crimped onto the aligned rings, or they can be spring clips which are sprung onto the aligned rings to clamp the rings together by spring force. Also within the scope of the invention are a variety of crimping and spring clips for use in fastening together two aligned anastomosis rings.

In other embodiments, the invention is a method for performing an anastomosis, including the steps of installing an anastomosis ring in an incision (or other orifice) in a vessel or other organ, installing another anastomosis ring in an incision (or other orifice) in another vessel or other organ, precisely aligning the two installed anastomosis rings, and fastening the aligned rings together (by crimping fasteners on them or clamping them together using spring clips).

BRIEF DESCRIPTION OF THE DRAWING FIGURES

FIG. 5 is a perspective view of an embodiment of the inventive ring for use in performing anastomosis without hand sutures (with its tines in their initial, straight configuration).

FIG. 6 is a perspective view of the ring of FIG. 5, after its tines have been curled into their bent configuration.

FIG. 7 is a perspective view of the ring of FIG. 6, showing the manner in which the action of curling the tines everts the tissue (near the edges of an incision in the side wall of a blood vessel) to expose the inside lining (intima) of the vessel walls, during attachment of the ring to the vessel.

Figure 25:
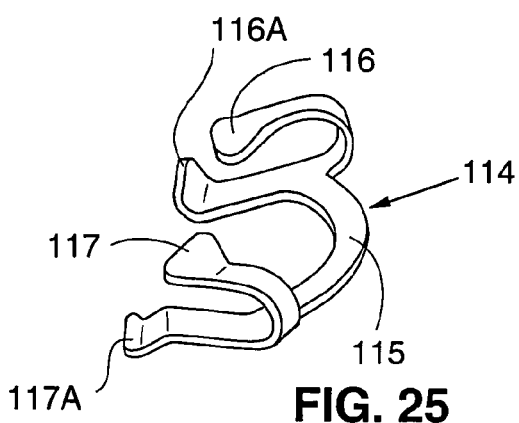
FIG. 25 is a perspective view of another type of fastener clip which can be crimped around aligned docking features of two of the inventive rings.
Figure 25A:
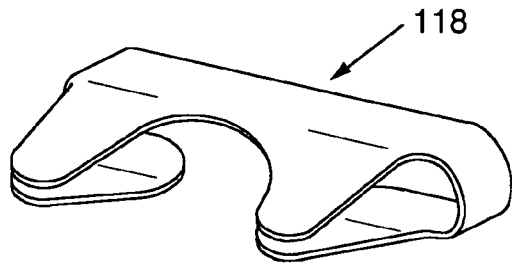
FIG. 25A is a perspective view of another type of fastener clip (having spring arms) which can be crimped around aligned docking features of two of the inventive rings.
Figure 25B:
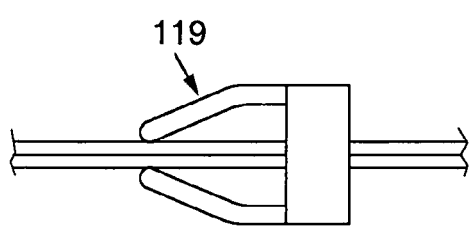
FIG. 25B is a side view of another type of fastener clip (in a non-crimped configuration) which can be crimped around aligned docking features of two of the inventive rings.
Figure 25C:
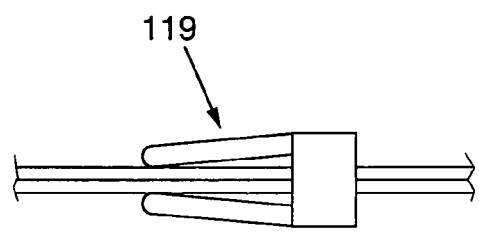
FIG. 25C is a side view of the FIG. 25B clip, after it has been crimped.
Figure 25D:
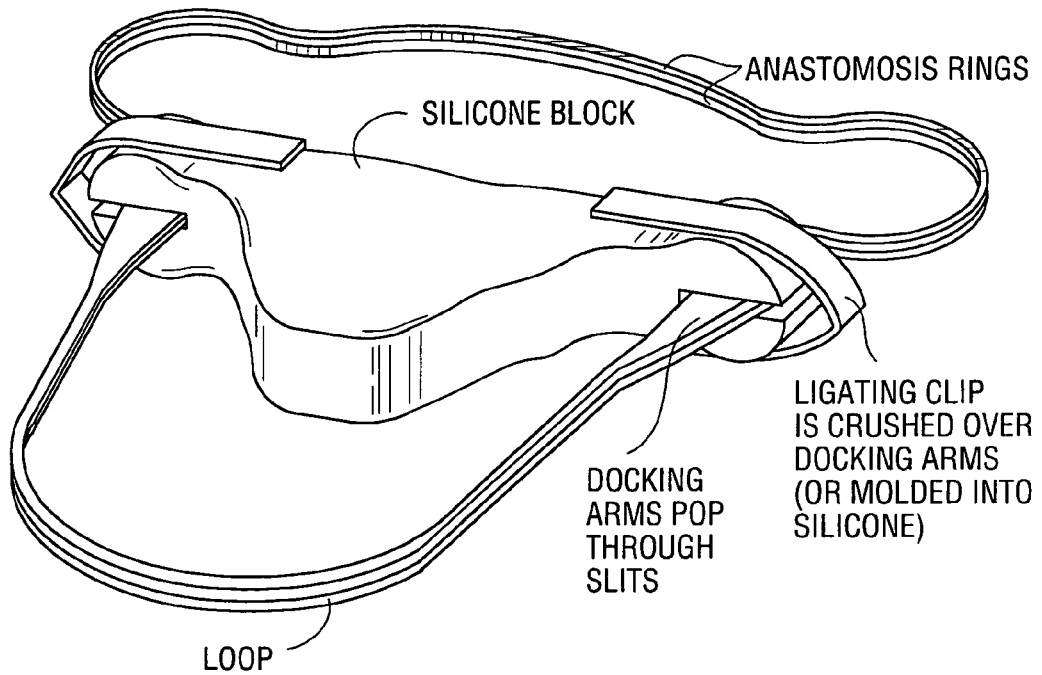
FIG. 25D is a perspective view of another type of fastener clip (shaped like a ligating clip, and having silicone between its end portions) which can be crimped around aligned docking features of two of the inventive rings.
Figure 25E:
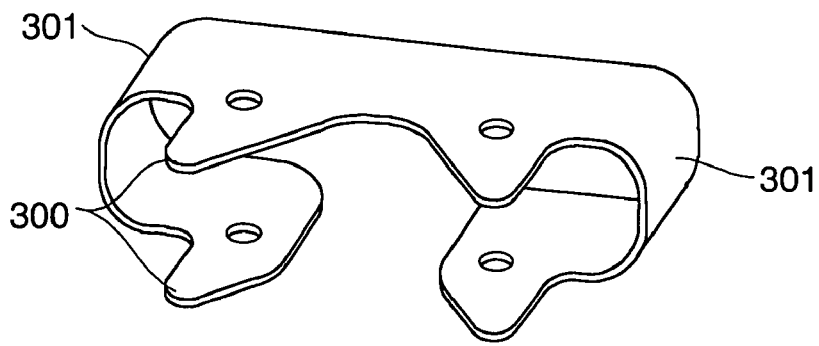
Figure 25F:
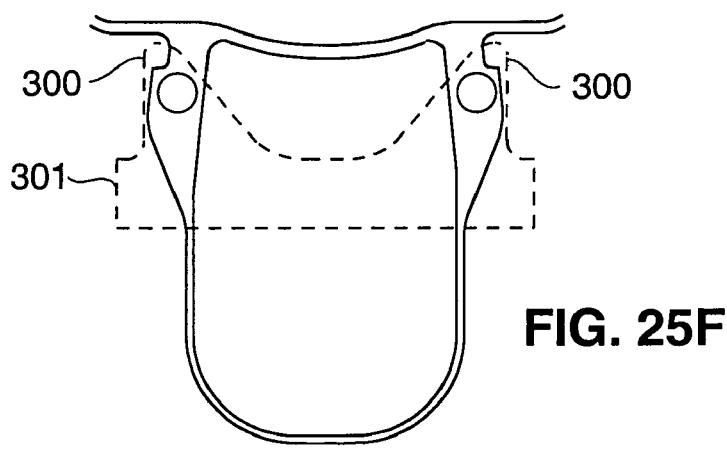

FIG. 25E is a perspective view of another type of fastener clip, which has a rubber coating on its inner surface (the surface which engages two of the inventive rings which have been aligned with each other), and which is configured to be crimped around aligned docking features of the two aligned rings. FIG. 25F is a diagram showing the clip of FIG. 25E crimped around docking arms of aligned anastomosis rings.

Figure 25G:
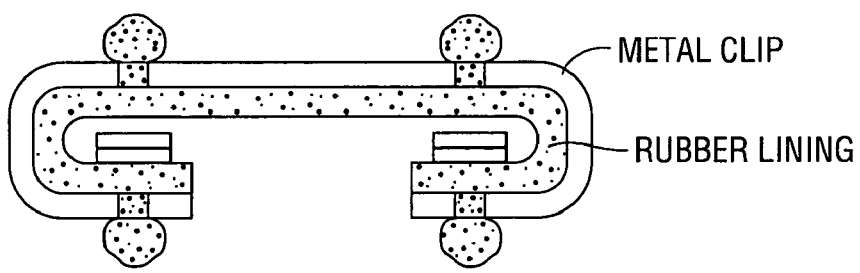

FIG. 25G is a cross-sectional view of a variation on the clip of FIG. 25E, having rubber appendages protruding from small holes therethrough.

Figure 25H:
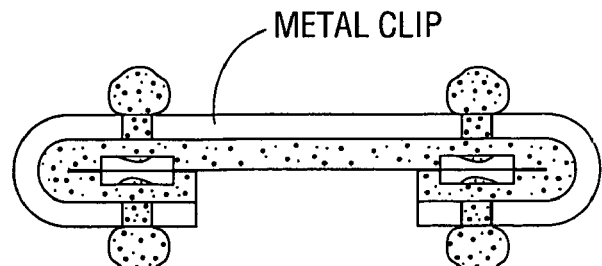

FIG. 25H is a cross-sectional view of the clip of FIG. 25G, after it has been crimped around docking arms of aligned anastomosis rings.

Figure 26:
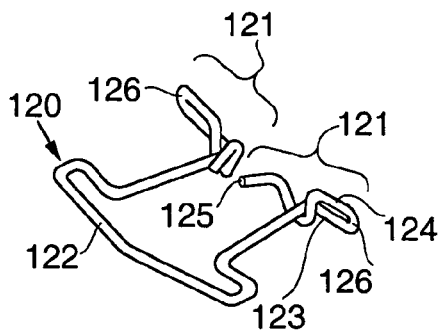

FIG. 26 is a perspective view of a spring clip (made of stainless steel wire) which can be sprung around aligned docking features of two of the inventive rings.

Figure 27:
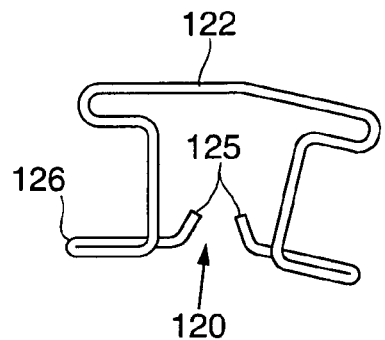

FIG. 27 is a top view of the spring clip of FIG. 26.

Figure 28:
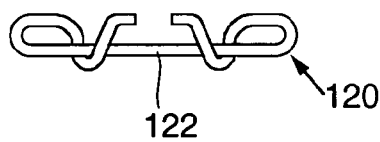

FIG. 28 is an end view of the spring clip of FIG. 26.

Figure 29:
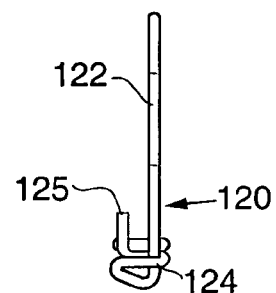

FIG. 29 is an side view of the spring clip of FIG. 26.

Figure 30:
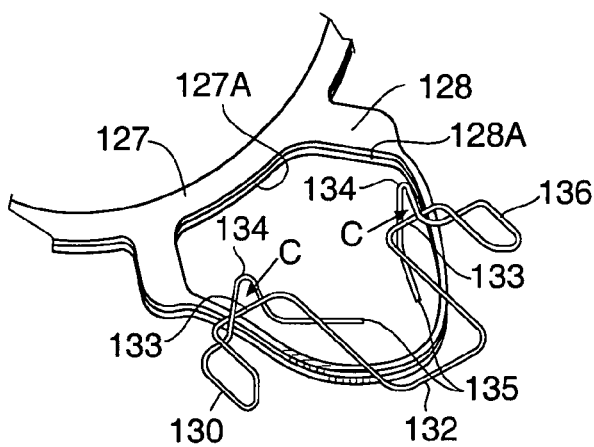

FIG. 30 is a perspective view of another embodiment of the inventive spring clip (made of stainless steel wire) shown after it has been sprung around aligned docking features of two of the inventive anastomosis rings.

Figure 31:
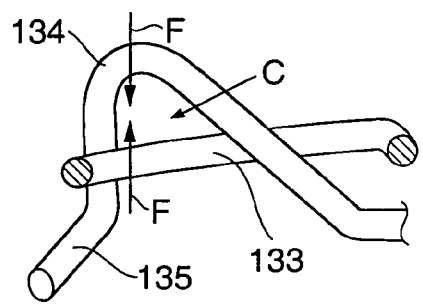

FIG. 31 is an enlarged detail of a portion of spring clip 130 of FIG. 30.

Figure 21:
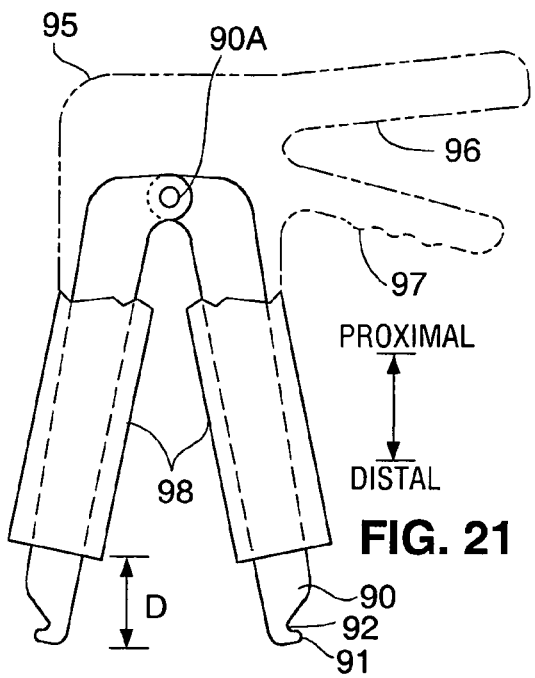
FIG. 21 is a simplified cross-sectional view of an apparatus for fastening together two of the inventive anastomosis rings (after the rings have been aligned with each other), by attaching two fastener clips around docking features of the rings.
Figure 22:
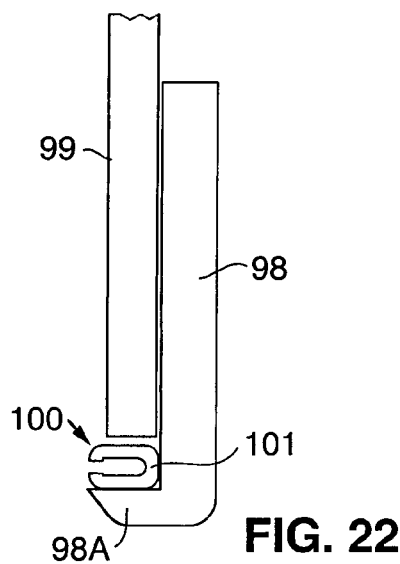
FIG. 22 is a perspective view of a detail of one implementation of the FIG. 21 apparatus, in which the apparatus functions to crimp a fastener clip around one set of aligned docking features of the rings.
Figure 32:
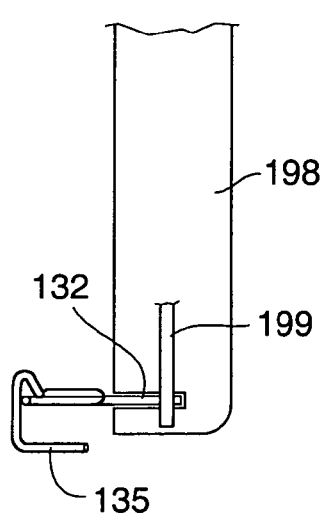

FIG. 32 is a side view (partially cut away) of a detail of a variation on the FIG. 22 implementation of the FIG. 21 apparatus, in which the apparatus functions to cause at least one spring clip to clamp together aligned docking features of two of the inventive rings.

Figure 33:
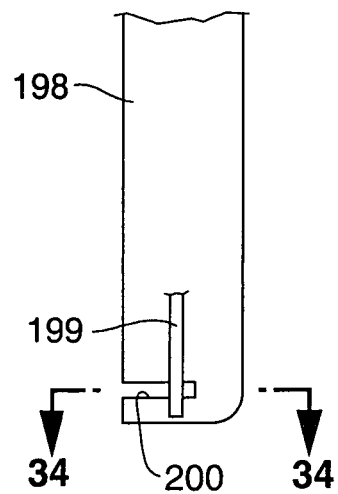

FIG. 33 is a side view of the FIG. 32 apparatus with the spring clip removed from it.

Figure 34:
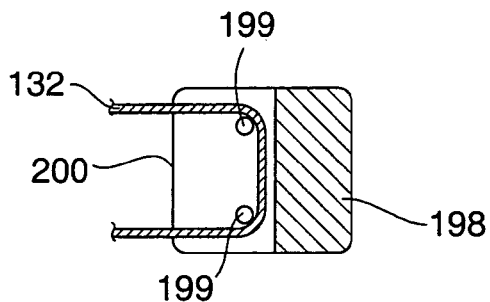

FIG. 34 is a cross-sectional view of the FIG. 33 apparatus taken along line 34-34 of FIG. 33.

Figure 35:
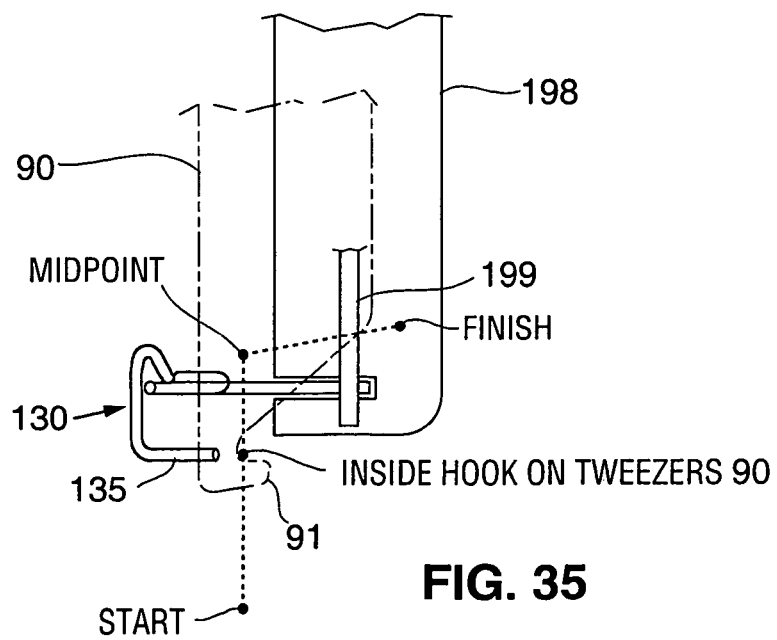

FIG. 35 is a side view (partially cut away) of the apparatus of FIG. 32, showing forceps 90 in phantom view.

Figure 36:
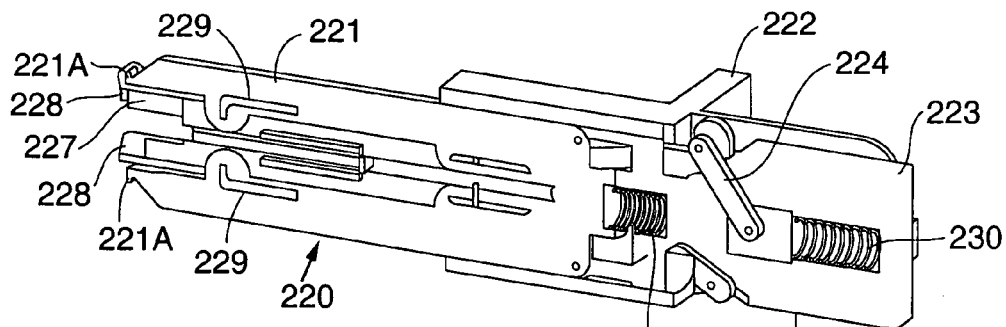

FIG. 36 is a cut-away perspective view of an embodiment of the inventive tool for aligning two of the inventive rings and crimping fastener clips around aligned docking features of the aligned rings.

Figure 37:
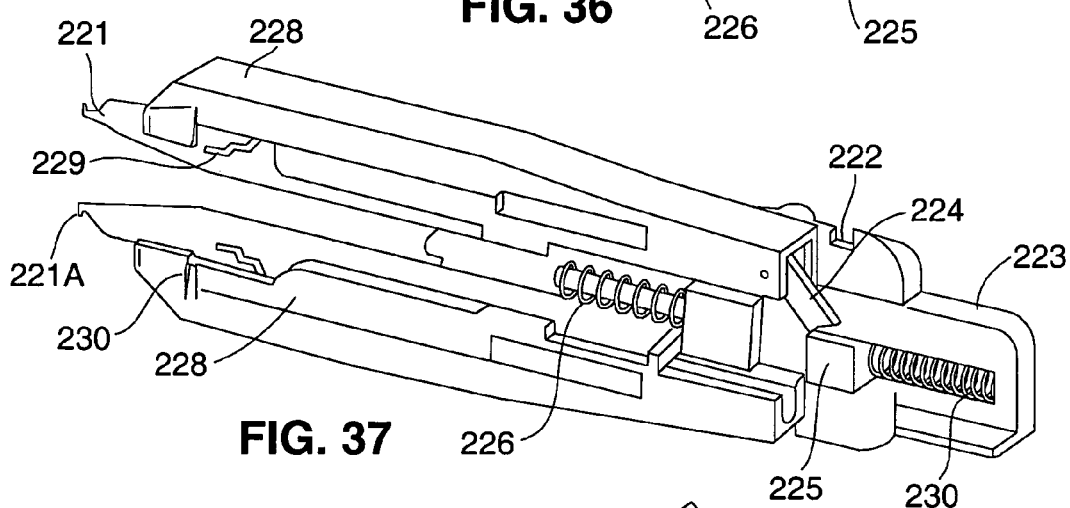

FIG. 37 is a cut-away perspective view of the FIG. 36 tool, showing additional elements of the tool (additional portions of carriers 228) that are not shown in FIG. 36, and showing carriers 228 fully retracted relative to forceps 221.

Figure 38:
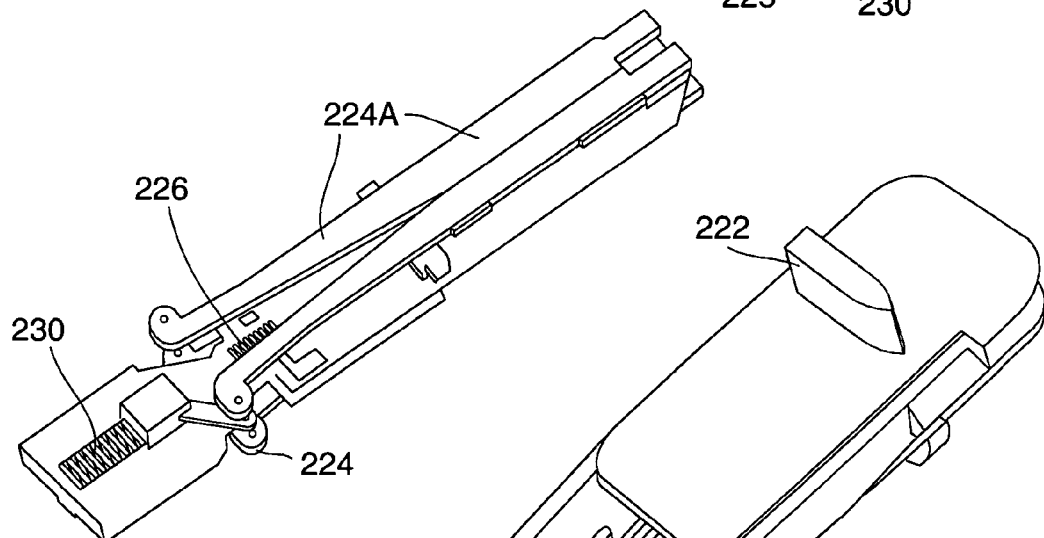

FIG. 38 is a perspective view of a portion of the FIG. 36 tool.

Figure 39:
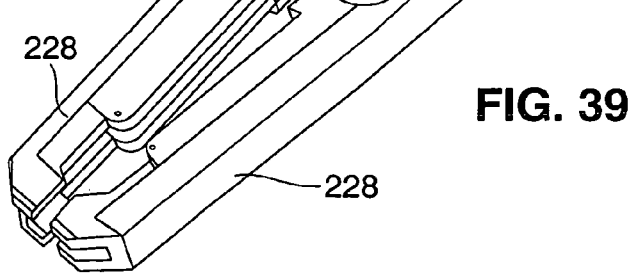

FIG. 39 is a perspective view of the entire FIG. 36 tool, with carriers 228 filly extended relative to forceps 221.

Figure 40:
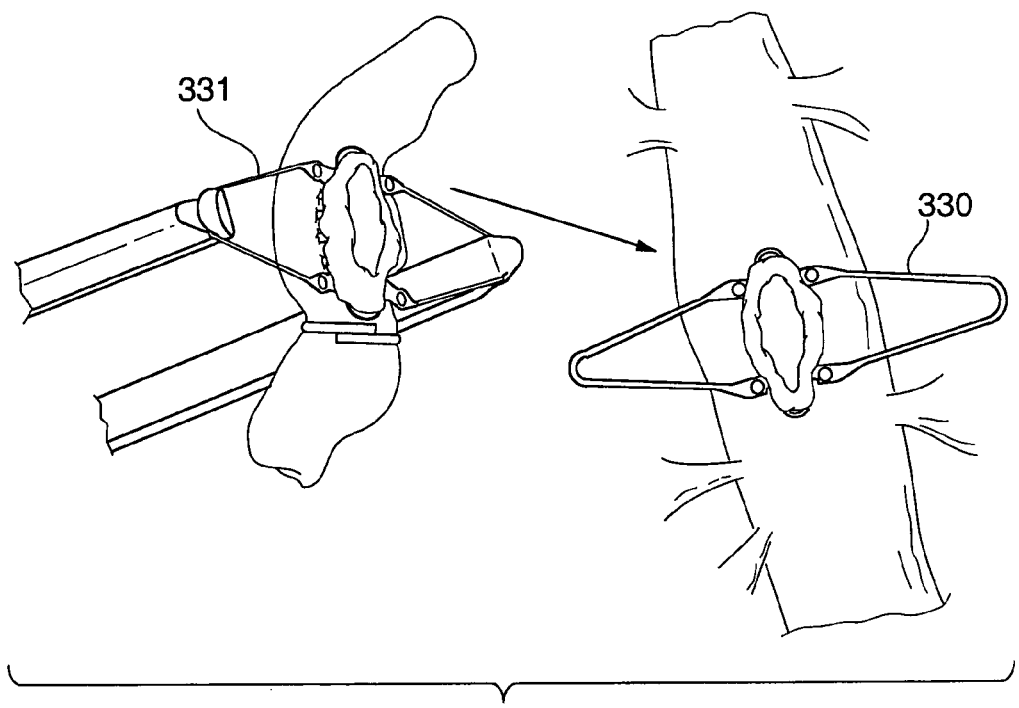

FIG. 40 shows one of the inventive anastomosis rings (ring 330) installed in an orifice in a coronary artery, and another of the inventive anastomosis rings (ring 331) installed in an orifice in a graft vessel. The docking arms of ring 331 are held in notches at the ends of the arms of a forceps, and the forceps is being moved toward ring 330, in order to roughly align the two rings.

Figure 41:
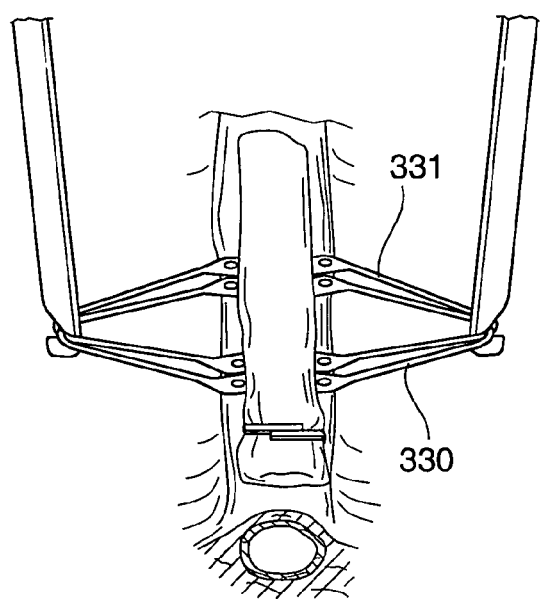

FIG. 41 shows rings 331 and 330 (of FIG. 40) after they have been brought into alignment with each other.

Figure 42:
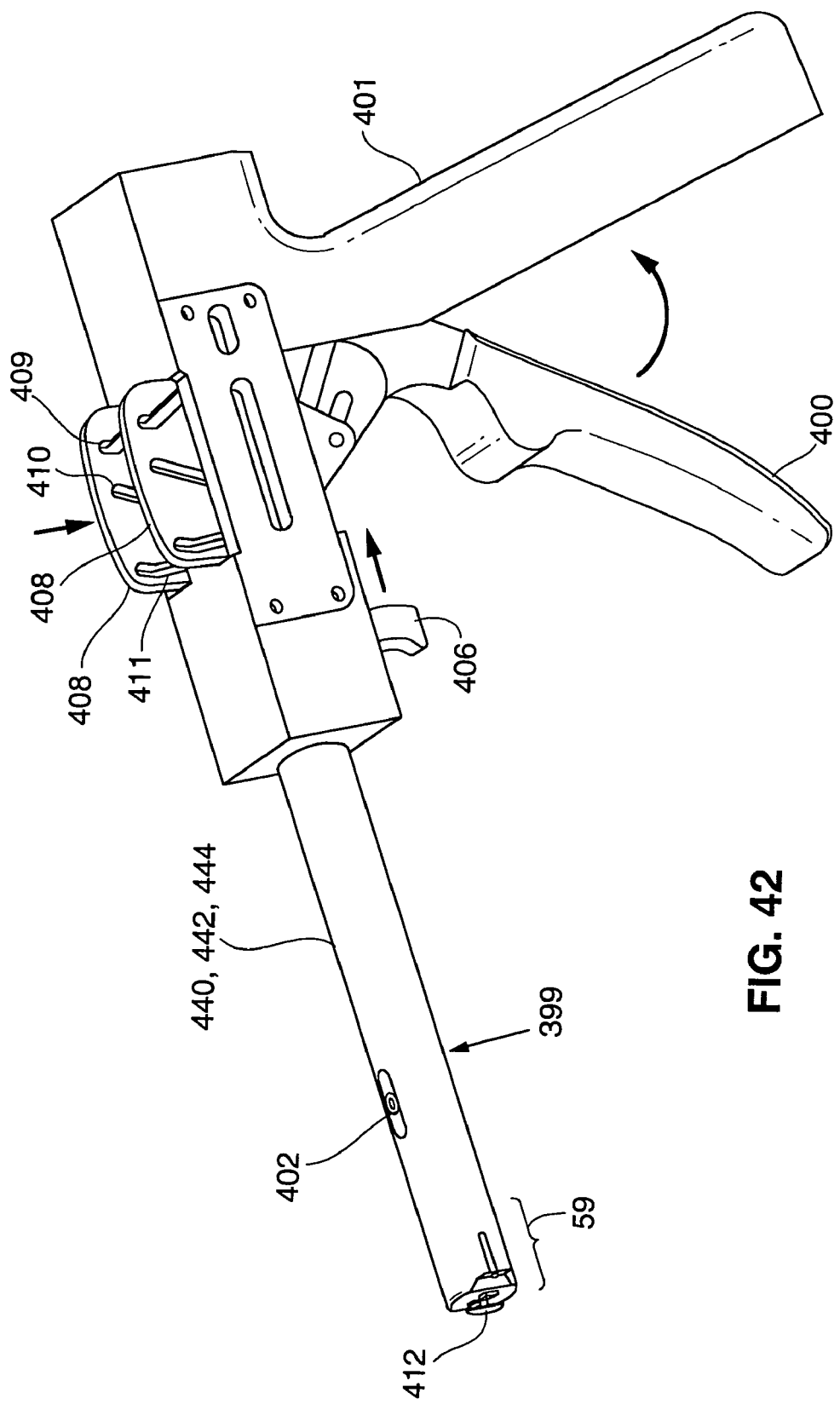

FIG. 42 is a perspective view of an embodiment of the inventive tool for installing an anastomosis ring (designed in accordance with the invention) in an incision (or other orifice) in a vessel or other organ.

Figure 43:
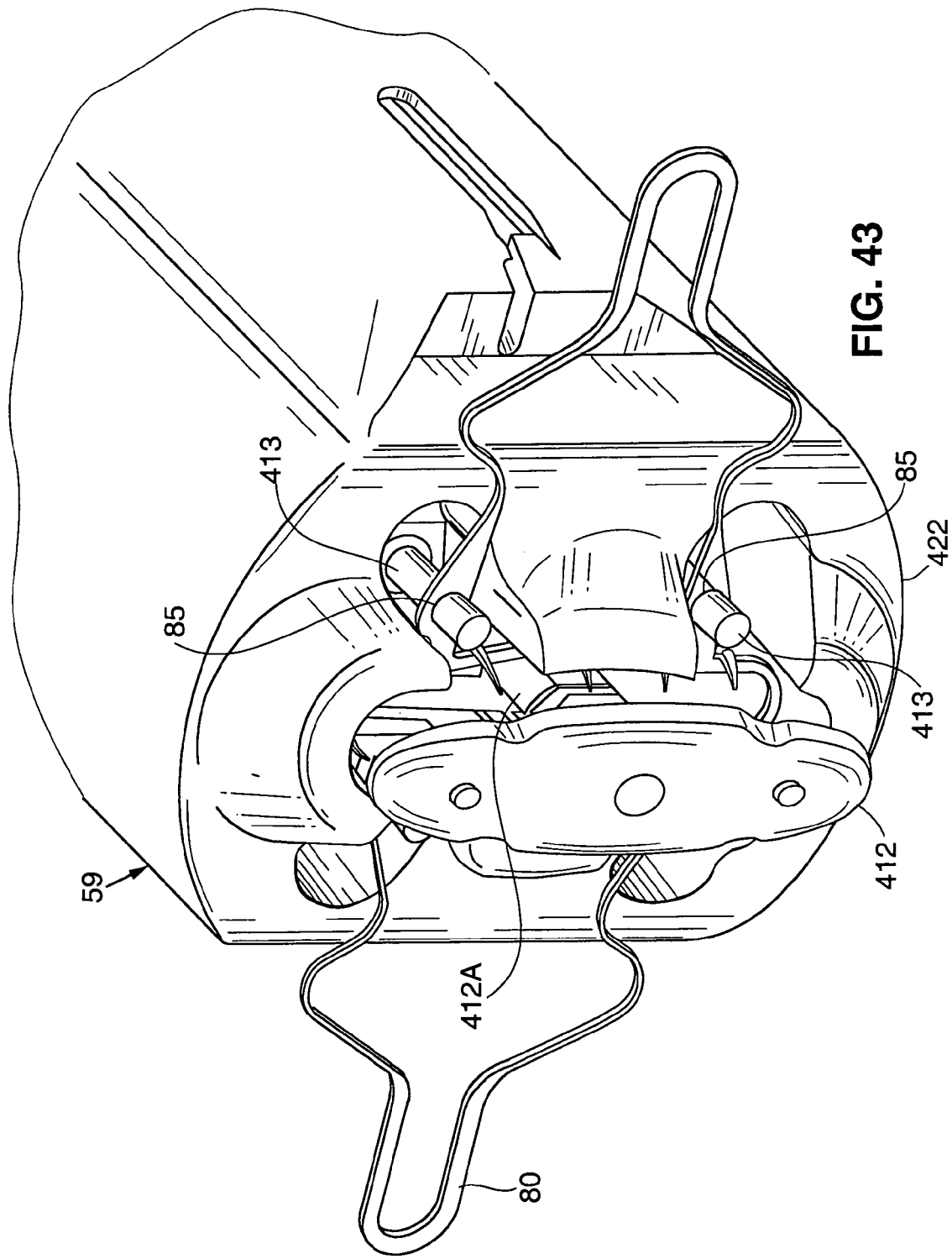

FIG. 43 is a perspective view of the distal end portion of the tool of FIG. 42.

Figure 44:
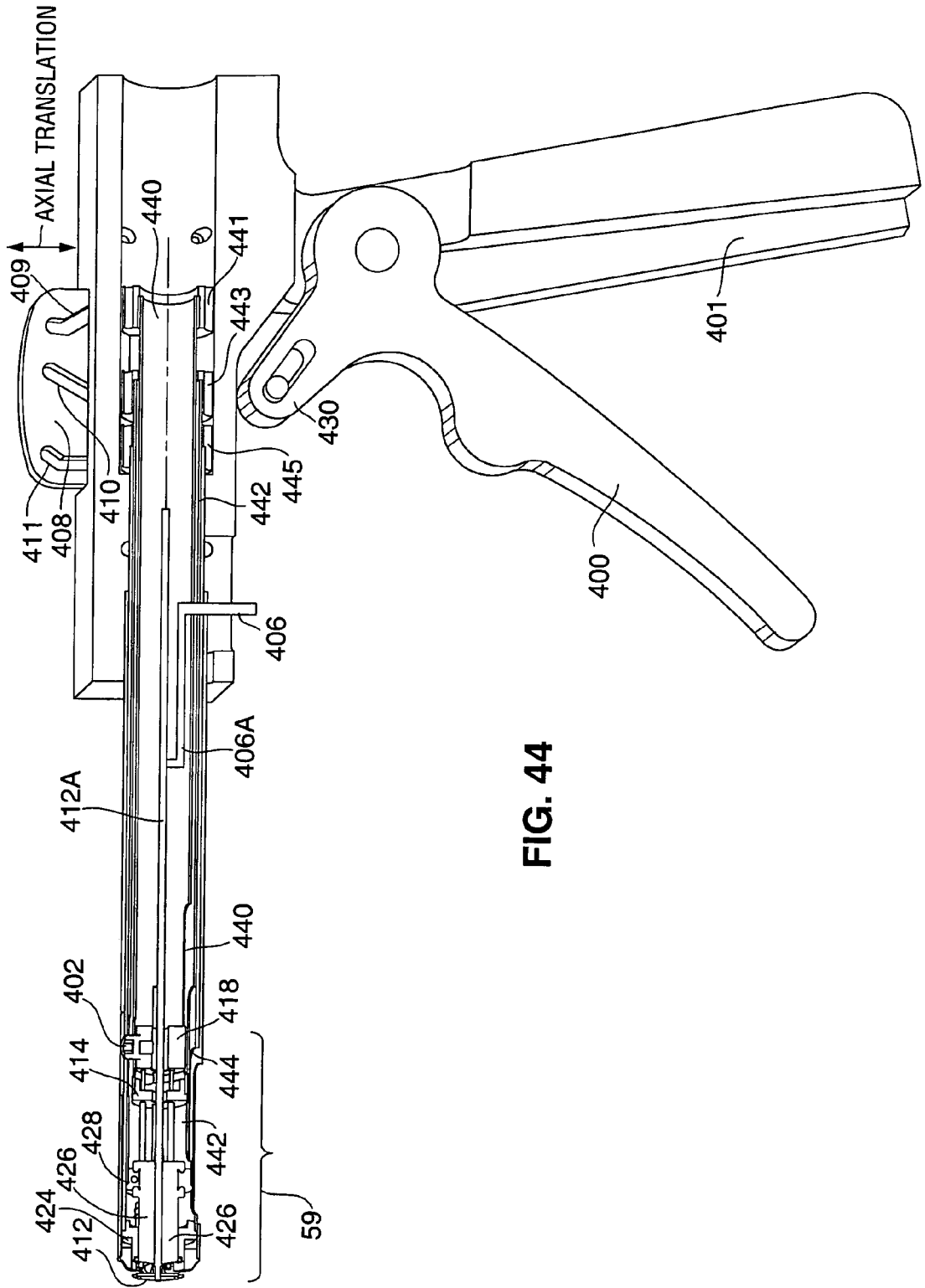

FIG. 44 is a cross-sectional view of the tool of FIG. 42.

Figure 45:
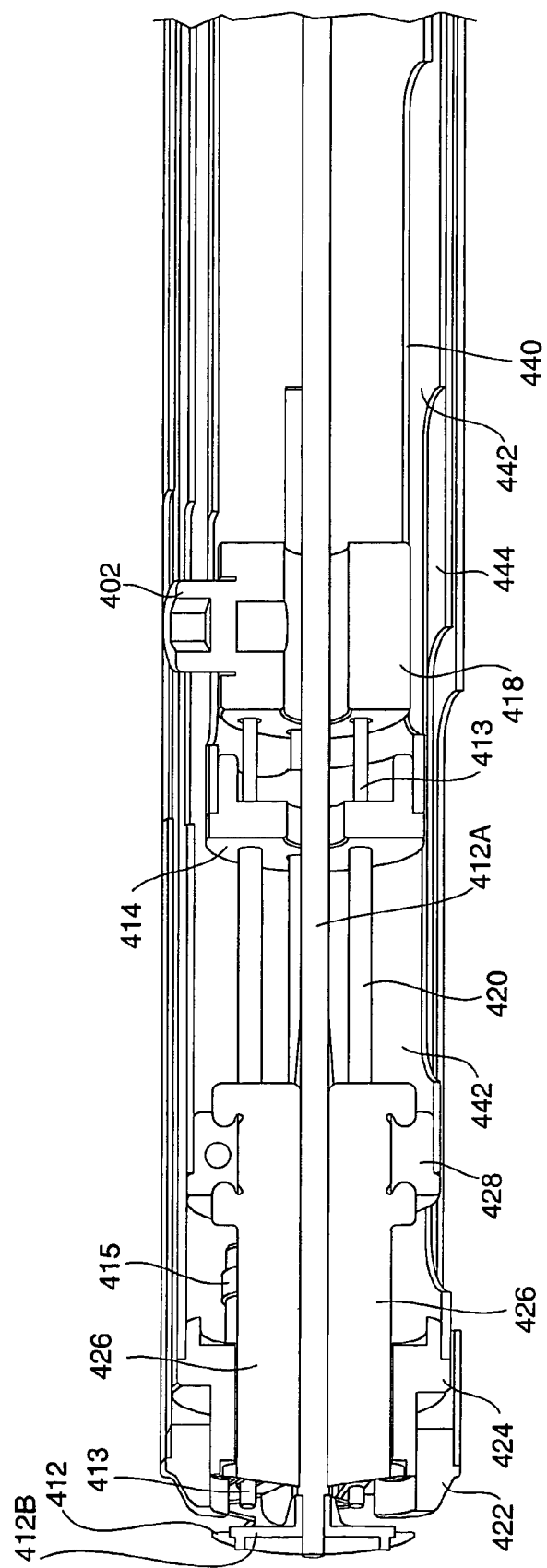

FIG. 45 is an enlarged version of the portion of FIG. 44 that shows the distal end of the tool of FIG. 42.

Figure 46:
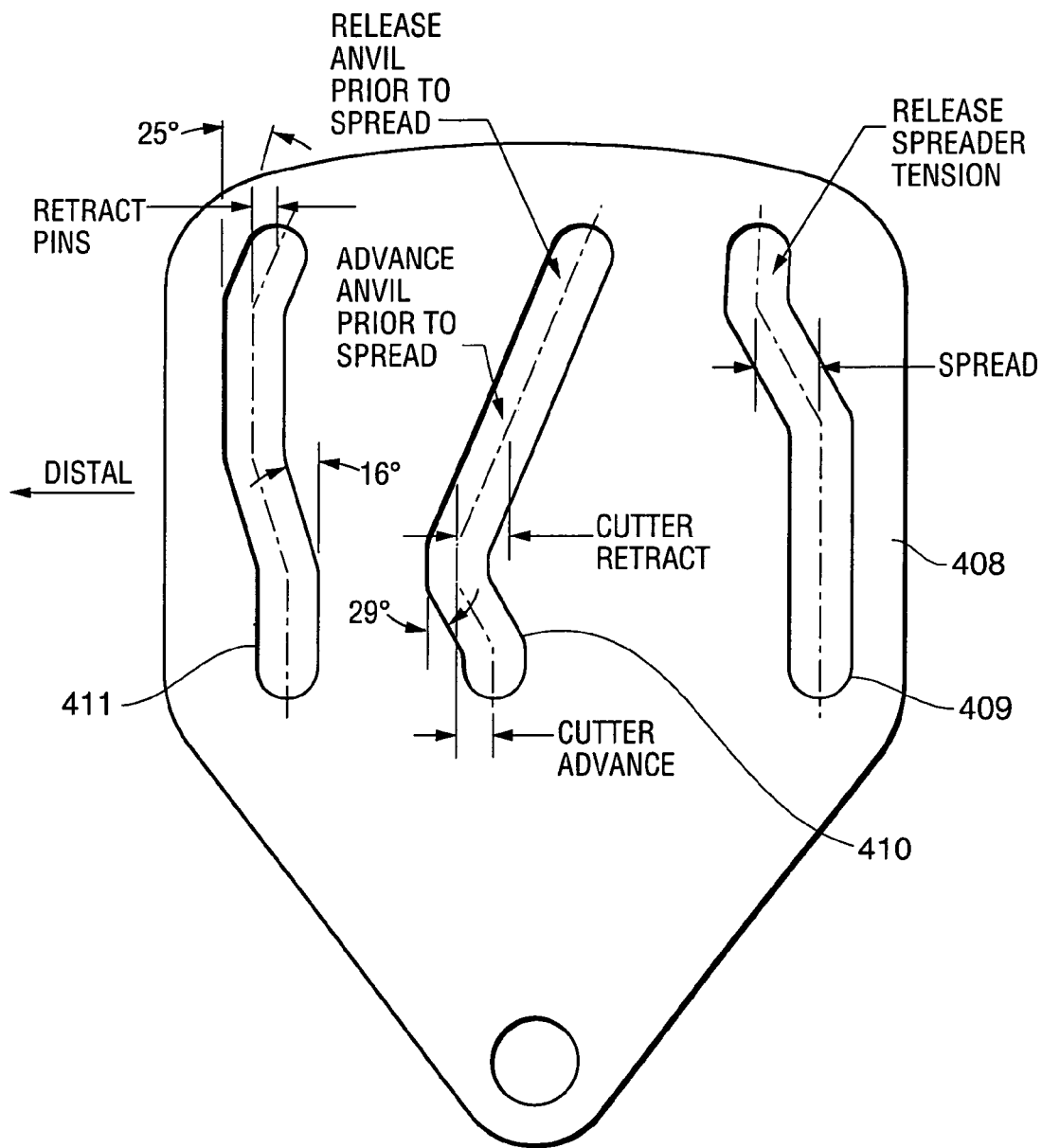

FIG. 46 is a side elevational view of one of the cam plates of the tool of FIG. 42.

FIG. 47 is a perspective view of a portion of the tool of FIG. 42.

Figure 47A:
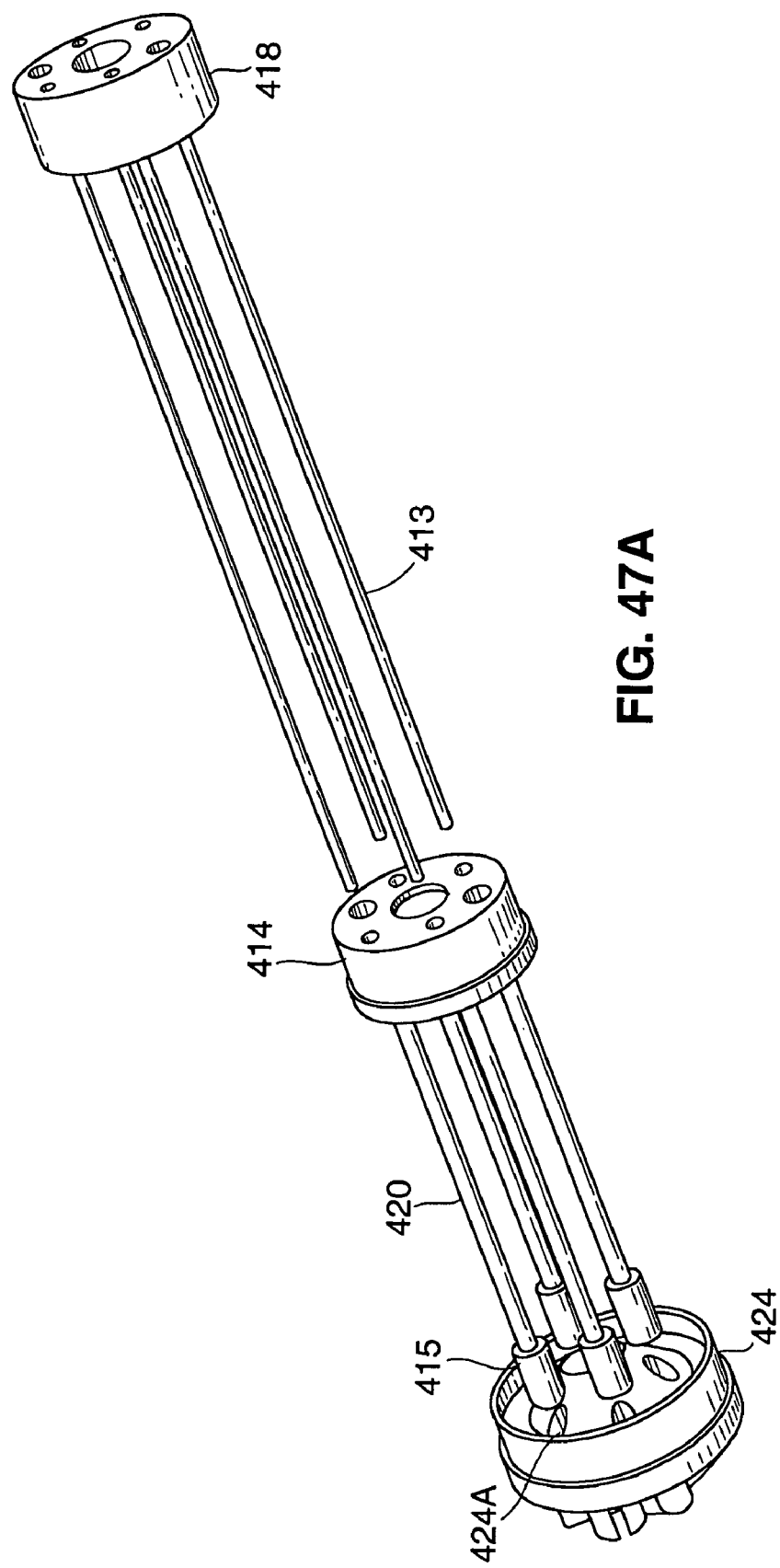

FIG. 47A is an exploded perspective view of some of the elements shown in FIG. 47.

Figure 48:
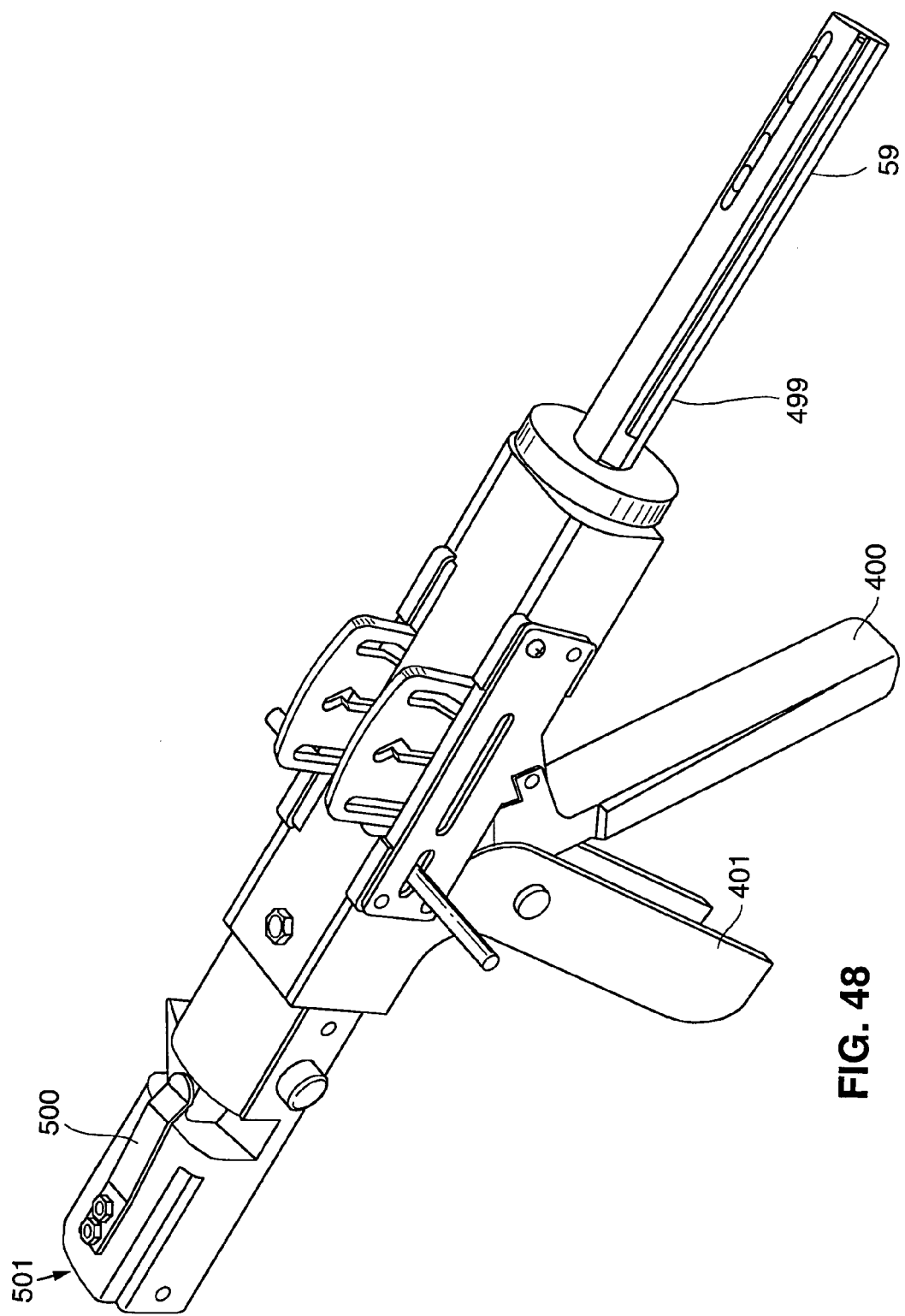

FIG. 48 is a perspective view of a variation on the tool of FIG. 42.

Figure 49:
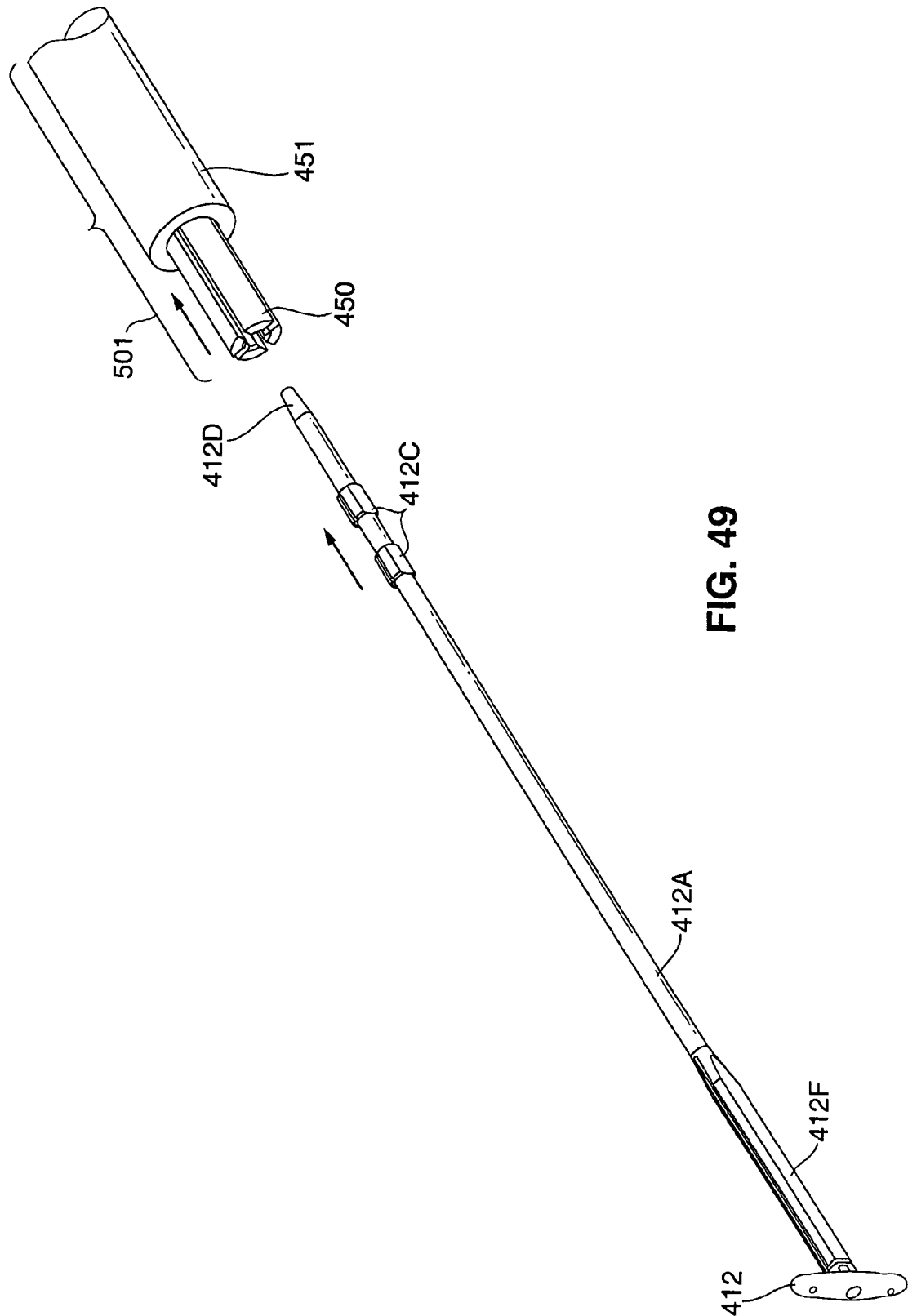

FIG. 49 is a perspective view of the anvil assembly and the distal end of rear assembly 501 of the tool of FIG. 48.

Figure 50:
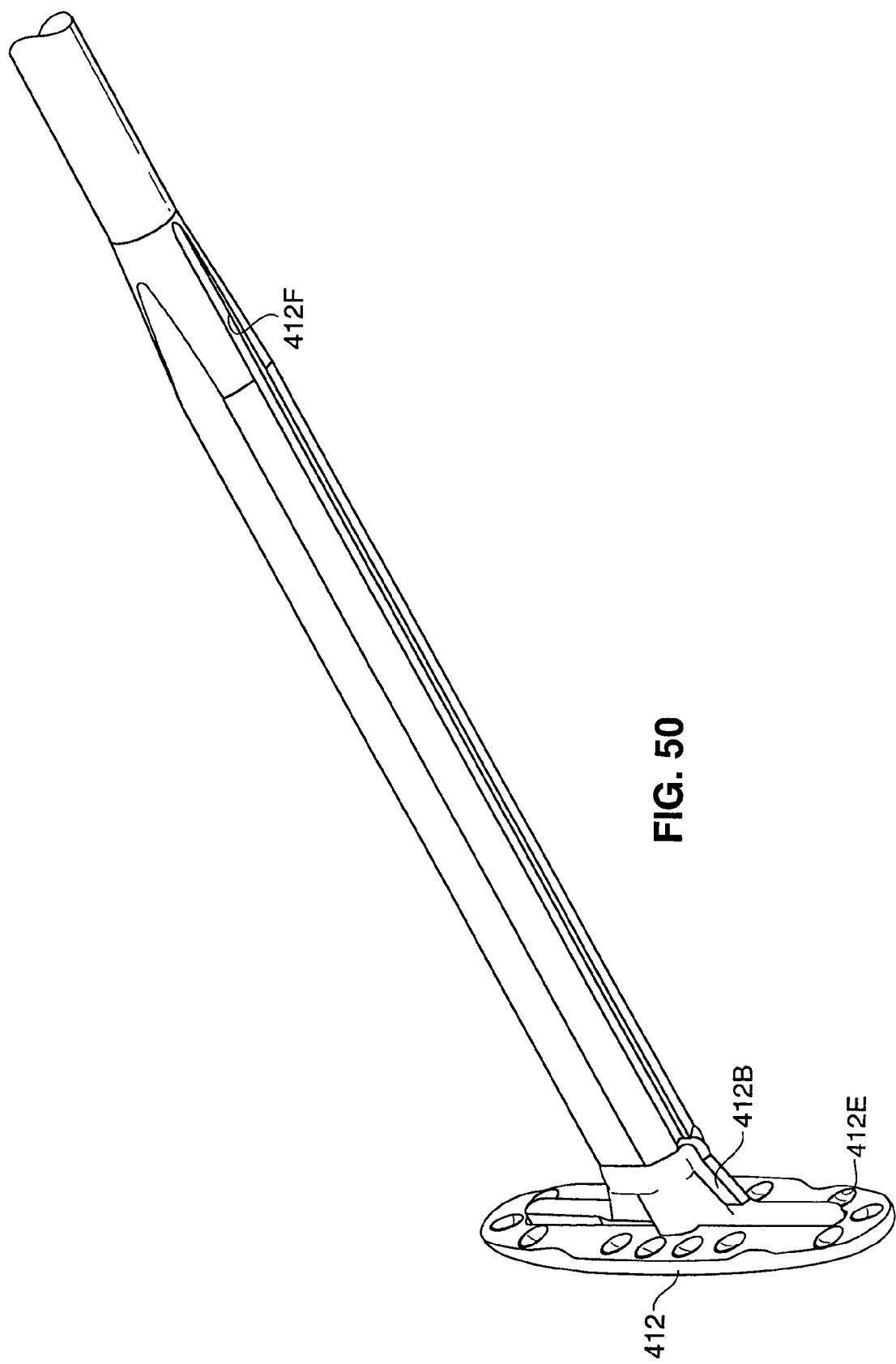

FIG. 50 is a perspective view of the distal portion of the anvil assembly of the FIG. 48 tool.

Figure 51:
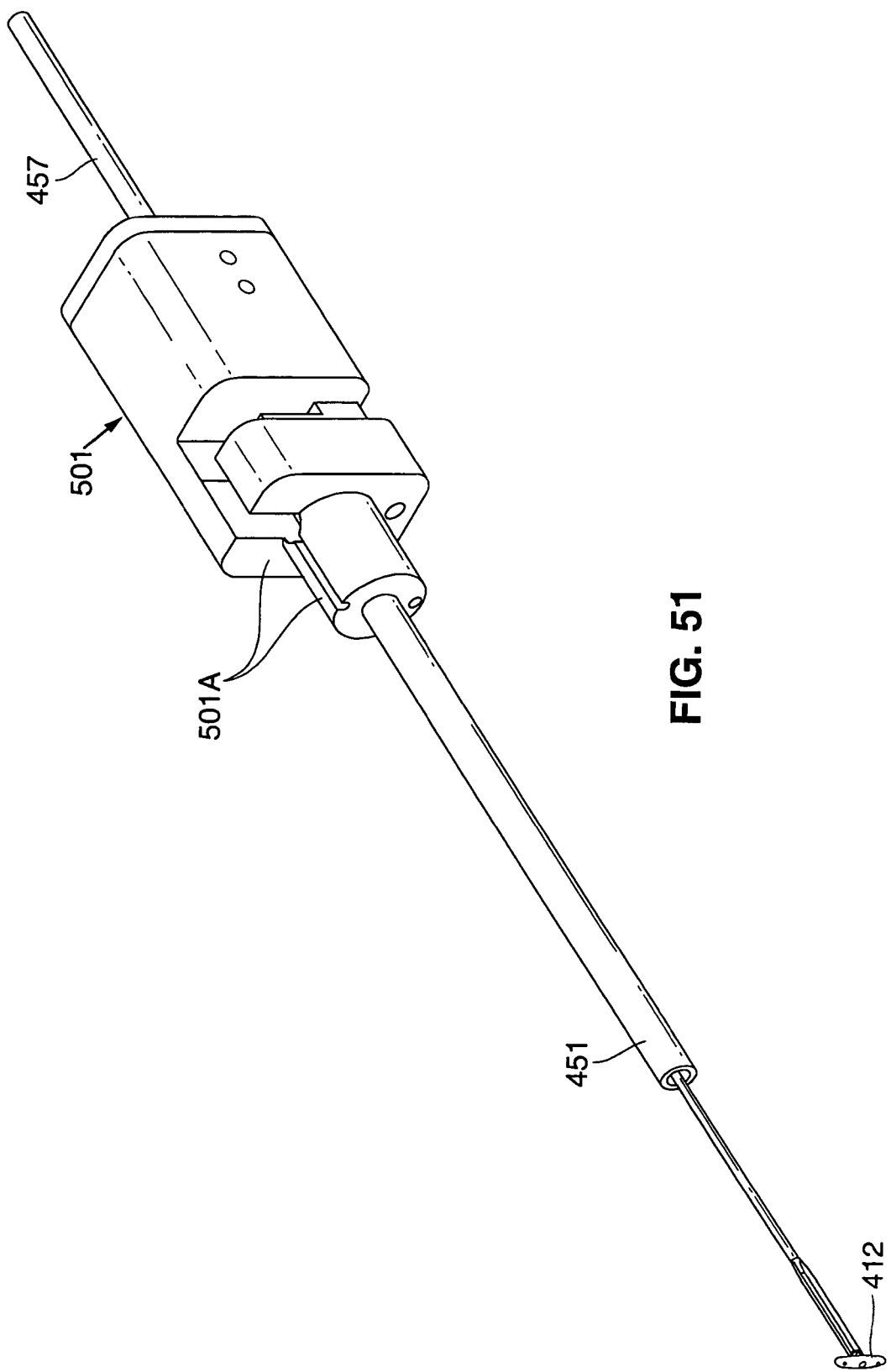

FIG. 51 is a perspective view of rear assembly 501 (with elements 459 and 452 omitted) and the anvil assembly of the FIG. 48 tool.

Figure 52:
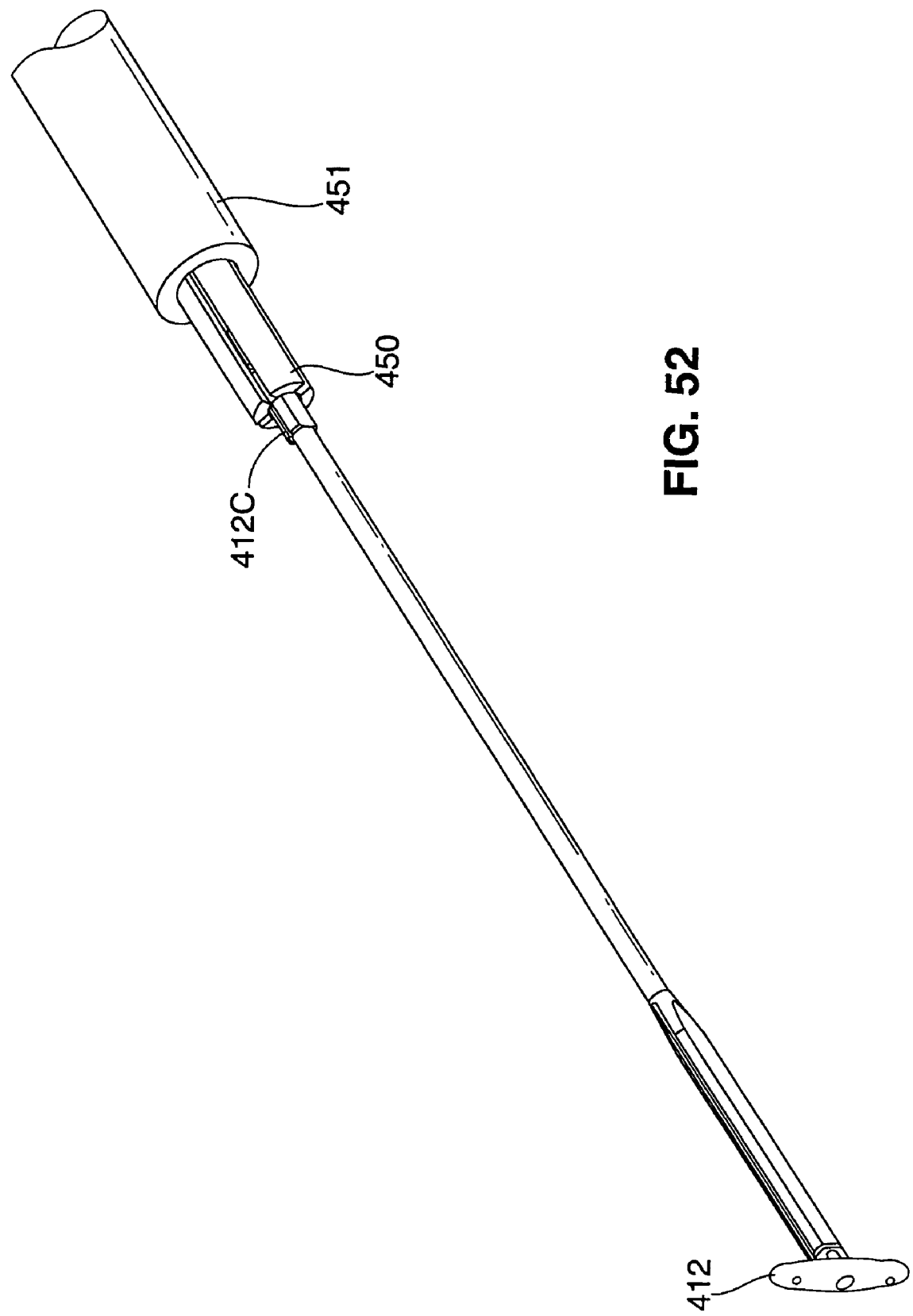

FIG. 52 is a perspective view of the anvil assembly and the distal end of rear assembly 501 of the FIG. 48 tool, with the anvil assembly partially retracted into assembly 501.

Figure 53:
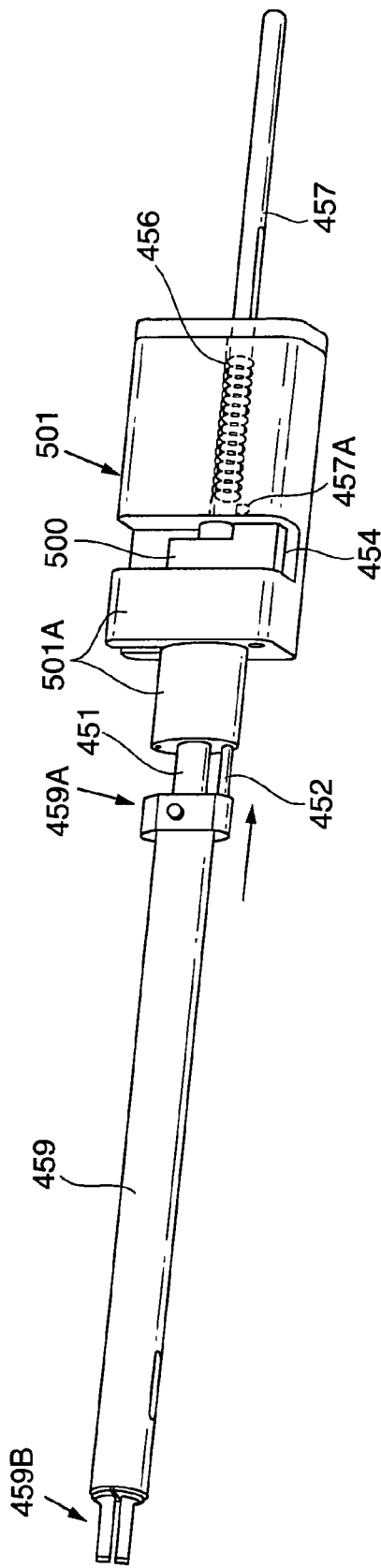

FIG. 53 is a perspective view of rear assembly 501 (including elements 459 and 452) and the anvil assembly of the FIG. 48 tool.

Figure 54:
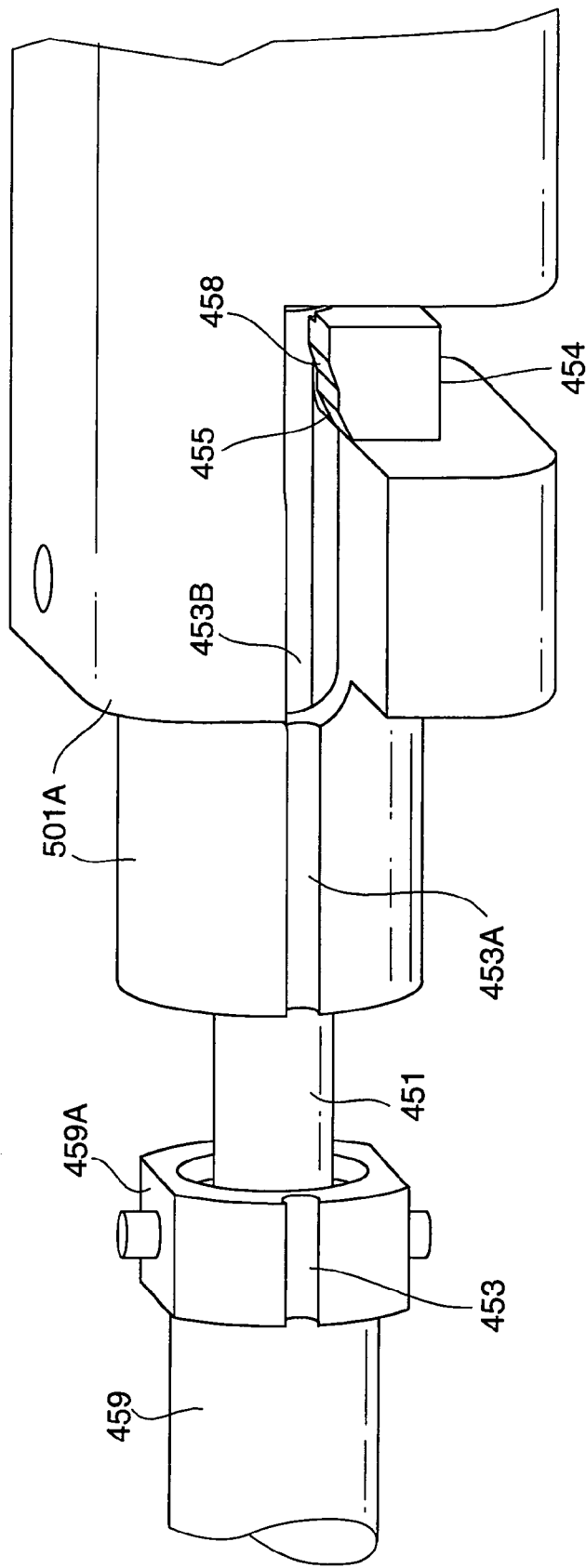

FIG. 54 is a detail of the FIG. 53 apparatus with pin 452 and spring 500 omitted.

Figure 55:
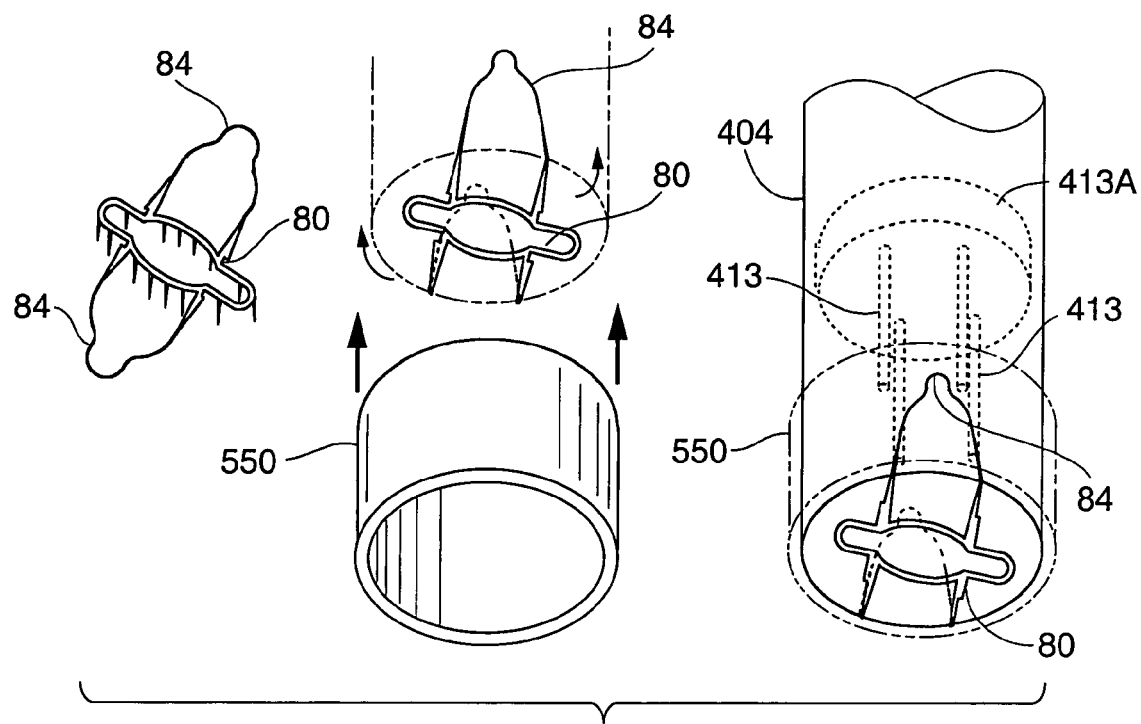

FIG. 55 is a set of perspective views of one means for mounting an anastomosis ring to an installation tool.

Figure 56:
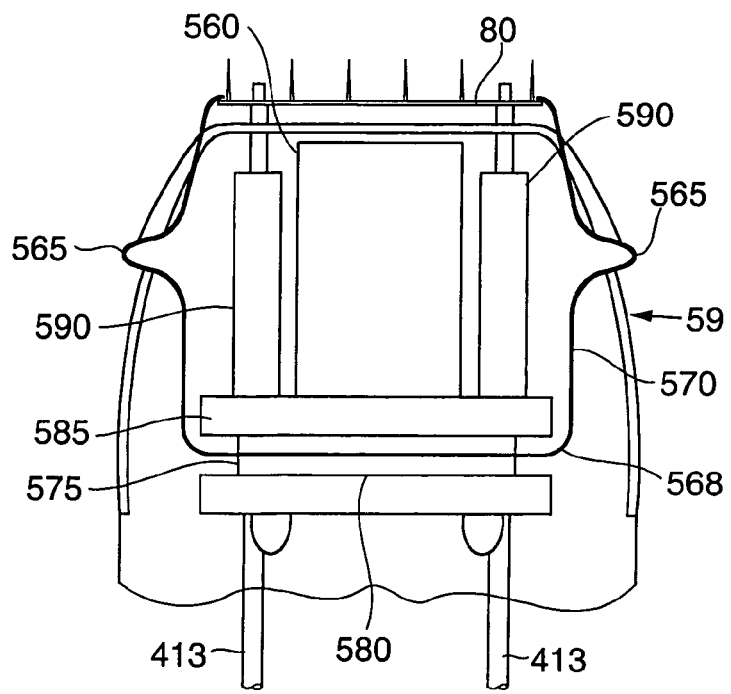

FIG. 56 is a cross-sectional view of the distal end of an installation tool and depicts another means for mounting an anastomosis ring to such tool.

Figure 57:
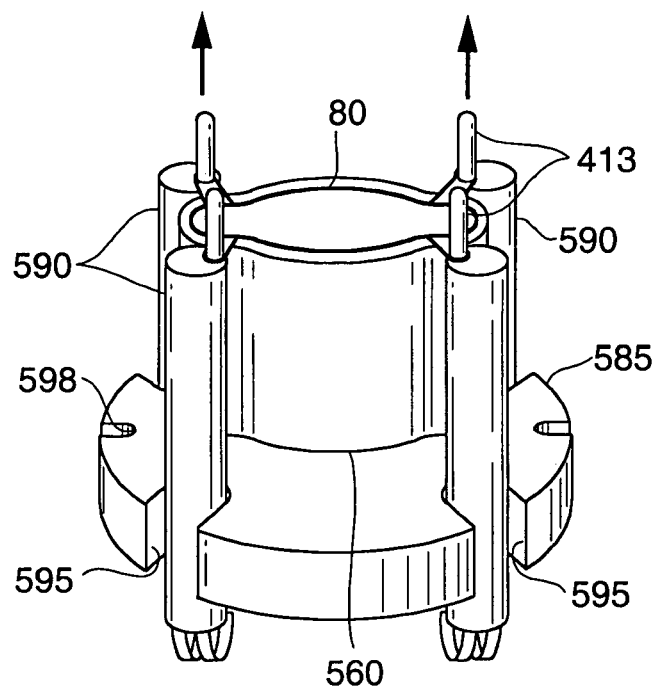

FIG. 57 depicts an alternative construction of the distal end of an installation tool, including a third embodiment of a means for mounting an anastomosis ring to an installation tool.

Figure 58:
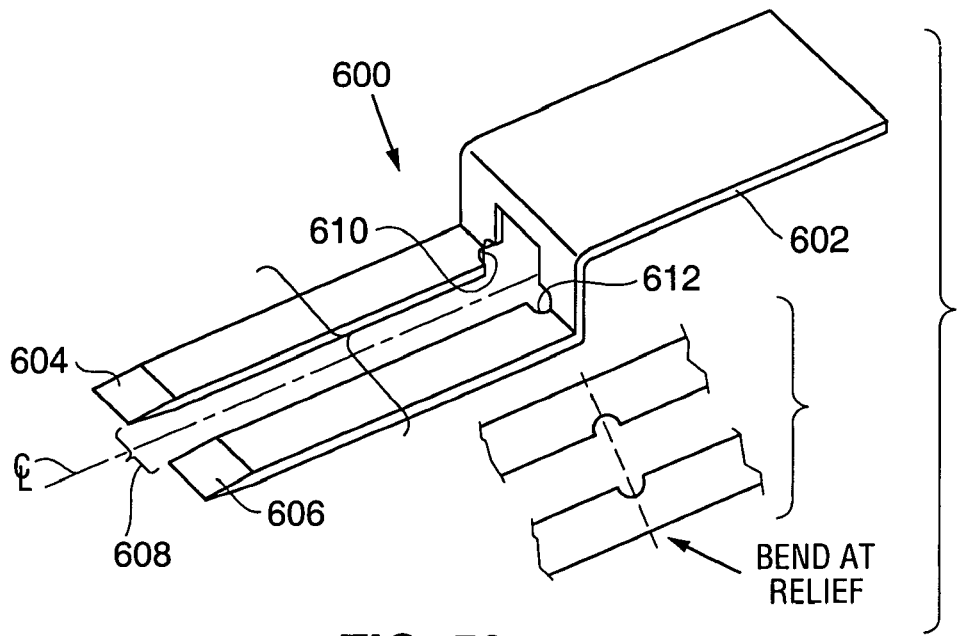

FIG. 58 depicts a cutting blade useful in installation tools of this invention.

Figure 59:
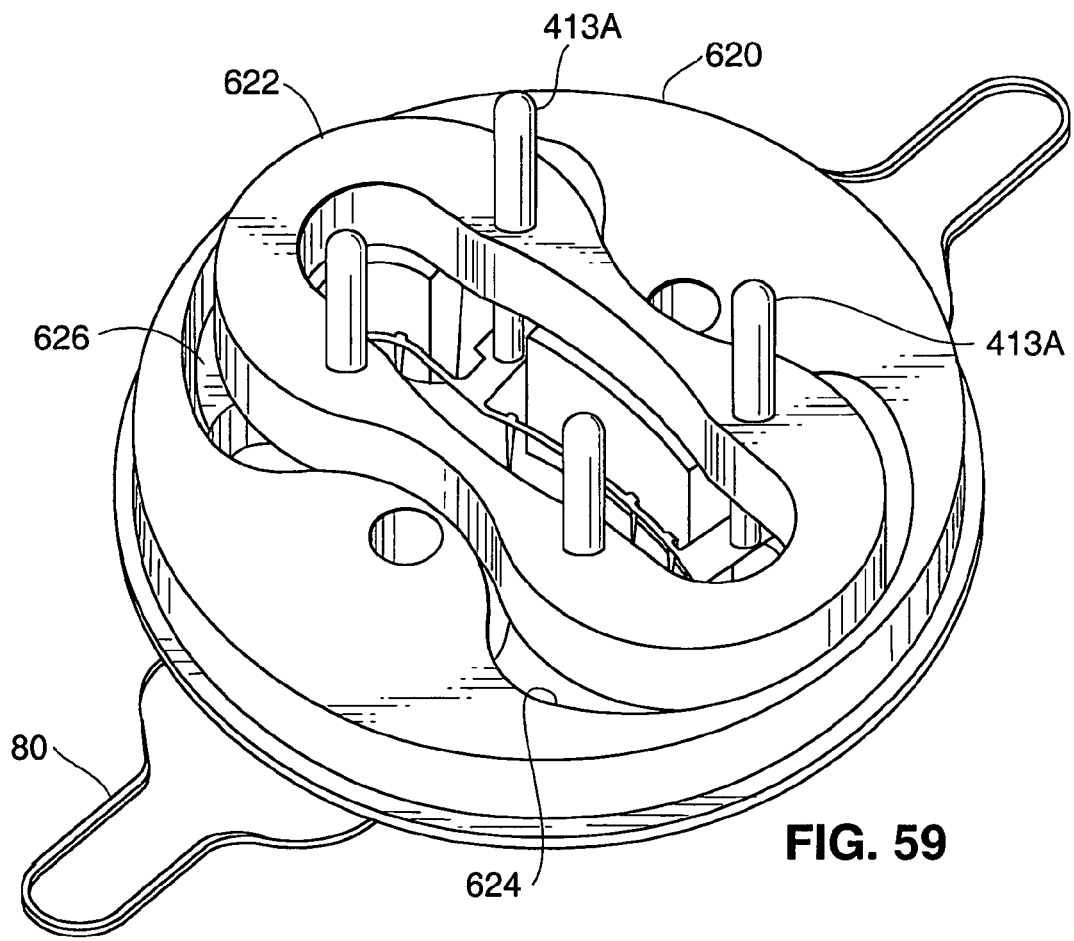

FIG. 59 is a perspective view of a means of retaining an anastomosis ring in the distal end of an installation tool using an elastomeric or compliant member.

Figure 60:
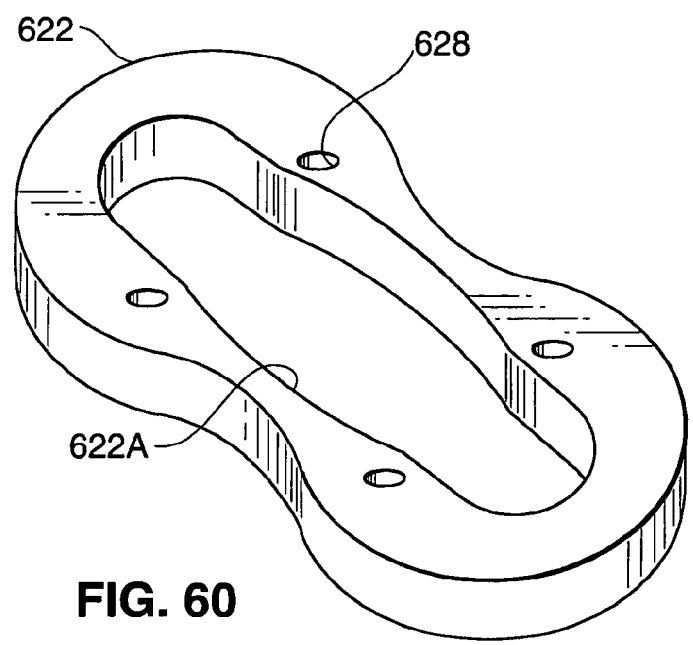

FIG. 60 depicts a central portion of the construction of FIG. 59.

Figure 61:
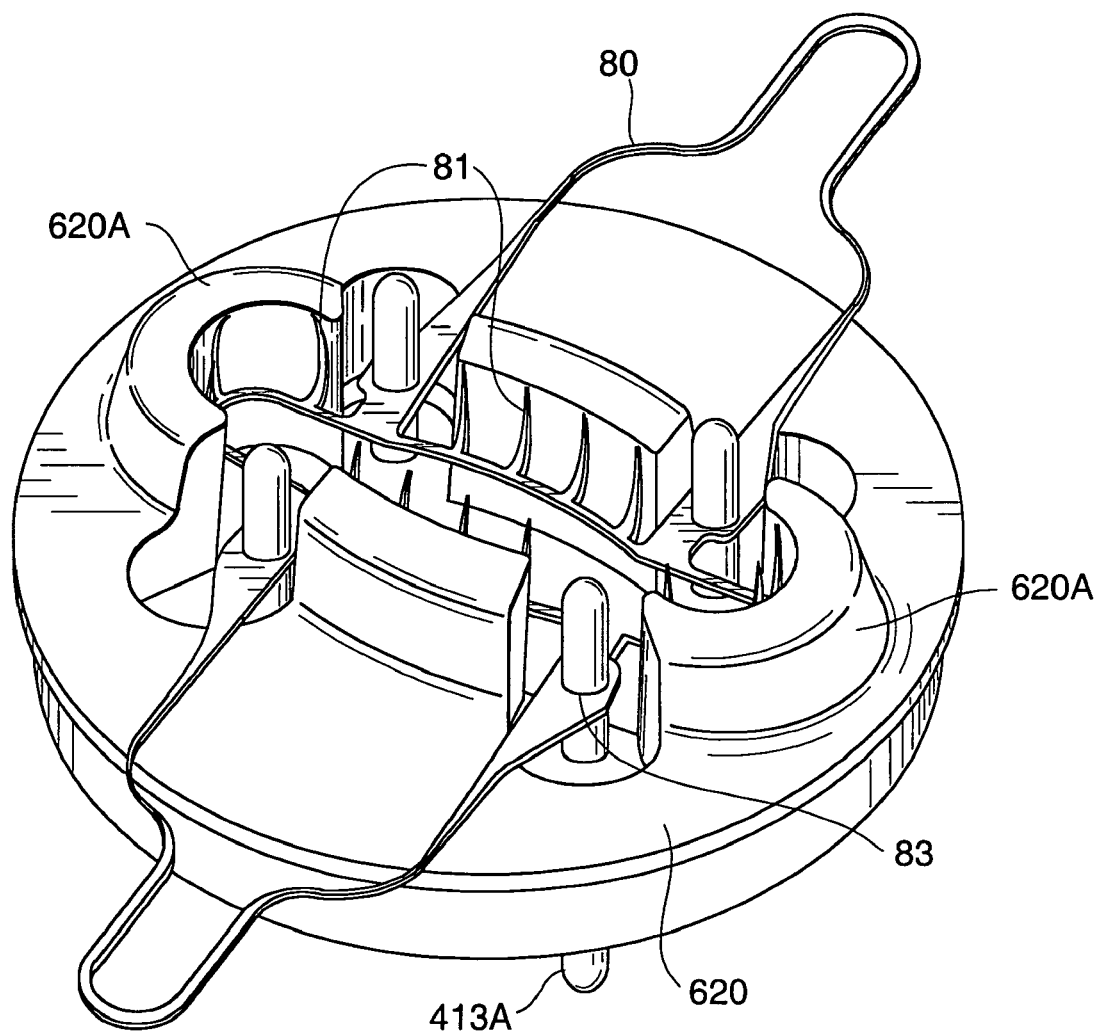

FIG. 61 depicts a reverse view of the construction of FIG. 59.

Figure 62:
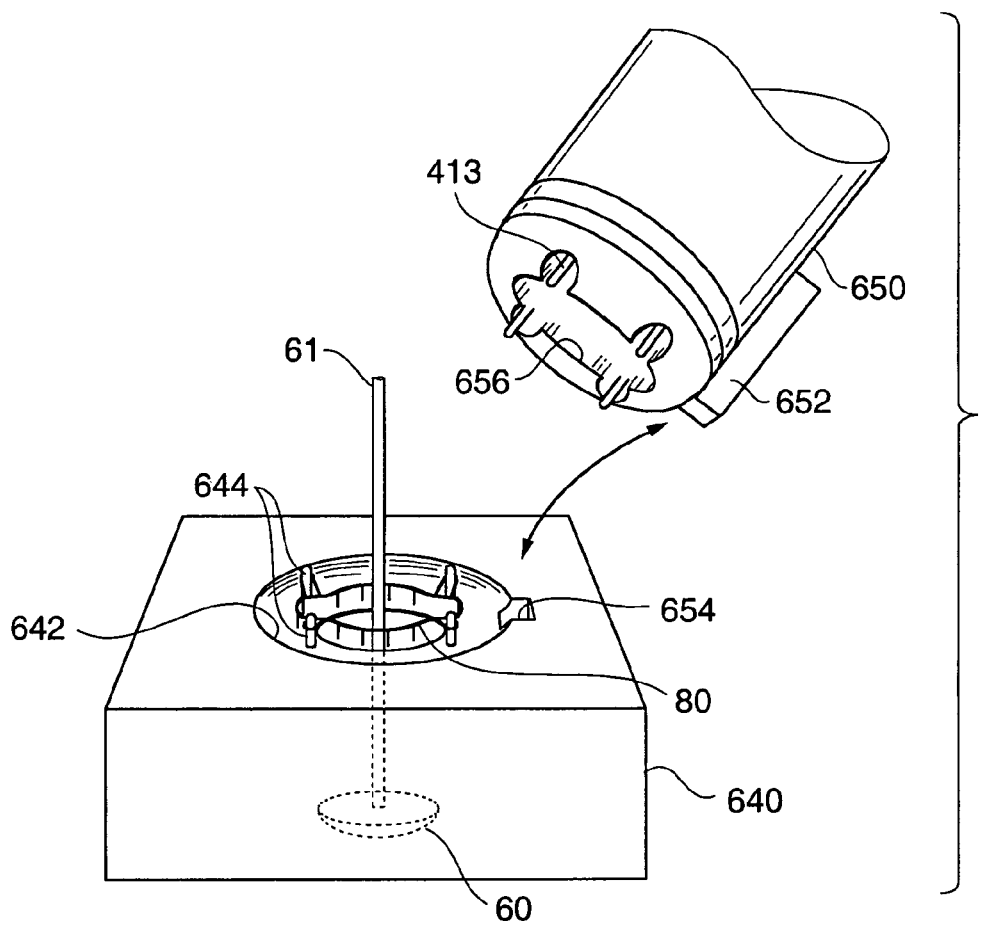

FIG. 62 depicts a loading device for loading a ring and optionally an anvil onto an installation tool.

Figure 63:
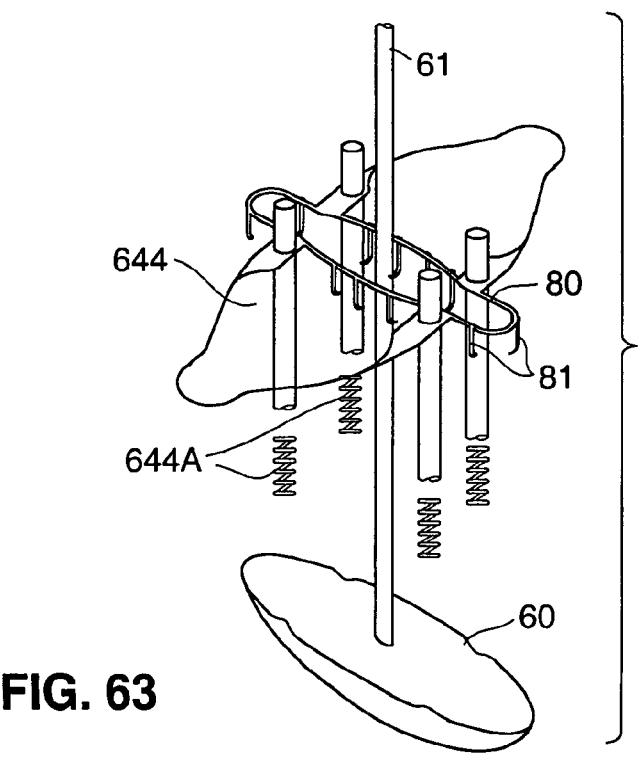

FIG. 63 depicts a portion of the internal construction of the loading device of FIG. 62.

Figure 64:
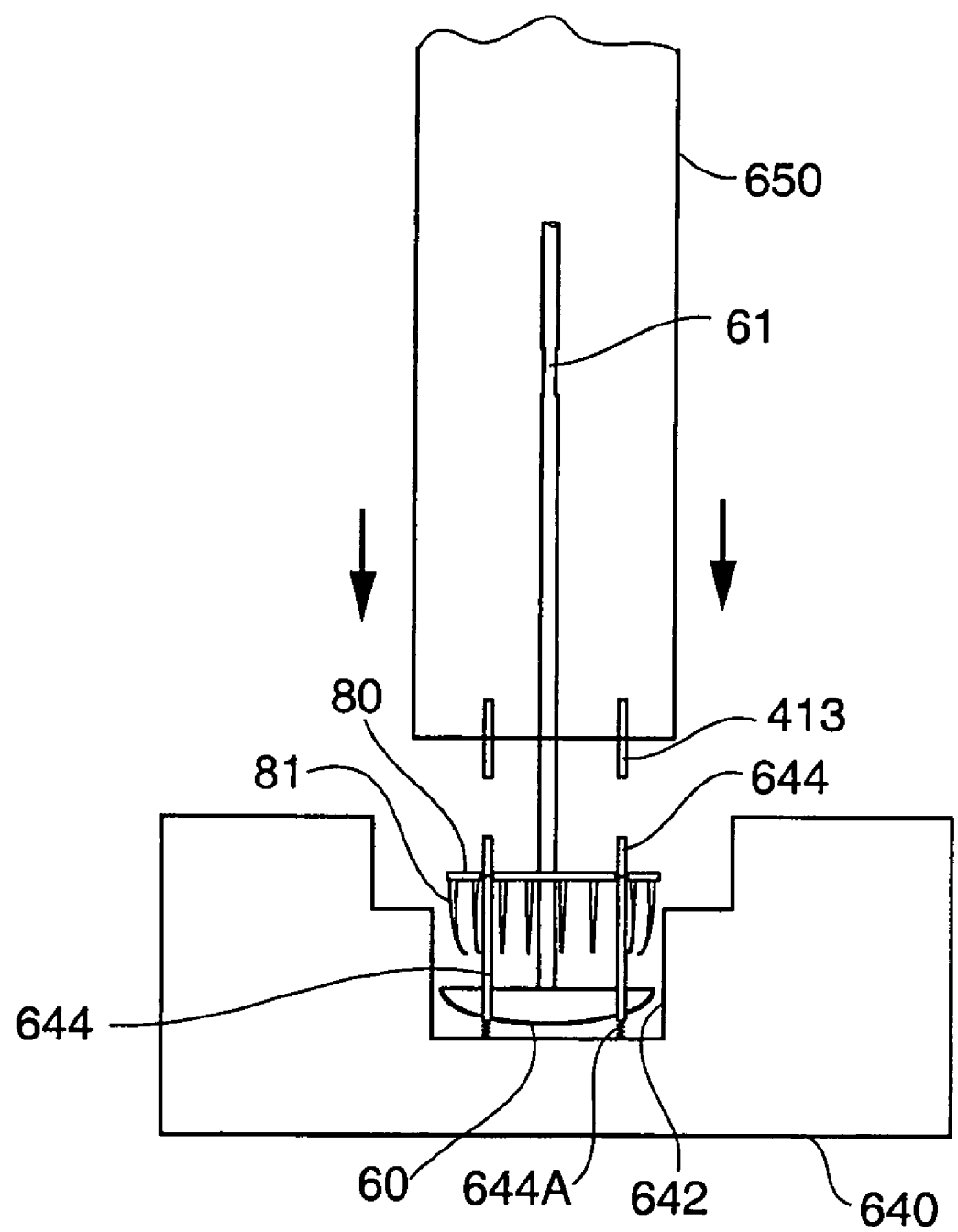

FIG. 64 depicts the matter of loading a ring and optionally an anvil into an installation tool using the embodiment of FIG. 62.

Figure 65:
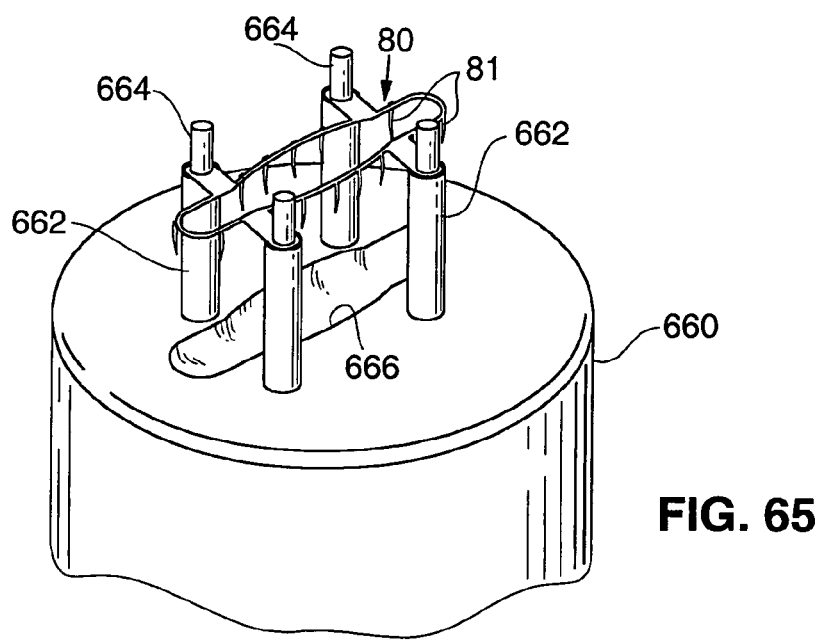

FIG. 65 depicts an alternative embodiment of a loading device.

Figure 66:
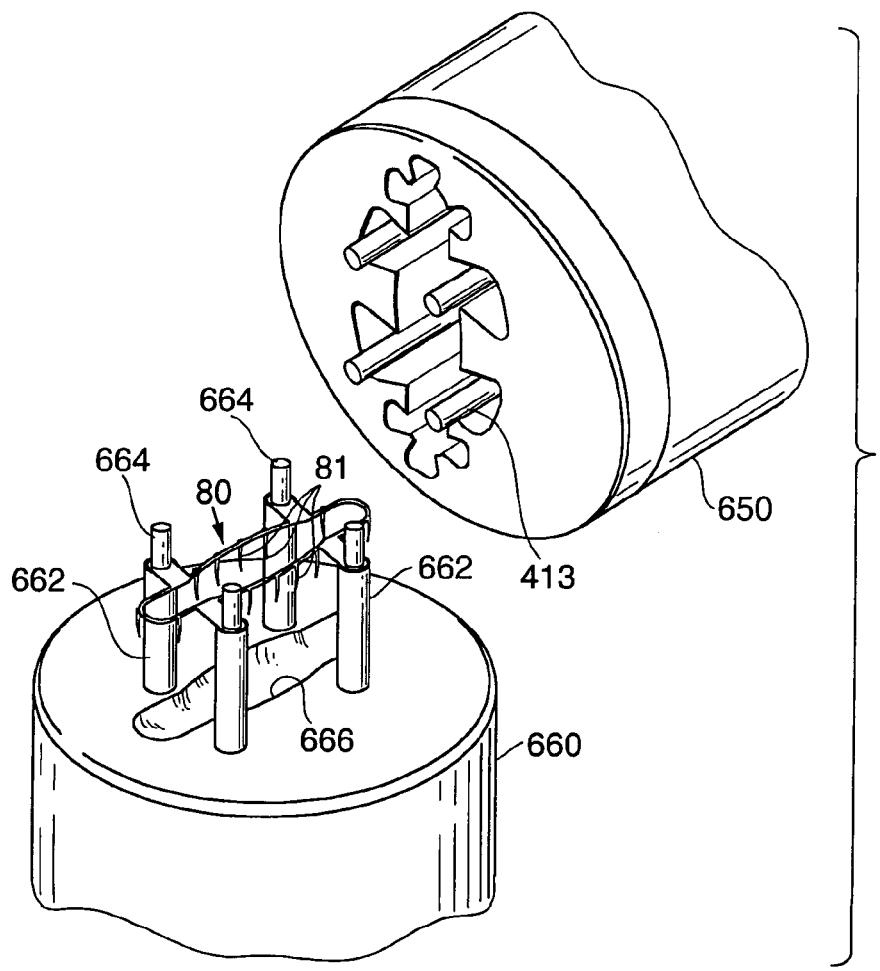

FIG. 66 depicts loading an anastomosis ring into an installation tool using the device of FIG. 65.

Figure 67:
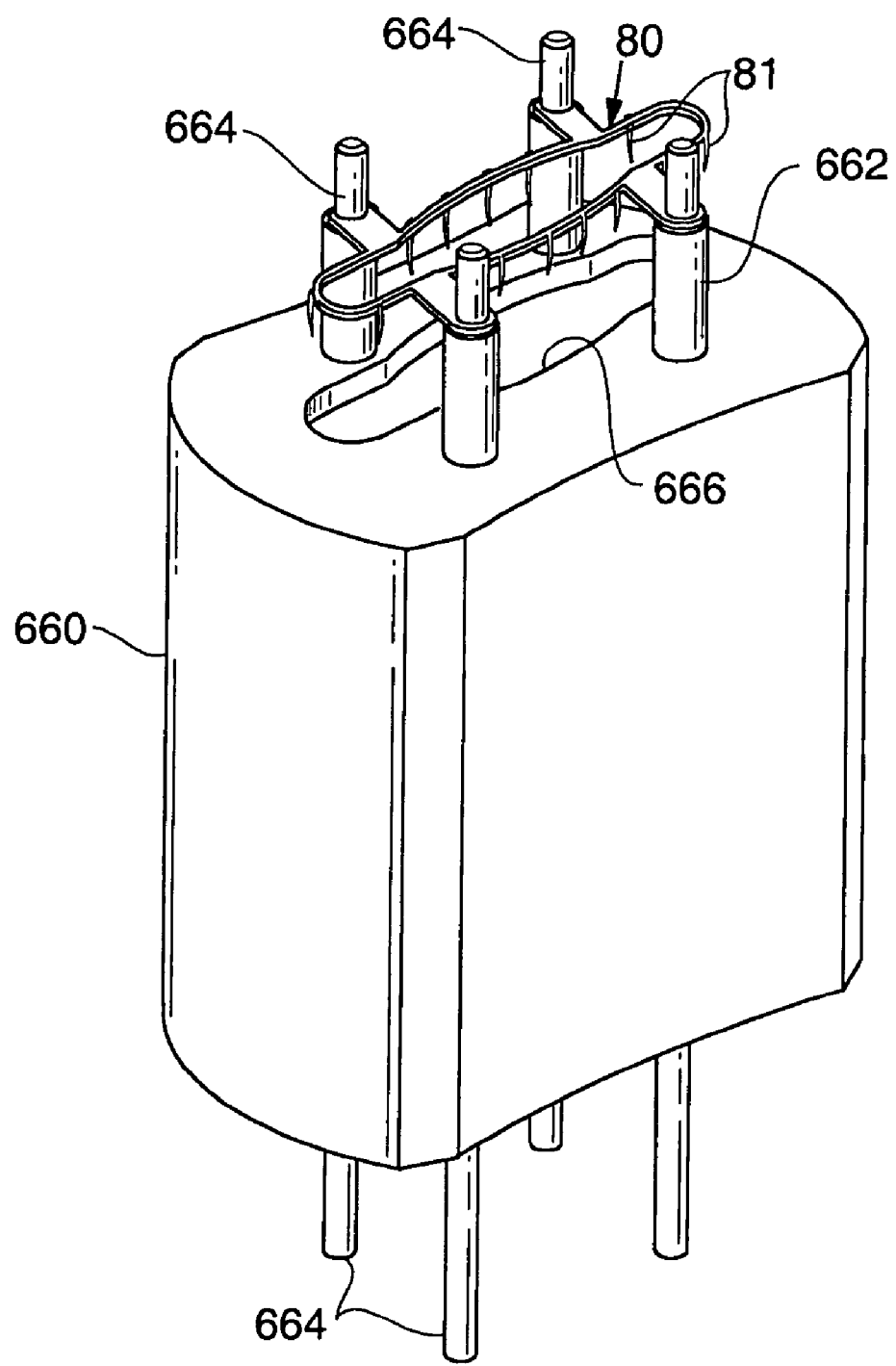

FIG. 67 is a perspective view of the loading device of FIG. 65.

DETAILED DESCRIPTION OF THE PREFERRED EMBODIMENTS

FIG. 5 is a perspective view of an anastomosis ring 50, which is an embodiment of the inventive ring for use in performing anastomosis without hand sutures. Ring 50 is integrally formed from metal, and includes a ring portion 54, and tines 51 and docking arms 52 that extend from ring portion 54. Each docking arm 52 defines a hole 53 (for use in aligning ring 50 with another identical ring, and attaching together the two aligned rings). Ring portion 54 and tines 51 are malleable, but docking arms 52 can be implemented either to be flexible or inflexible.

Other embodiments of the invention (to be described below), have flexible docking arms. In some embodiments of the invention, the flexible docking arms are elastic and in other embodiments they are malleable.

Ring portion 54 and tines 51 of FIG. 5 are "malleable" in the sense that once deformed from a first shape into a second shape they will not relax back into the first shape from the second shape. FIG. 5 shows tines 51 in their initial, straight configuration.

Ring 50 is designed for use without a fabric body (or other hemostatic media) being attached thereto.

To install ring 50 in a vessel (or other organ) with ring portion 54 extending around an incision (or other orifice), tines 51 pierce the tissue around the orifice and are curled against an anvil until tines 51 have the bent configuration shown in FIG. 6. The action of curling the tines inverts the tissue near the orifice edges (by everting the tissue) to expose the inside surface of the vessel or organ (so that such exposed inside surface can be joined to tissue of another vessel or organ).

In typical use, ring 50 is installed (as shown in FIG. 7) at the site of an incision in the side wall of a blood vessel having exterior surface 56 and interior surface (inside lining or "intima") 55. More specifically, the ring is installed with ring portion 54 (not visible in FIG. 7) extending around the incision, and the action of curling the ring's tines during installation everts the incised edges of the orifice to expose the intima 55 of the blood vessel as shown in FIG. 7.

In variations on the FIG. 5 embodiment, the inventive ring has a malleable ring portion and tines (and docking arms that can but need not be flexible), but the ring is not integrally formed from metal. In some variations the ring is assembled from component parts (e.g., metal parts) which are connected together (e.g., by welding). In other variations, the ring is made of material other than metal, but which has the required mechanical properties (e.g., flexibility and/or moldability).

Next (with reference to FIGS. 8-17) we describe a preferred technique for installing ring 50 of FIG. 5 at the site of an incision (incision 11) in the side wall of a blood vessel (vessel 10) having exterior surface 10A (identified in FIGS. 12 and 13), interior surface ("intima") 10B (identified in FIGS. 12 and 13), and incised tissue surfaces 10C at the incision. It is contemplated that this ring installation is one step of a vascular anastomosis, in which vessel 10 is attached to another vessel (e.g., an aorta).

Figure 1:
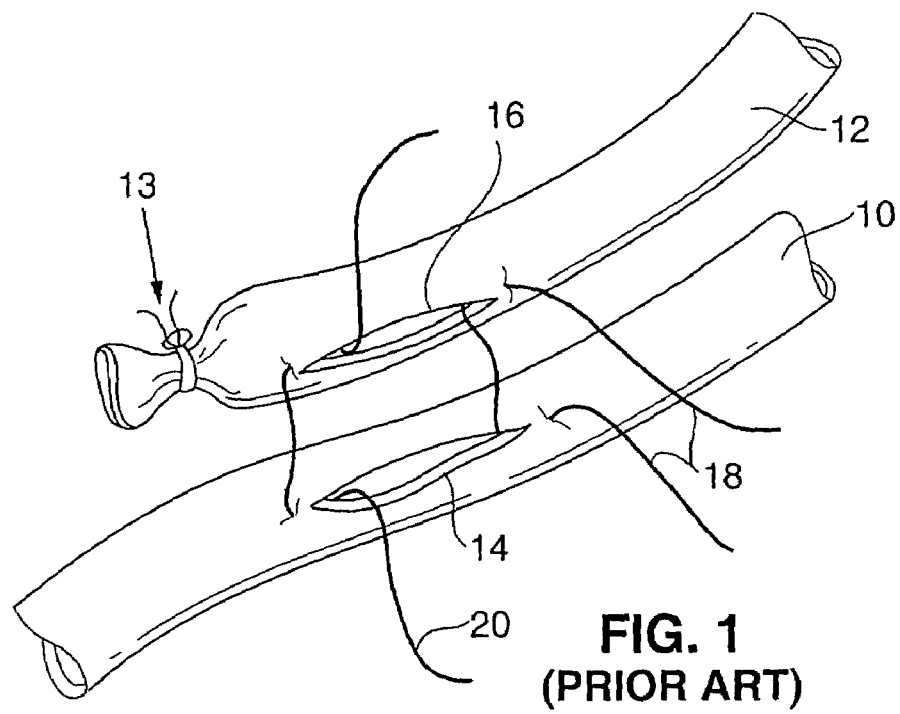
FIG. 1 is a perspective view of a conventional anastomosis using hand sutures to achieve side-to-side connection of two blood vessels.
Figure 2:
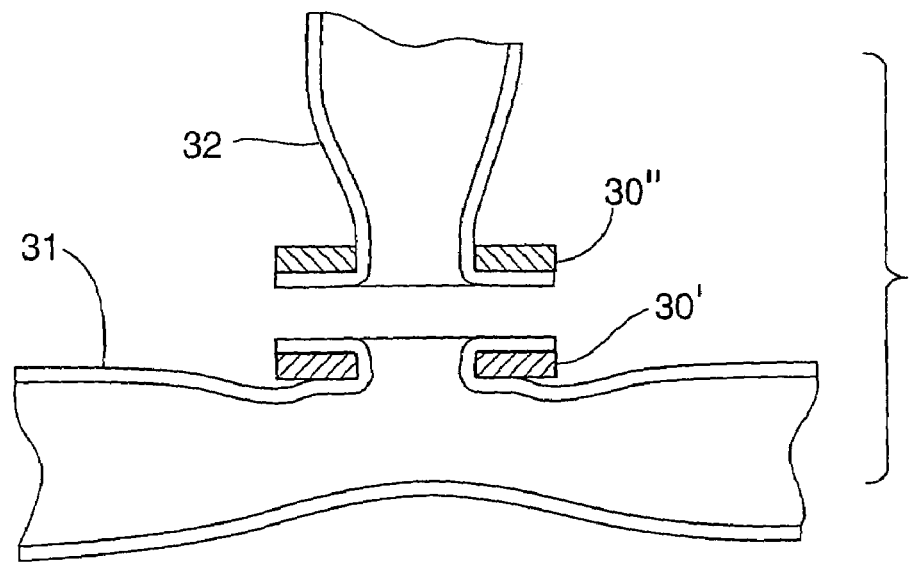
FIG. 2 is a cross-sectional view of a conventional anastomosis using rings to achieve side-to-side connection of blood vessels.
Figure 3:
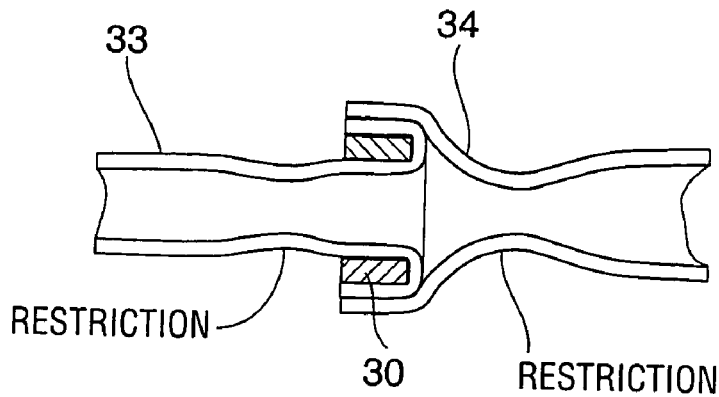
FIG. 3 is a cross-sectional view of a conventional anastomosis using a ring to achieve end-to-end connection of blood vessels.
Figure 4:
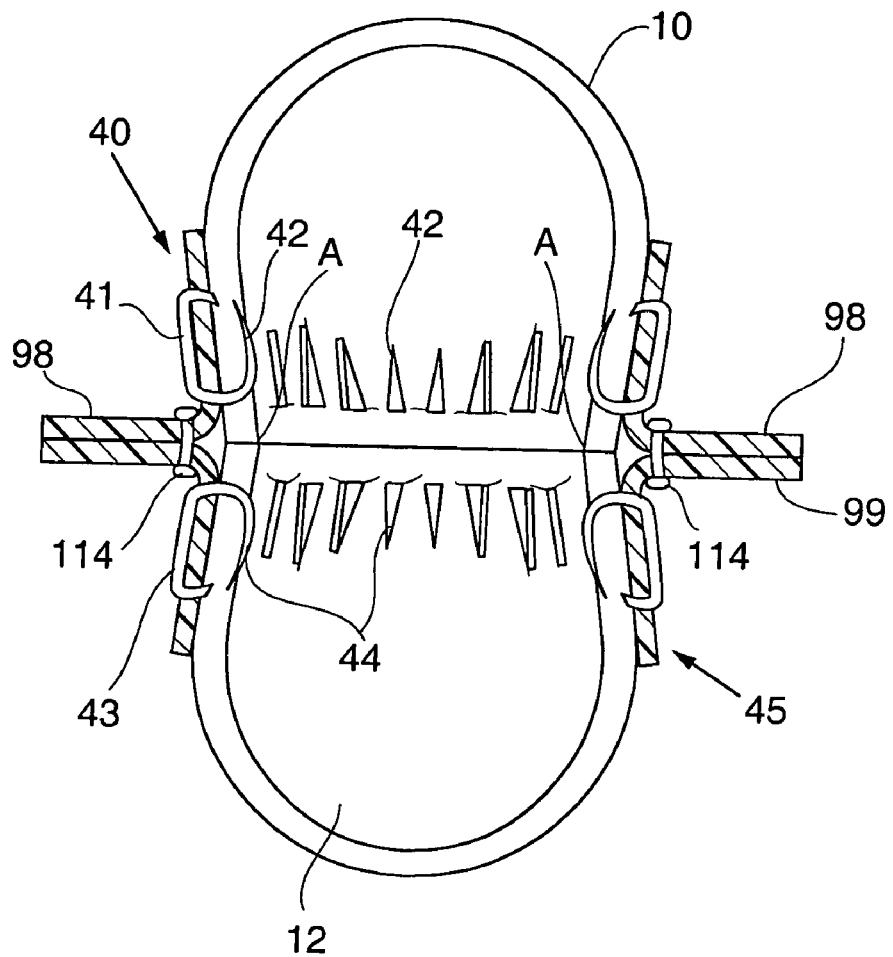
FIG. 4 is a cross-sectional view of an anastomosis using cuff apparatus to achieve side-to-side connection of blood vessels.
Figure 8:
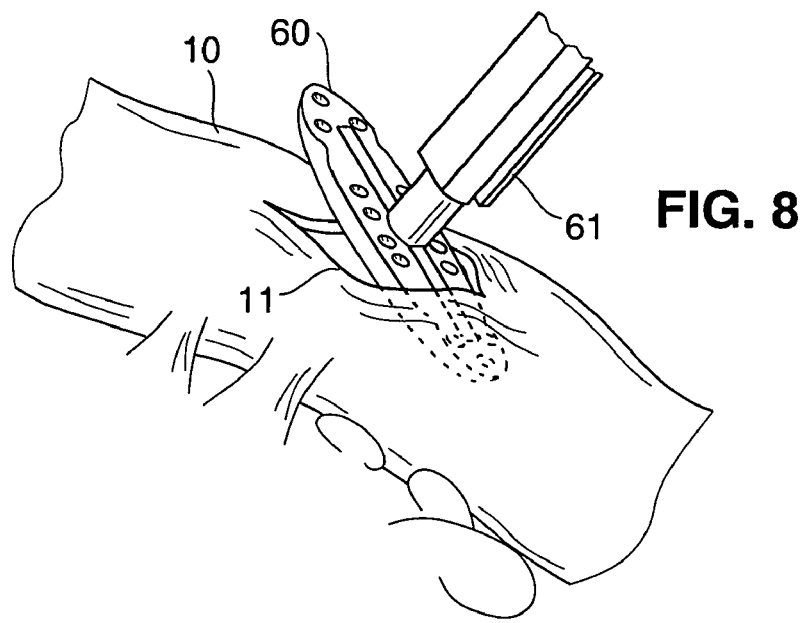
FIG. 8 is a perspective view of an embodiment of the inventive anvil being inserted into an incision in a blood vessel.

As shown in FIG. 8, the first step is to make a small, longitudinal incision 11 (approximately 1.5 mm to 2 mm in length) in the side wall of vessel 10. Then, a ring installation instrument (whose distal portion 59 is identified in FIGS. 9 and 10) is used to lengthen the incision and to install ring 50 in the lengthened incision. Preferred implementations of the ring installation instrument will be described with reference to FIGS. 42-48.

The ring installation instrument includes metal anvil 60, anvil stem 61 which supports anvil 60, driver 63 for lowering ring 50 (so that its tines 51 engage vessel 10 and then curl against the anvil) and then retracting away from the incision site, incision lengthening blade 62 (and means for lowering and raising blade 62 relative to the anvil). In the embodiments discussed below with reference to FIGS. 42-54, elements 422 and 424 correspond to driver 63 and blades 426 correspond to blade 62.

Figure 9:
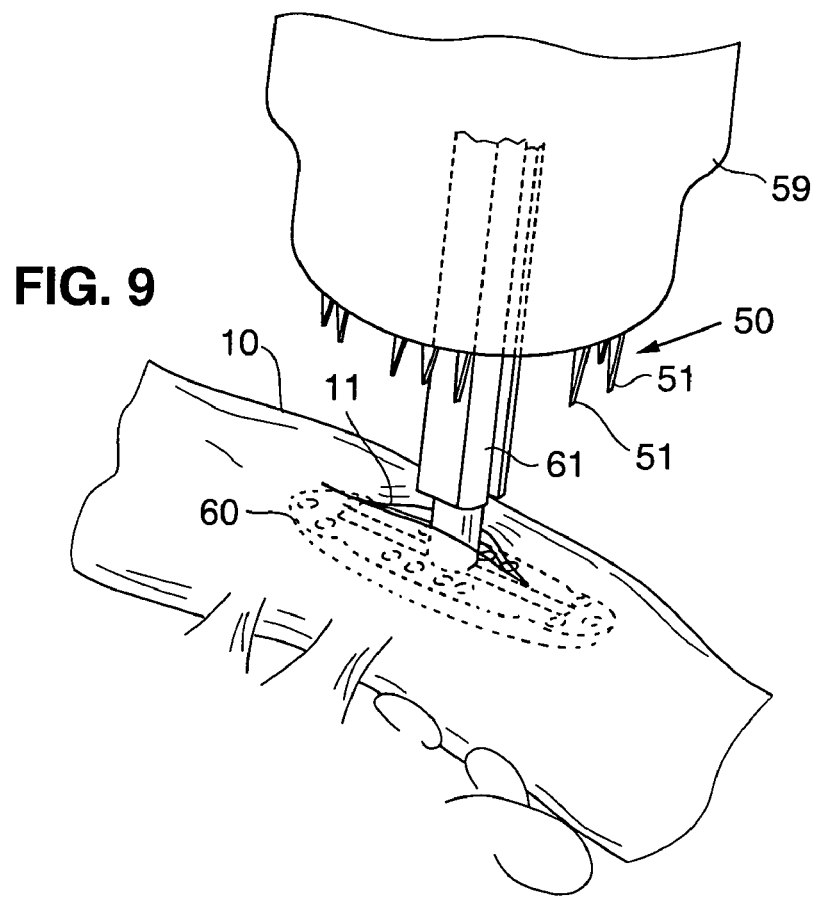
FIG. 9 is a perspective view of the anvil of FIG. 8 fully inserted into the incision, with an embodiment of the inventive ring being lowered into engagement with the tissue around the incision.

As shown in FIGS. 8 and 9, anvil 60 is placed within vessel 10 by manipulating stem 61 to place one end of the anvil through incision 11, then rotate the opposite end of the anvil through the incision until the entire anvil 60 is within the lumen of vessel 10. The anvil 60 is then centered in the incision 11 by locating stem 61 at or near the center of the incision.

Then, as shown in FIG. 9, the ring installation instrument is manipulated to approximate clip 50 to the vessel (bring clip 50 into contact with the vessel) while anvil 60 is locked relative to the rest of the installation instrument (e.g., using an anvil retraction trigger such as trigger 406 discussed below with reference to FIGS. 42 and 48) and anvil 60 is kept centered in incision 11. The installation instrument is then operated (e.g., in response to pulling a trigger such as trigger 400 of FIG. 42) to lower ring 50 until its tines 51 engage the surface of vessel 10, and then until tines 51 penetrate through the vessel tissue until the tips of the tines engage corresponding depressions in the upper surface of anvil 60.

The installation instrument then continues to operate (e.g., still in response to the prior trigger pull) to translate the incision lengthening blade 62 downward through the central orifice of ring 50 (into engagement with vessel 10, such that blade 62 is aligned with incision 11) until blade 62 extends the incision 11 (thereby forming an extended incision of precisely known overall length, which is slightly shorter than the length of ring 50's central orifice).

Figure 10:
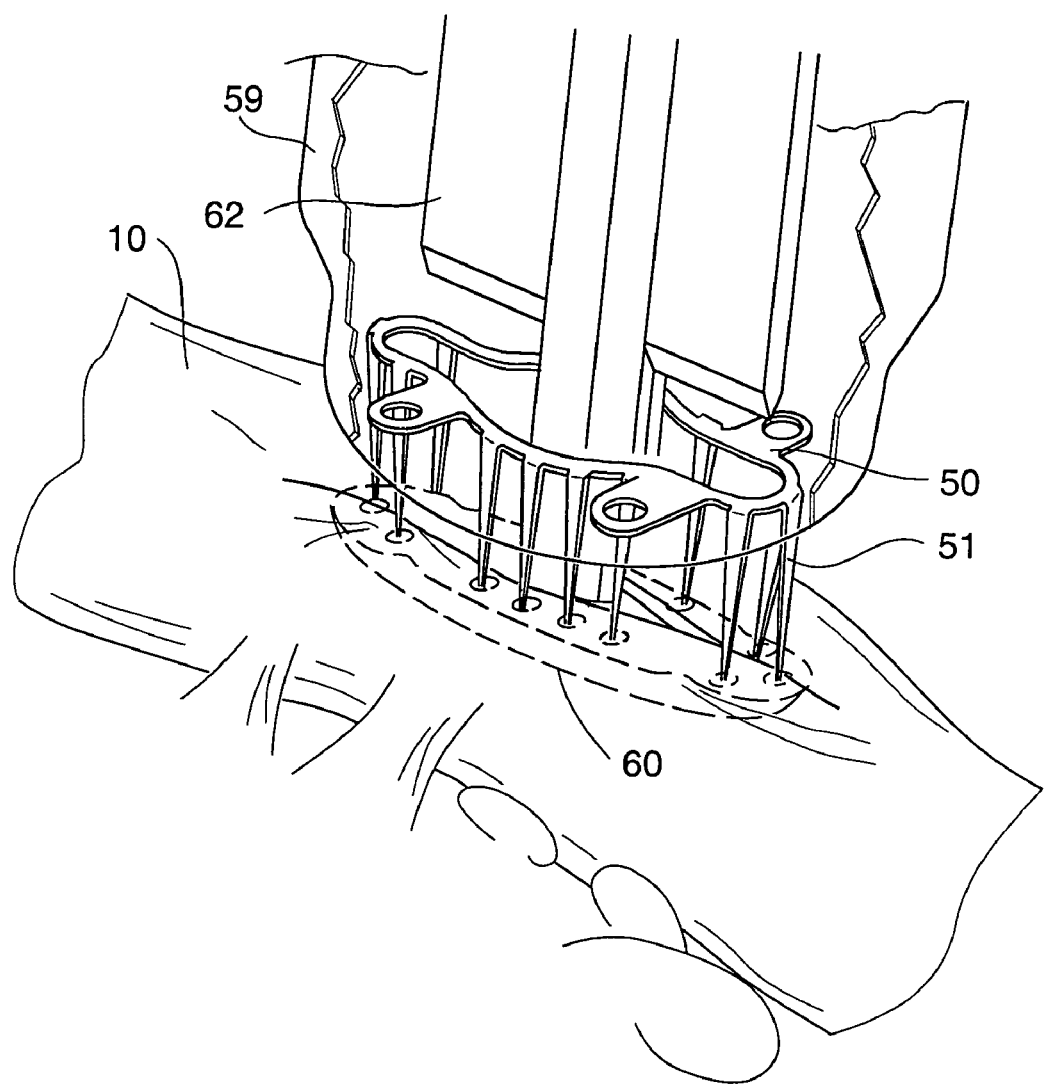
FIG. 10 is a perspective view of the anvil and ring of FIG. 9 in engagement with the tissue around the incision, with the incision-lengthening blade of the installing apparatus retracting from the vessel after having lengthened the incision.

Then, blade 62 is retracted, until it rises out of engagement with the vessel and above ring 50 (into the position shown in FIG. 10).

Figure 11:
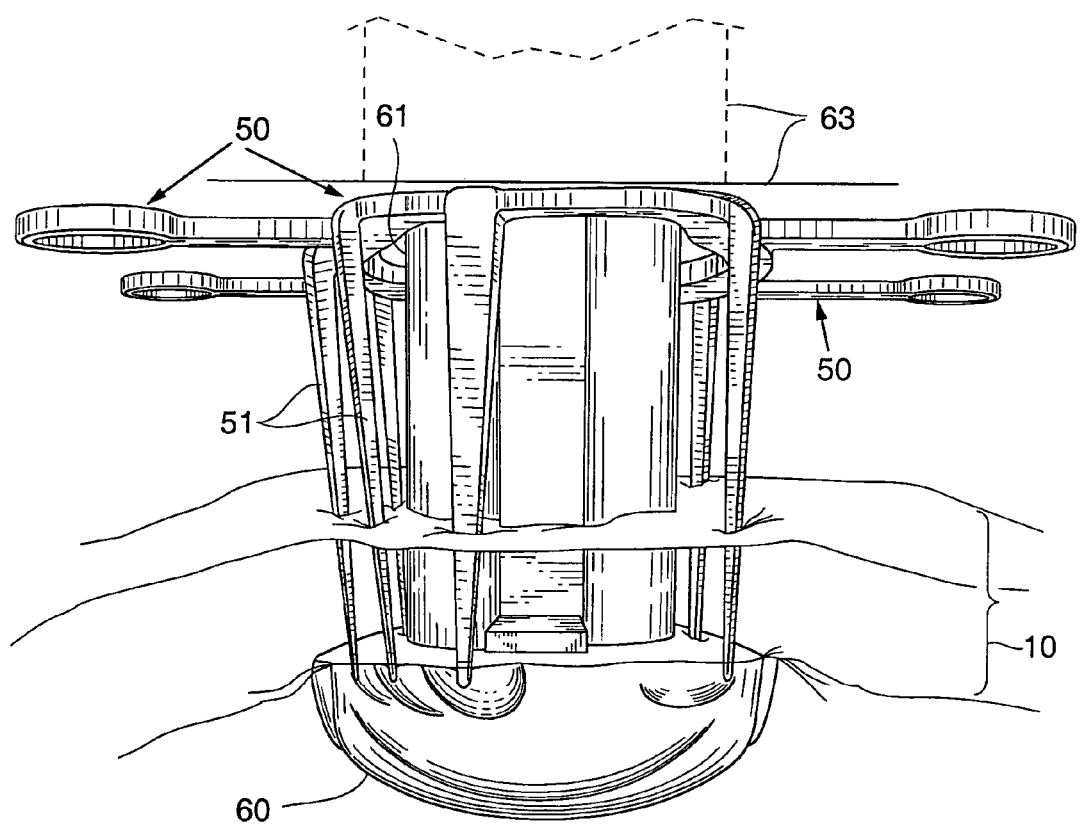
FIG. 11 is a perspective view of the anvil and ring of FIG. 10, viewed from a point along the axis of the incision.

The installation instrument then continues to operate (e.g., still in response to the initial trigger pull) to move a driver 63 (sometimes referred to as a hammer) downward into engagement with ring 50, so as to push ring 50 downward against the anvil 60. FIG. 11 shows driver 63 (shown schematically) engaged with ring 50. As driver 63 pushes ring 50 downward against anvil 60, the tines Curl against anvil 60, as shown in FIGS. 12-15. The action of curling tines 51 inverts the tissue near the incision edges 10C (by everting the tissue) to expose the inside surface 10B of the vessel (so that the exposed inside surface can be joined to tissue of another vessel).

Figure 12:
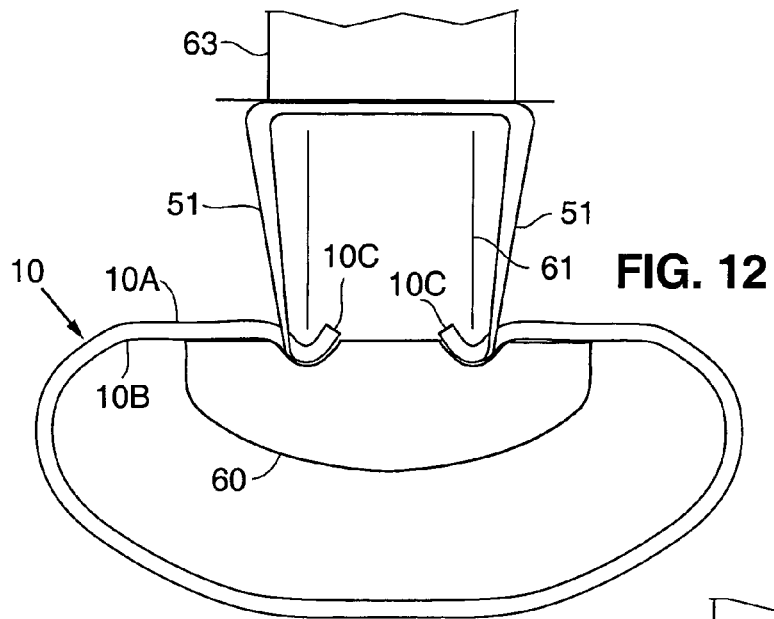
FIG. 12 is a cross-sectional view of the tines of the ring of FIG. 11, with the driver of the installing apparatus pushing the tips of the tines against the anvil.
Figure 13:
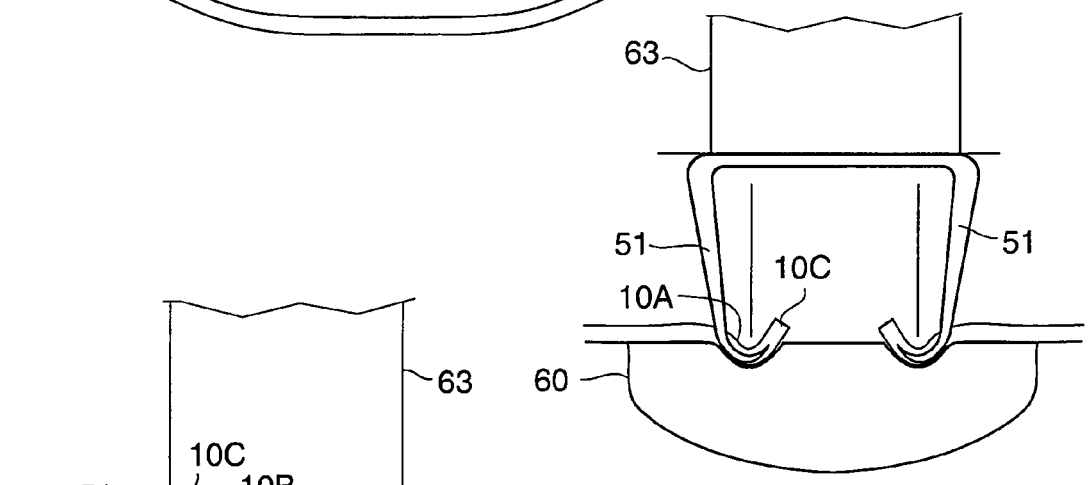
FIG. 13 is a cross-sectional view of the FIG. 12 apparatus after the driver has pushed the tines further downward against the anvil.
Figure 14:
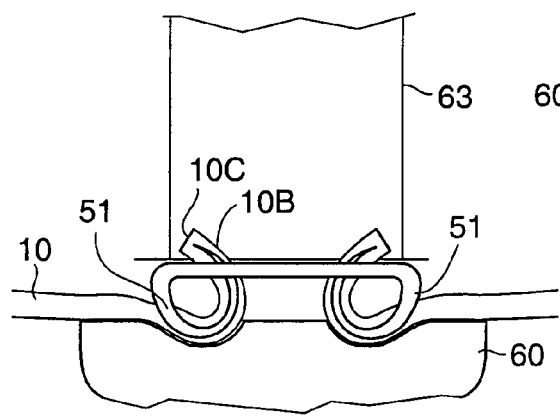
FIG. 14 is a cross-sectional view of the FIG. 13 apparatus after the driver has pushed the tines still further downward against the anvil (showing that eversion of the tissue along the incision has begun).
Figure 15:
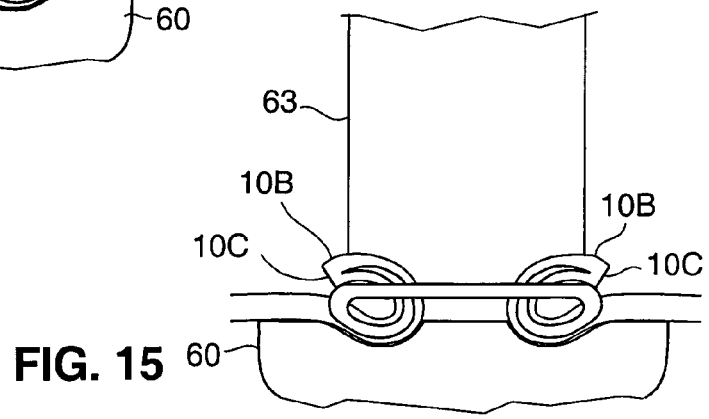
FIG. 15 is a cross-sectional view of the FIG. 14 apparatus, with the driver in its fully extended position which has caused the tines to curl into their fully bent configuration (showing full eversion of the tissue along the incision).

As tines 51 curl from their position shown in FIG. 12 to that shown in FIG. 13, then to the position shown in FIG. 14, and finally to the position shown in FIG. 15, the incised tissue edges 10C and the exterior tissue surface 10B adjacent to them become inverted under newly exposed interior tissue (intima) 10B. After this occurs, driver 63 is retracted out of engagement with the vessel and ring 50, and (preferably also) ring 50 is then manipulated to spread open the central orifice through ring 50 (thereby widening the corresponding orifice in the vessel at the incision site, e.g., into the state shown in FIG. 16). Preferably, the anvil is driven distally (a small distance) relative to the installation instrument and ring following curling of the tines and prior to spreading of the central orifice through the ring.

Figure 16:
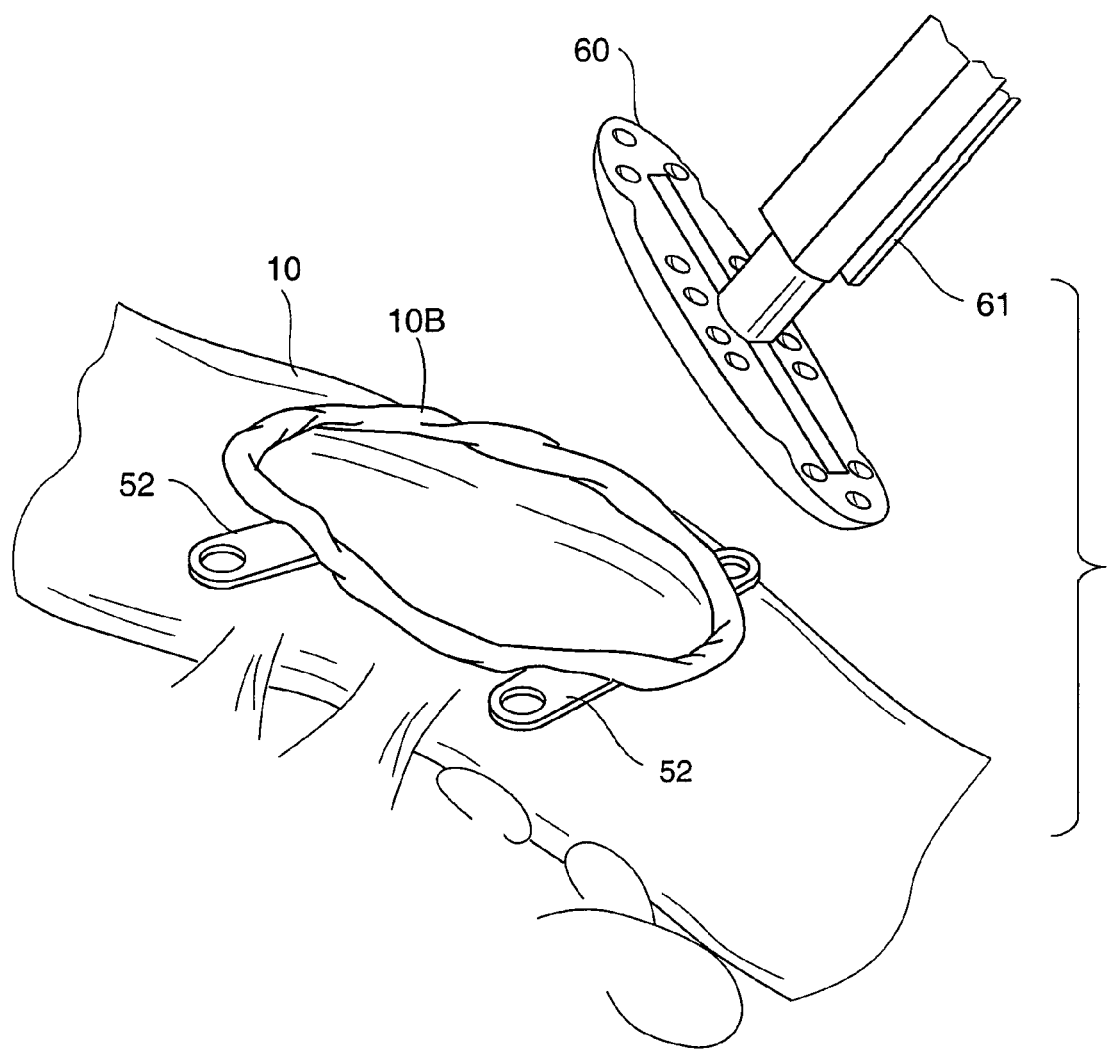
FIG. 16 is a perspective view of the FIG. 15 apparatus, after the driver as been retracted from the vessel and the anvil removed from within the vessel (showing the ring installed in the vessel, with vessel intima 10B exposed).

Finally (preferably in completion of an operating cycle of the installation instrument in response to a single trigger pull), the installation instrument releases anvil stem 61, and the installation instrument (minus stem 61 and anvil 60) is removed from the vessel environment. Stem 61 is then manipulated to remove anvil 60 from the vessel through the spread-open ring 50 (by sliding stem 61 to one end of the ring, rotating the anvil up so that one end passes through the ring, and then removing the rest of the anvil). FIG. 16 shows ring 50 installed in the vessel with docking arms 52 exposed, and with vessel intima 10B exposed.

The artery may bleed after removal of the anvil, and so it may be necessary (in some cases) to apply a cap (or sponge) over the installed ring until the ring is to be aligned with and joined to a second ring (to complete an anastomosis).

Typically, the procedure is repeated to install another ring (which is identical to ring 50) in an incision in the side wall of a second vessel (to be joined to vessel 10). Then using alignment ("docking") forceps which grip the docking arms of the rings, one ring is placed directly on top of the other ring so that the exposed intima of the two vessels engage each other in intimate contact (guide wires temporarily connected through holes 53 of docking arms 52 can be used to guide one ring into alignment with the other ring). Then, a fastening instrument is used to attach together the two sets of aligned docking arms (the docking arms of one ring and the docking arms of the other ring) to form the anastomosis. The intima of the two joined vessels will eventually heal together, while the aligned incisions remain open to allow blood flow from one vessel to the other.

Figure 17:
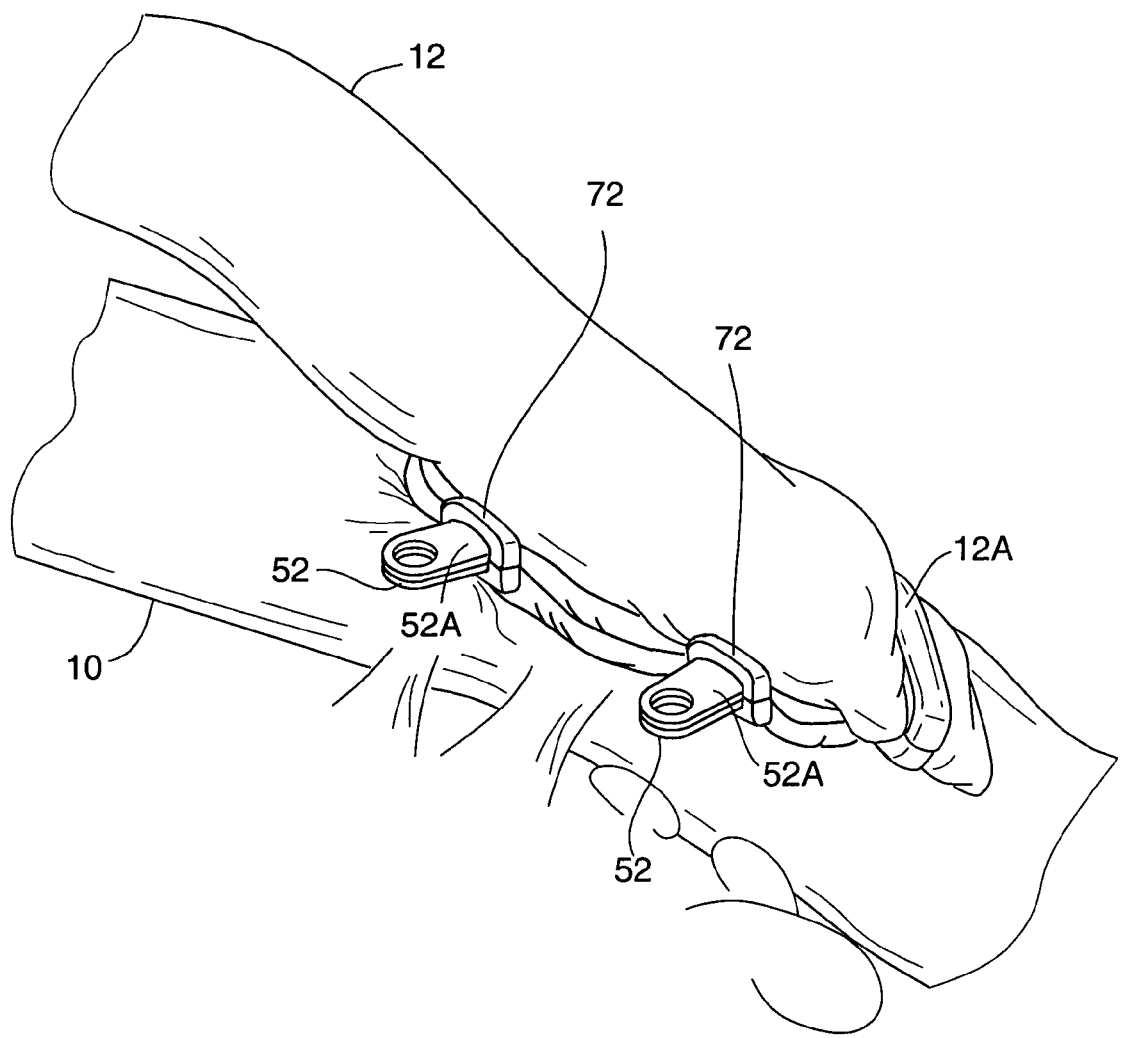
FIG. 17 is a perspective view of a completed anastomosis, in which the vessel (with installed ring) of FIG. 16 has been joined to a second vessel (also having one of the inventive rings installed therein).

In the completed anastomosis shown in FIG. 17, one ring (having docking arms 52) is installed in vessel 10, and the docking arms 52A of an identical ring (installed in vessel 12) are aligned together, and fastened together by crimping fasteners 72 around both sets of docking arms. Vessel 12 is a graft vessel having a first end that is closed (e.g., by fastener 12A which is a hemostatic clip, or by sutures). It is contemplated that the other end of vessel 12 can be joined to a third vessel using the same apparatus (and essentially the same procedure) used to produce the FIG. 17 anastomosis.

For example, rings can be pre-installed at both ends of the graft vessel. Then, a third ring can be installed in an incision in a coronary artery, and an anastomosis performed to connect the distal end of the graft vessel to the coronary artery. Then, a fourth ring can be installed in an incision punched in the aorta (and the aorta cross-clamped, or a stopper applied in the incision, as necessary). The heart can be beating or arrested during installation of the fourth ring. Then another anastomosis is performed to connect the proximal end of the graft vessel to the aorta. The installed fourth (aortic) ring will typically need to be capped or covered (to prevent bleeding from the aorta) until the graft vessel and aortic rings are docked.

Figure 18:
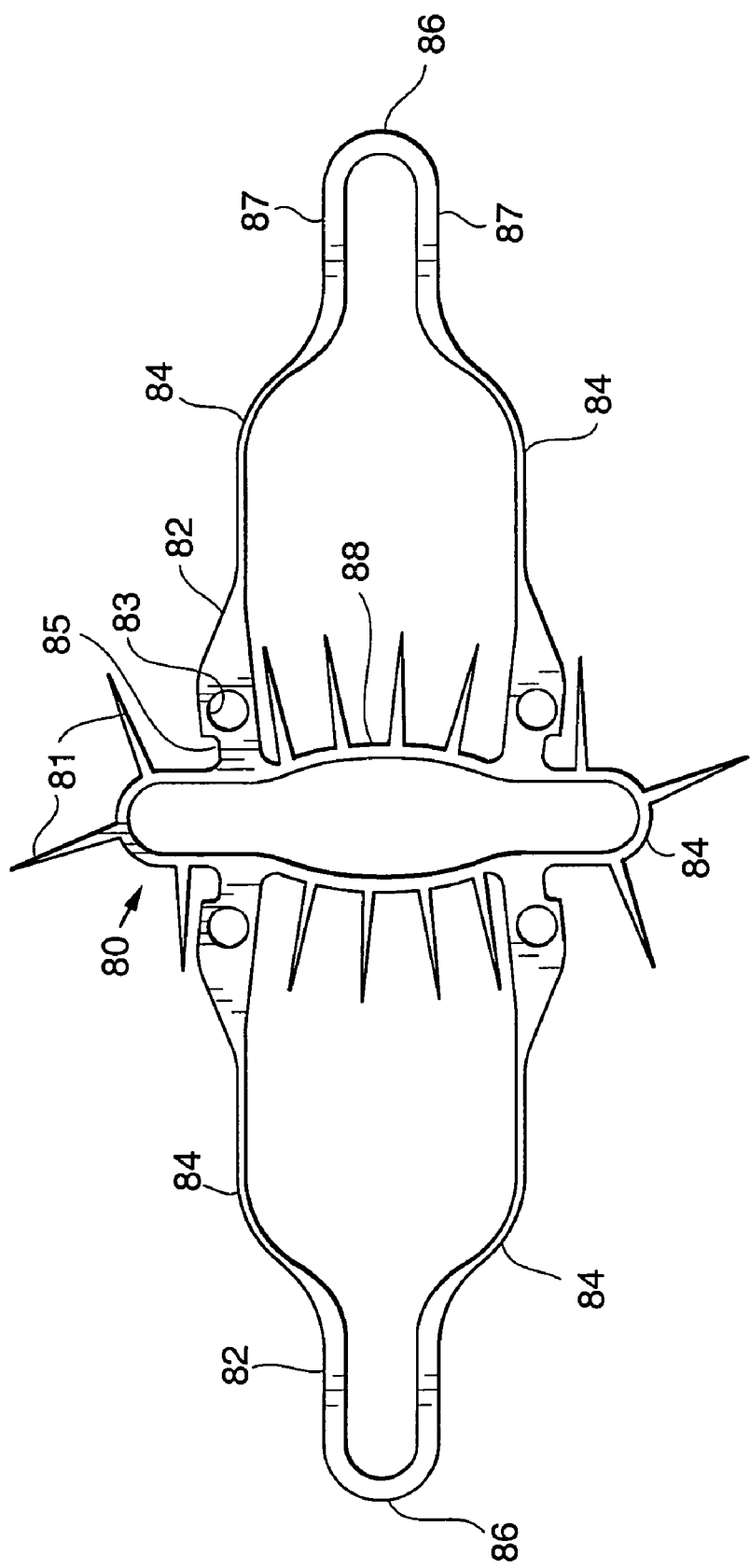
FIG. 18 is a top elevational view of a preferred embodiment of the inventive ring.

FIG. 18 is a top elevational view of an anastomosis ring 80 which is a preferred embodiment of the inventive ring for use in performing anastomosis without hand Sutures, and which can be used in place of above-described ring 50. Ring 80 is integrally formed from metal (preferably stainless steel), and includes a ring portion 88, and tines 81 and docking arms 82 that extend from ring portion 88. Each docking arm 82 defines a pair of holes 83 (for use in holding ring 80 during installation, and for aligning an installed ring 80 with another identical ring such as by stringing suture material through holes 83 to guide one ring to the other, and/or attaching together the two aligned rings). Ring portion 88, tines 81, and arms 82 are malleable. Ring 80 is shown in the flat configuration in which it will typically be manufactured. Before use, tines 81 would be bent (each about its line of attachment to ring portion 88) by ninety degrees (out of the plane of FIG. 18) relative to the rest of ring 80.

Each arm 82 has very thin cross section, especially at thin portions 84, so as to have good flexibility, and thus to aid in handling of ring 80, and also in alignment of two rings 80 and fastening together of two such aligned rings 80. The arms 82 are designed to deform plastically with very light force during spreading of ring portion 88 (when the ring is installed at an anastomosis site), and when the ends 86 of arms 82 are pulled away from each other with gentle force by docking forceps (during handling and alignment of two installed rings 80). The term "docking" is used herein to denote alignment, in the sense that two installed rings are docked when they are moved into alignment with each other.

The end portion 87 of each arm 82 (near end 86) is made of thicker material than are the thin portions 84, since such reinforcement of the end portions aids in the accuracy with which two rings 80 can be angularly aligned during docking.

The shape of the docking arms 82 allows convenient alignment and attachment together of two of rings 80 (each installed in a different vessel) at the anastomosis site, using docking forceps (e.g., forceps 90 shown in FIGS. 19 and 20 or forceps 221 of tool 220 shown in FIG. 36) and spring clips (e.g., spring clips shown in FIGS. 26 and 30) or crimp clips (e.g., any of the clips shown in FIGS. 22-25). Notches 85 are configured to snag side loops of a spring clip while the spring clip is sprung around two of rings 80 (that have previously aligned with each other) so that the spring clip clamps the rings together.

The barbs adjacent to notches 85 are useful when crimp clips (e.g., those of FIGS. 22-25C, or variations thereon) are employed. When a crimp clip (e.g., one shaped like a ligating clip) has been coated with (or molded into) silicone or another elastomeric material, and the clip is crimped around aligned docking arms, some silicone (or other elastomeric material) will be squeezed so as to fill around the barbs and thus be retained onto the docking arms. The barbs can be bent to further increase their interference with the silicone. Also, the silicone that is squeezed into holes 83 will provide some holding strength. Of course, this functionality will be provided by barbs protruding from, and holes in, variations on (and alternative embodiments of) ring 80 of FIG. 18.

Figure 20:
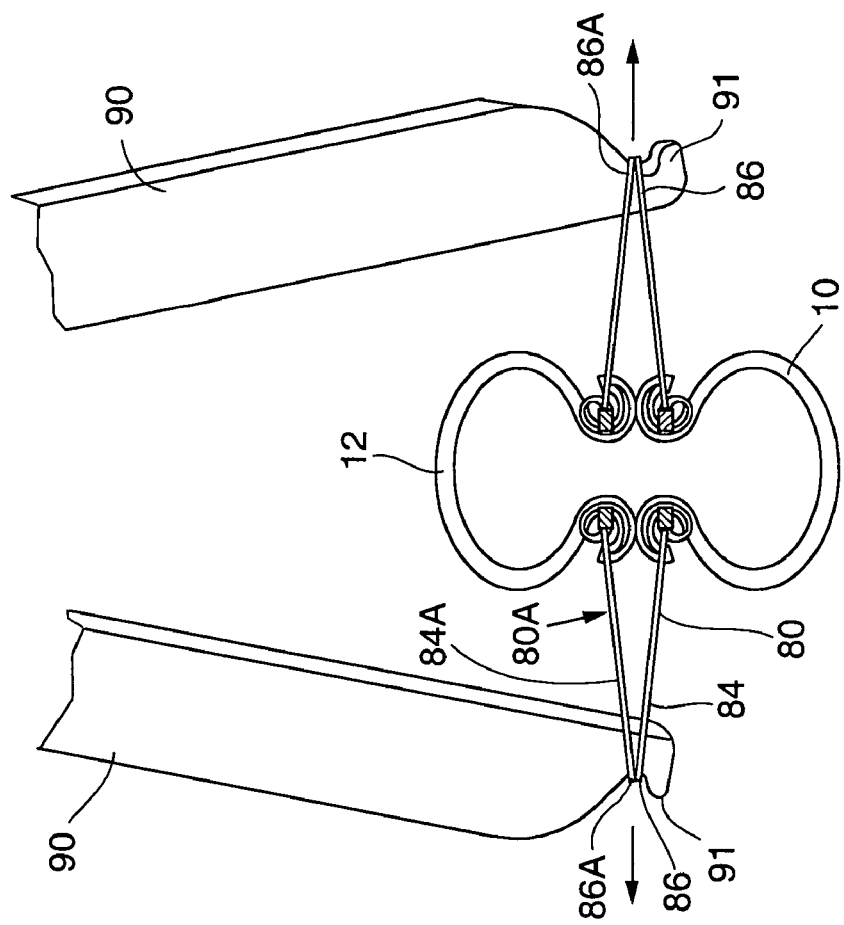
FIG. 20 is a perspective view of the rings of FIG. 19 after they have been precisely aligned.
Figure 19:
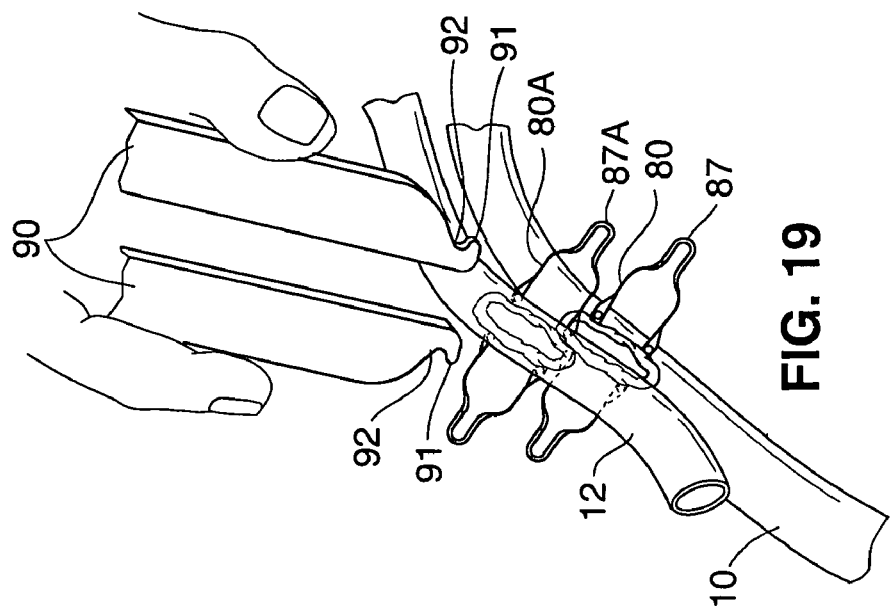
FIG. 19 is a perspective view of the manner in which two rings (of the FIG. 18 type), each installed in a different vessel and roughly aligned, can be aligned precisely with each other in accordance with the invention.

We next describe this process with reference to FIGS. 19 and 20, which show one ring 80 (having central portions 84, end portions 87, and ends 86) installed in an orifice in bottom vessel 10 and an identical ring 80A (having central portions 84A, end portions 87A, and ends 86A) installed in an orifice in top vessel 12. The outer surface of each arm of forceps 90 defines an end hook 91, and a notch 92 between the end hook 91 and the rest of the forceps. The docking arms of ring 80 have an indented profile with widely separated central thin portions 84 and narrower end portions 87. During docking, the arms of forceps 90 are squeezed slightly together (as shown in FIG. 19) and notches 92 are inserted between the thin portions 84 and 84A of roughly aligned rings 80 and 80A (or forceps 90 can move ring 80A into rough alignment with ring 80 while hooks 91 engage ends 86A of ring 80A, and then the forceps arms can be slightly squeezed together while notches 92 are inserted between the thin portions 84 and 84A of roughly aligned rings 80 and 80A). Then, the arms of forceps 90 are released, to allow them to relax back to their separated state while their outer surfaces move outward into engagement with end portions 87 of ring 80 and end portions 87A of ring 80A (which guide the outer surfaces of the forceps outward to ends 86 and 86A). After the outer surfaces of forceps 90 engage ends 86 and 86A, the spring force exerted by the forceps (the force causing the arms of the forceps to relax into their separated state) causes notches 92 to slide upward and outward along end portions 86 and 86A until end hooks 91 engage end portions 86 and 86A (as shown in FIG. 20). The spring force exerted by hooks 91 on ends 86 and 86A accurately aligns rings 80 and 80A horizontally, vertically, and angularly (about a vertical axis).

The tapered profile of portions 84 provides a lead in for applying a fastener, and also provides stress relief between end portions 87 (which are thick enough to be semi-stiff or rigid) and the thinnest (flexible) part of each portion 84.

Notch 92 has a distal portion (nearer to hook 91) and a proximal portion (farther from hook 91). In the FIG. 19 embodiment, the proximal portion of notch 92 (on each arm of forceps 90) defines an overhang surface which allows for an aggressive snatch (grab) of two roughly aligned docking arms, while preventing the docking arms from sliding (in the proximal direction) up the sides of forceps 90 beyond notch 92.

A photo etching process is preferably used to manufacture ring 80. First, the ring profile is etched from the raw material in its full thickness. Next, a second pass is done to photo etch away approximately ½ thousandth inch of material from the individual tines. This process yields tines with rounded edges (which is important for penetrating through tissue without opening Lip leak paths around the tines) and allows for lowered firing force due to the thinness of the tines (which allows them to curl more easily against the anvil). Alternatively, a simple dunk in an electropolish tank replaces the second photo etch pass. The electropolishing process removes material from all surfaces of the ring, thus rounding the tine edges, but it yields a ring whose tines have the same thickness as the rest of the ring. Ring 80 is preferably made to have 2 mm size (for use in accomplishing distal site anastomosis of blood vessels), or 3 mm size (for use in accomplishing proximal site anastomosis of a graft vessel to an aorta).

In alternative embodiments, ring 80 is formed such that docking arms 82 are not flexible. Other alternative embodiments are variations on ring 80 having large docking arms (or other large features, which can be flexible or inflexible) extending outward from their central ring portion, where the large docking arms (or other large features) are shaped for engagement by docking forceps so that the docking forceps can readily and accurately align together two rings (where the rings have typically been roughly aligned prior to engagement by the forceps).

When two of the inventive rings have been aligned at an anastomosis site (e.g., when rings 80 and 80A have been aligned as in FIG. 20), and while their two pairs of aligned docking arms continue to be pulled outward by docking forceps, fasteners are applied (one on each side of the aligned rings) to connect together the aligned rings. Typically, an instrument (such as ring alignment and fastener application tool 95 shown in FIG. 21, or tool 220 shown in FIG. 36) is used to apply the fasteners.

With reference to FIG. 21, ring alignment and fastener application tool 95 has an overall gun-like shape, including a handle 96 and a trigger 97. The user squeezes the trigger 97 to actuate a mechanism which applies fasteners to docking features on both sides of a pair of aligned anastomosis rings. Tool 95 includes forceps 90 (previously described), which are used in the above-described manner to align two rings, and to maintain in a spread configuration the aligned docking features (e.g., docking arms) of the rings. The aligned docking features can be maintained in their spread configuration using spring biasing force that is produced by spring 90A of forceps 90 (which tends to spread apart the hooks 91 of the forceps), or by holding the aligned docking features in the desired configuration using a mechanical stop which fixes forceps 90 (so that the distance between the innermost edges of the forceps behind hooks 91 is the maximum allowable end-to end length of the aligned rings' docking features). The tolerance in the mechanical stop distance can be accommodated by flexibility of the docking features and the tolerance in the degree of accuracy with which the rings must be centered relative to the forceps hooks.

Tool 95 includes two clip carriages 98, each of which holds a fastener clip and is movable between a retracted position (the position shown in FIG. 21) to an extended position in which the clip engages (or nearly engages) a docking feature of the aligned rings. When carriages 98 have reached their extended positions, the clips are fastened to the rings.

In a class of implementations, each clip carriage 98 has a translatable hammer (e.g., hammer 99 shown in FIG. 22) associated therewith. Preferably, in response to actuation of trigger 97, each hammer moves with the associated clip carriage from the retracted carriage position to the extended carriage position while the hammer is pre-loaded against a clip held by the carriage (e.g., a clip that has been dispensed from within the carriage). Then, when the carriage reaches the extended position, the hammer fires to crimp the clip around aligned docking features of two anastomosis rings. Then, to complete the operating cycle in response to a trigger actuation, a new clip is dispensed from within the carriage, the new clip is pre-loaded in appropriate orientation by the hammer, and the hammer and carriage retract together as a unit from the extended position of the carriage to the retracted position of the carriage.

Alternatively, the carriages preposition the clips in their final positions, the hammers then fire (and retract) to crimp the clips around aligned docking features of two anastomosis rings, and the carriages then retract.

In preferred embodiments, each clip carriage 98 is moveable from the retracted position shown in FIG. 21 to a position at which it provides a fastener clip at the correct location relative to the aligned anastomosis rings (e.g., each fastener clip is translatable distally from the initial position to an extended position that is a predetermined distance D beyond the distal end of carriage 98). Movement of the carriage by such distance D can be accomplished using a mechanical linkage or joint (which may include, for example, pins, grooves, and/or slots) between the distal end of carriage 98 and the distal end of the corresponding arm of forceps 90, or by the two carriages 98 being connected together (or coming together) and being centered between the arms of forceps 90 by mechanical linkages and joints, or via both methods (with one being more dominant than the other depending on tolerances).

In variations on tool 95 of FIG. 21, only a single clip carriage is used. The clip carriage is movable to position one fastener clip in the correct extended position using a mechanical linkage or joint between the distal end of the carriage and the distal end of the corresponding forceps arm, or by a linkage between the carriage and tool 95. A hammer then crimps the clip around the aligned anastomosis rings (or the tool otherwise attaches the clip to the aligned anastomosis rings). Use of a single clip carriage (rather than two as in FIG. 21) has the disadvantage that the carriage must be used twice per pair of docking features to be connected. However, it has the advantages of allowing a more streamlined and simpler overall apparatus, and offering the user greater versatility (i.e., the ability to remove and reapply one fastener clip rather than two, if a fastener clip application operation fails for any reason).

With reference to FIG. 22, tool 95 preferably includes a translatable hammer 99 for each clip carriage 98. Each hammer 99 translates distally together as a unit with clip carriage 98 in response to actuation of trigger 97 while the hammer is pre-loaded against a fastener clip (e.g., clip 100) as shown in FIG. 22, and the hammer then fires relative to the carriage and clip to crimp fastener clip 100 (which is being held by carriage 98 in the proper position around aligned docking features of two anastomosis rings) to fasten the clip 100 onto the aligned anastomosis rings. Hammer 99 crimps the clip 100 by pressing it against bottom ledge 98A of clip carriage 98.

Clip 100 of FIG. 22 has its cross bar 101 oriented so that carriage 98 (with clip 100 held against element 98A of carriage 98) can be translated distally toward the rings and then horizontally or substantially horizontally (at least roughly in the plane of the aligned docking features) into the proper final position prior to crimping. Then, as hammer 99 pushes the top arm of clip 100 downward, the clip's top arm rotates downward until its tip contacts the tip of the clip's lower arm (which remains fixed against element 98A). Then, as hammer 99 continues to push down on clip 100, cross bar 101 is crushed at its midpoint and is stretched at areas near its midpoint. Thus, a spring force is generated between the tips of the clip's upper and lower arms. When the hammer is retracted from the crimped clip 100, the residual spring force can hold together the aligned docking features (which are clamped between the upper and lower arms of clip 100).

Figure 23:
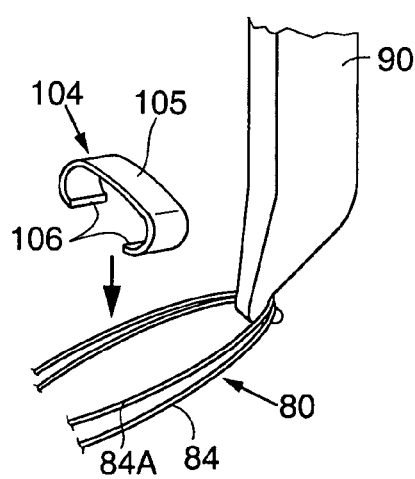
FIG. 23 is a perspective view of a detail of another implementation of the FIG. 21 apparatus, in which the apparatus functions to crimp another type of fastener clip around one set of aligned docking features.

In embodiments in which a fastener clip is held by the clip carriage with the clip's crossbar oriented toward the top (as fastener clip 104 of FIG. 23 is oriented with its crossbar 105 on top), the clip carriage should move the fastener clip downward (perpendicular to the plane of the aligned docking features) into its final position. With reference to FIG. 23 for example, the clip carriage (not shown in FIG. 23) would move clip 104 downward until the free ends 106 of the clip straddle the central portions (84 and 84A) of aligned docking arms of rings 80 and 80A. During the operation of positioning and fastening fastener clip 104, the clip 104 will always stay between the two arms of forceps 90.

Figure 24:
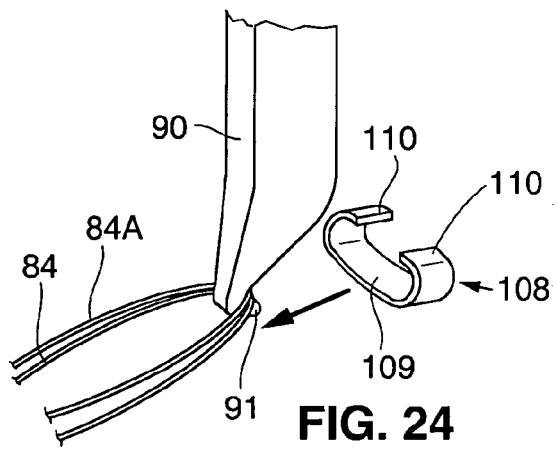
FIG. 24 is a perspective view of a detail of another implementation of the FIG. 21 apparatus, in which the apparatus functions to crimp another type of fastener clip around one set of aligned docking features.

In embodiments in which the fastener clip is held by the clip carriage with its crossbar facing down (as fastener clip 108 of FIG. 24 is oriented with its crossbar 109 facing down), the clip carriage should be configured to move the fastener clip initially downward (along a path outside the arms of forceps 90) and then to move the fastener clip horizontally inward (just under the distal end of the nearest arm of forceps 90) into position for crimping. With reference to FIG. 24 for example, the clip carriage (not shown in FIG. 24) would move clip 108 distally (vertically downward), and then horizontally inward until the clip's ends 110 straddle the central portions (84 and 84A) of aligned docking arms of rings 80 and 80A.

Figure 24A:
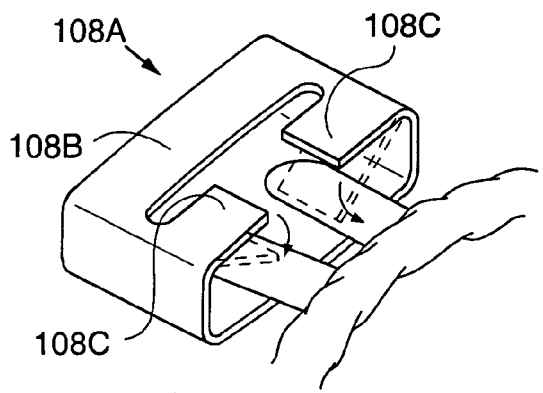
FIG. 24A is a perspective view of clip 108A which is an alternative embodiment of clip 108 of FIG. 24.

FIG. 24A shows a clip (clip 108A) which is an alternative embodiment of clip 108. Clip 108A has an extra crossbar 108B which aids in retention of aligned docking arms by the clip after the clip is crimped. Silicone or rubber can be coated under tabs 108C for greater compliance and improved retention of the aligned docking arms by the crimped clip.

FIG. 25 shows fastener clip 114, which is an alternative embodiment suitable for replacing clip 108 of FIG. 24. In use, fastener clip 114 of FIG. 25 is oriented with its crossbar 115 facing down, and is moved into position with first portions of aligned docking features (of two anastomosis rings) between its top end portion 116 and bottom end portion 116A, and with second portions of the aligned docking features between its top end portion 117 and bottom end portion 117A. Then, a hammer crimps end portions 116 and 116A together while crimping together end portions 117 and 117A. Crossbar (or "base") 115 is curved downward as shown, to provide extra room for clip 114 to clear the hook 91 of the forceps as clip 114 is moved into position (e.g., along the path followed by clip 108 as shown in FIG. 24). Bottom end portions 116A and 117A terminate at bent up tabs, which aid in retaining fastener 114 to the aligned anastomosis rings following crimping of fastener 114.

Numerous other variations on clips 100, 104, 108, 108B, and 114 are possible. Examples include fastener clip 118 (having spring arms) as shown in FIG. 25A, fastener clip 119 (having spring arms) as shown in FIGS. 25B and 25C in non-crimped and crimped configurations respectively, and the fastener clips shown in FIGS. 25D, 25E, 25F, 25G, and 25H. In use, the four extended edges 300 of the clip of FIGS. 25E and 25F would face the main bodies of the aligned rings (i.e., they would face the incisions or openings in the vessels being joined) so that the crimped clip can grip the rings very near to their main bodies (even though the bent end portions 301 of the clip, which are relatively far from the main bodies of the rings, are the clip portions that are actually crimped). In general, the action of crimping the inventive crimp clips becomes easier as the distance increases from the location of crimping to the main bodies of the anastomosis rings (around which they are crimped). The device which accomplishes the crimping takes up space, which is not always available very near to the main bodies of the anastomosis rings. In the clips of FIGS. 25G and 25H, appendages of the rubber (or silicone) lining protrude through small holes in the metal clip body as shown, to help attach the rubber (silicone) to the metal clip body. The rubber (silicone) can be bonded to the metal clip body or it can be formed to fit or molded around some or all of the edges of the metal clip body.

As described, the aligned anastomosis rings and forceps remain fixed (relative to the applier instrument) while the fastener clip is moved to achieve the desired relative position of fastener clip and anastomosis rings. In variations on the described embodiments, each fastener clip remains fixed (relative to the applier instrument) and the forceps (with the aligned anastomosis rings held thereby) is moved to achieve the desired relative position of fastener clips and anastomosis rings.

In another class of embodiments, the fastener clips are spring clips (preferably made of spring wire, but alternatively made of flat metal that is functional as a spring, or molded or machined plastics or similar material that is functional as a spring). In use, each spring clip is displaced from its relaxed configuration (either before it is brought into engagement with two aligned anastomosis rings, or during the act of engaging such rings). Then, the action of the aligned anastomosis rings on the spring clip allows the spring clip to relax (spring back) toward its relaxed configuration thereby wrapping itself around (or clamping itself over) aligned docking features of the aligned rings, to hold the aligned rings together by spring force. The spring clip is not crimped onto the aligned rings.

An example of such a spring clip is clip 120 of FIGS. 26-28. Clip 120 is made of stainless steel spring wire (e.g., 302V or 304V wire). It has spring portions 121 at its front (or "working") end. The spring portions 121 are connected by back portion 122. Each spring portion 121 includes front loop 123, loop 124, side loop 126, and free ("claw") end 125. Preloading of front loop 123 against loop 124 (and the particular shape of loop 126) reduces the expected mode of failure in which elements 123 and 125 do not have enough force to snap into place (with the docking features clamped between loops 123 and 124). The angle of ends 125 (with a small gap between them) improves the ability of ends 125 to catch (and snag) the docking arms. Tile low overall height of clip 120 makes the clip less likely to catch tissue and snap off.

A variety of alternative shapes for the spring clip are possible. All embodiments should include spring features that are placed over two aligned anastomosis rings to hold them together by spring force.

In use, each clip 120 is initially mounted in an implementation of the inventive clip carriage (e.g., one of the clip carriage implementations to be described with reference to FIGS. 32-35) with spring portions 121 in their relaxed configuration. Then, the clip carriage brings clip 120 into engagement with two aligned anastomosis rings (e.g., into engagement with their aligned docking arms), so that free ends 125 are displaced by the rings, thereby causing clip 120 to snag the docking arms. Loops 123 and 124 spread to receive the aligned docking arms between them as the clip continues to advance. After the central portions of the two aligned docking arms have entered the space between loops 123 and 124, loop 124 relaxes back toward loop 123 to clamp the two aligned docking arms together between loops 123 and 124 (so the arms are clamped together by spring force exerted thereon by loop 123, loop 124, and side loop 126 between loops 123 and 124). Preferably, when each ring is identical to ring 80 (of FIG. 18), and the central portions of the two aligned docking arms have entered the space between loops 123 and 124, side loops 126 engage (and are held in) notches 85 to more reliably retain clip 120 in a position in which it clamps together the aligned rings. In alternative embodiments, other appropriately shaped portions of the inventive spring clip engage (and are held in) other notches (or other appropriately shaped portions) of a pair of the inventive rings to retain the clip in place while it clamps the rings together.

Spring clip 130 of FIG. 30 is a variation on clip 120 of FIG. 126. Clip 130 is made of stainless steel spring wire, and has spring portions at its front (or "working") end which are connected by back loop 132. Each spring portion includes front loop 133, loop 134, side loop 136, and free ("claw") end 135. As shown in FIG. 30, spring clip 130 has been sprung around aligned docking arms 128 and 128A of two identical anastomosis rings 127 and 127A. Each of rings 127 and 127A is designed in accordance with the invention, and includes two symmetrically disposed, flexible docking arms (only one of which is shown in FIG. 30). In the position shown, the spring force that urges loop 134 toward loop 133 causes clip 130 to clamp docking arms 128 and 128A together. Side loops 136 are shaped to provide large spring force (at positions "C") between loops 133 and 134, and to give a mechanical limit to the amount by which loops 133 and 134 can separate from each other during installation of clip 130. Back loop 132 is shaped to allow clip 130 to compensate for the varying width between the opposite portions of each docking arm as the clip 130 advances into the position shown in FIG. 30. To install clip 130, the clip is advanced toward docking arms 128 and 128A until the docking arms displace claw ends 135, thereby causing clip 130 to snag the docking arms so that loops 134 and 133 will spread to receive the aligned docking arms between them as the clip continues to advance. After the central portions of the two aligned docking arms have entered the space between loops 133 and 134 (as shown in FIG. 30), loop 134 relaxes back toward loop 133 to clamp the two aligned docking arms together between loops 133 and 134. Loops 134 straddle front loops 133 to avoid causing the entire spring clip to cant at an angle to the plane of the aligned docking arms. FIG. 31 is an enlarged view of a portion of clip 130 in its relaxed configuration showing that loops 133 and 134 exert spring toward each other when an effort is made to separate them from each other.

Each of FIGS. 32 and 33 is a side view (partially cut away) of a detail of a variation on the FIG. 22 implementation of tool 95 of FIG. 21. Clip carriage 198 of FIGS. 32 and 33 replaces clip carriage 98 and hammer 99 of FIG. 22. Clip carriage 198 holds spring clip 130 of the type described with reference to FIG. 30. Back loop 132 of clip 130 is retained in notch 200 of carriage 198 by translatable pins 199 (shown in both FIGS. 33 and 34), so that clip 130's front end (including arms 135) are free to engage two aligned anastomosis rings. A ring alignment and clip applier apparatus that includes carriage 198 is configured to translate pins 199 up to release clip 130 after clip 130 has been clamped onto aligned docking features of the two aligned anastomosis rings (and preferably also to dispense a new clip to replace the released clip).

FIG. 35 is a side view (partially cut away) of a ring alignment and clip applier apparatus that includes carriage 198 (of FIG. 32), forceps 90 (shown in phantom view in FIG. 35), and an actuator for moving carriage 198 between extended and retracted positions (relative to forceps 90) such that an end hook 91 of forceps 90 (while the forceps are engaging and align together docking features of two anastomosis rings) follows the indicated path (relative to carriage 198) from the indicated starting point ("Start") to the indicated end point ("Finish") to move clip 130 into engagement with the aligned docking features (so that clip 130 clamps around the aligned docking features to hold the rings together in their aligned configuration). After forceps 90 has reached the indicated end point of its path, clip 130 has been clamped onto the aligned docking features of the rings, and the apparatus releases the clip from the carriage by retracting pins 199. By the time that hook 91 (more precisely, the innermost point on the upper surface of hook 91) reaches the "Midpoint" position, arms 135 of clip 130 have snagged the aligned docking features. After hook 91 has reached the indicated end point ("Finish") of its path, clip 130 has been clamped onto the aligned docking features of the rings. In the "Start" position, hook 91 extends considerably below (distally beyond) the distal end of the carriage clip 198 so the surgeon has good visibility of hook 91 during manual manipulation of forceps 90 to grab and align the rings.

FIG. 36 is a cut-away perspective view of an embodiment of the inventive tool (tool 220) for aligning two of the inventive anastomosis rings and crimping fastener clips around aligned docking features of the aligned rings. Tool 220 of FIG. 36 includes forceps 221 (which function in the same way as forceps 90 of FIGS. 19-21). Forceps 221 comprises two arms, with the distal end of each arm defining a hook 221A (corresponding to hook 91 of forceps 90), and a spring biased hinge that connects the proximal ends of the arms. The spring biased hinge exerts a biasing force which tends to separate the arms. Thus, in use the surgeon manually manipulates forceps 221 to grab and align together two anastomosis rings (including by manually pressing the arms together when desired to decrease the spacing between hooks 221A). As will be described, elements within tool 220 exert outward force on forceps 221 (tending to separate hooks 221A) at appropriate times during the operating cycle of the tool.

Tool 220 also includes two fastener clip carriers (carriages) 228, each of which holds fastener clips. Carriers 228 are translatable (relative to forceps 221 and handle 222) between the extended position shown in FIGS. 36 and 39, and the retracted position shown in FIG. 37. After the surgeon has manipulated forceps 221 to grab and align two rings (while the carriers 228 are in the retracted position), the surgeon holds handle 222 fixed and manually pushes activator 223 (in the distal direction toward the rings) to cause activator 223, pusher block 225, pusher block spring 230 (compressed between the proximal end of activator 223 and block 225), and the proximal end of mechanical linkage 224 (pivotably connected to block 225) to move distally relative to handle 222 (and forceps 221). In response, linkage 224 (which is coupled between block 225 and carriers 228, and includes distal portion 224A shown in FIG. 38) moves carriers 228 from the retracted position to the extended position (relative to handle 222 and forceps 221). Each arm of forceps 221 defines a carrier guide track 229. One of carriers 228 rides along each track 229. Since the proximal ends of tracks 229 are linear, carriers 228 (including their distal ends) initially translate along a linear path as they begin to move distally from their retracted position. But (since the distal ends of tracks 229 curve inward toward each other), as carriers 228 approach their extended positions, tracks 229 cause the distal ends of carriers 228 to depart from their initial linear paths to bring the clips (being carried at the distal ends of carriers 228) into the appropriate positions (relative to the aligned rings) to be crimped onto the aligned docking arms on both sides of the aligned rings. Linkage 224 allows carriers 228 to swing (and move laterally inward and outward) relative to forceps 221 during extension and retraction of carriers 228.

With reference again to FIGS. 36-39, tool 220 includes hammers 227 (one hammer 227 for each carrier 228). Each hammer 227 is pre-loaded to hold a fastener clip against a distal feature of the corresponding carrier 228. While the surgeon holds handle 222 fixed and manually pushes activator 223 (in the distal direction) relative to handle 222, linkage 224 moves carriers 228 and hammers 227 together as a unit in the distal direction. Spring 230 neither elongates nor compresses during this motion. Then, when carriers 228 have reached their extended position, tracks 229 prevent further distal motion of carriers 228 relative to handle 222, and further pushing force on activator 223 (in the distal direction) relative to handle 222 causes spring 230 to compress against block 225 (while block 225 remains stationary relative to handle 222), thereby causing activator 223 to engage and translate hammers 227 distally relative to carriers 228, handle 222, block 225, and forceps 221 (and causing activator 223 to compress activator spring 226 against the forceps 221). This distal motion of hammers 227 relative to carriers 228 crimps the fastener clips onto the aligned anastomosis rings (being held by forceps 221). Specifically, the advancing hammers 227 press the fastener clips against distal features of carriers 228 (which distal features are being held fixed), while the fastener clips enclose aligned docking features (typically docking arms) of the anastomosis rings, thus deforming the fastener clips and causing them to crimp around the docking features.

The compression of spring 226 during the crimping operation causes spring 226 to exert increased opening force on forceps 221 during the crimping (force which tends to further separate hooks 221A from each other). This increased opening force counters the closing force exerted by carriers 228 on forceps 221 to ensure that the forceps remain fully opened to keep the anastomosis rings in place.

After the fastener clips have been crimped around the docking features of the aligned rings, the user releases activator 223. In response, springs 226 and 230 elongate (back to their original state), thereby pushing activator 223, block 225, linkage 224, carriers 228 and hammers 227 back to their original (retracted) state.

In variations on the embodiment of FIGS. 36-39, the inventive ring alignment and clip fastening tool includes forceps, carriers that hold fastener clips, and a mechanical assembly for causing relative motion of the fastener clips and the forceps along a path. The path can be determined by a guide track in the forceps or a separate device (such as a handle or other stationary element), or by other means. The forceps are positioned relative to features of the anastomosis rings to be aligned and fastened together (e.g., the forceps hook onto the rings), thus locating the carriers with respect to the rings. In some such variations, the tool is one-sided in the sense that it has only one hammer and one fastener clip carrier. In both one-sided and two-sided embodiments, tie clip carrier (or carriers) can carry clips adapted to be crimped on the rings (and the tool can include a hammer for crimping the clips), or the tool does not include a hammer and each clip carrier carries a spring clip (e.g., spring clip 120 of FIG. 26, or clip 130 of FIGS. 30 and 35) that is configured to clamp itself onto aligned features of the rings.

FIG. 40 shows one of the inventive anastomosis rings (ring 330) installed in an orifice in a coronary artery, and another of the inventive anastomosis rings (ring 331) installed in an orifice in a graft vessel. The docking arms of ring 331 are held in notches at the ends of the arms of a forceps, and the forceps is being moved toward ring 330, in order to roughly align the two rings.

FIG. 41 shows rings 331 and 330 (of FIG. 40) after they have been brought into alignment with each other (by being held by a single forceps).

FIG. 42 is a perspective view of an embodiment of the inventive tool (tool 399) for installing an anastomosis ring (above-described anastomosis ring 80) in an incision (or other orifice) in a vessel or other organ. FIG. 43 is a perspective view of the distal end portion of tool 399 of FIG. 42. Tool 399 can be implemented to be disposable or reusable.

Anastomosis ring 80 is mounted at distal end 59 of tool 399, with anvil 412 extending distally beyond ring 80. In use, anvil 412 is inserted into a small incision in a vessel (e.g., a small arteriotomy). Then, the distal portion 59 of tool 399 is lowered toward the anvil to receive anvil stem 412A and to engage stem 412A with anvil retraction link 406A. (In alternative embodiments, a separate mechanism, such as the anvil retraction and lock subassembly in rear assembly 501 of tool 499 of FIG. 48, is provided to releasably lock anvil stem 412A to the tool and advance the anvil at appropriate times). Then, "anvil retract" trigger 406 is pulled in the proximal direction (relative to handle 401) to retract anvil 412 relative to tool 399 (by action of link 406 on anvil stem 412A).

Then, firing trigger 400 is pulled (relative to handle 401) to "fire" the tool 399. In response to the pulling of trigger 400, straight tines of ring 80 are pushed through the tissue surrounding the incision (with the central ring portion of ring 80 positioned around the incision), and then tool pushes the tines against the anvil to curl the tines against the anvil. The action of curling the tines inverts the tissue near the orifice edges (by everting the tissue) to expose the inside surface of the vessel (the intima), so that such exposed intima can be joined to tissue of another vessel or organ.

More specifically, the pulling of firing trigger 400 causes link portion 430 of trigger 400 (shown in FIG. 44) to pull each cam plate 408 downward. Each cam plate defines cam tracks 409, 410, and 411. As each plate 408 moves downward relative to handle 401, various elements in tool 399 (engaged with tracks 409, 410, and 411) respond to motion of tracks 409, 410, and 411 to complete a timed, programmed, forceful action at distal end 59. This action accomplishes the pushing of straight tines of ring 80 into engagement with the tissue surrounding the incision into engagement with anvil 412, followed by translation of incision lengthening blades 426 distally through the central orifice of ring 80 (into engagement with the vessel such that blades 426 are aligned with the incision) until blades 426 cut the tissue to extend the incision (thereby forming an extended incision of precisely known overall length, which is slightly shorter than the length of ring 80's central orifice). Then, blades 426 are retracted out of engagement with the vessel and ring 80, a driver (comprising "primary" element 424 and ring "backer" element 422 fixedly attached to element 424) moves distally into engagement with ring 80, so as to push ring 80 distally against the anvil 412. As the driver pushes ring 80 against anvil 412, the tines of ring 80 curl against the anvil.

The action of curling the tines inverts the tissue near the incision edges to expose the inside surface of the vessel (so that the exposed inside surface can be joined to tissue of another vessel).

Specifically, as each plate 408 moves downward relative to handle 401, cam follower 443 is driven distally by track 410, and cam follower 443 in turn pushes tube 442 (and cutter base 428 at the distal end of tube 442) distally to drive cutting blades 426 distally into engagement with the tissue (to lengthen the preliminary incision, as described). Then, as plate 408 continues to move downward, track 410 pulls cam follower 443, tube 442, base 428, and blades 426 proximally (to retract blades 426 away from ring 80 and the incised tissue).

As plate 408 moves downward relative to handle 401 (at the time "cutting" cam follower 443 begins to retract in the proximal direction), "primary" cam follower 445 is driven distally by track 411, and cam follower 445 in turn pushes tube 444, primary element 424 (fixedly attached to the distal end of tube 444), and ring backer element 422 (fixedly attached to element 424) moves distally until element 422 engages ring 80 and pushes ring 80 distally against the anvil 412. As the driver (comprising element 445, 444, 424, and 422) pushes ring 80 against anvil 412, the tines of ring 80 curl against the anvil. After the driver curls the tines of ring 80, the central vertical portion of cam track 411 leaves cam follower 445 in its fully extended position (while cam track 410 causes cam follower 441 to control spreading of the ring 80). Then, cam track 411 pulls cam follower 445 in the proximal direction, thereby causing elements 444, 424, and 422 to retract in the proximal direction (out of engagement with ring 80).

While the central (vertical) portion of cam track 411 leaves cam follower 445 in its fully extended position (and while cam track 410 pulls cam follower 443 in the proximal direction), cam track 409 pushes cam follower 441 in the distal direction. Cam follower 441 in turn pushes tube 440, spreading base 414 (fixedly connected to the distal end of tube 440), and four spreading tubes 420 (fixedly connected to base 414) distally. Fixed outer tube 404 encloses concentric (independently translatable) tubes 440, 442, and 444.

When cam track 411 has caused primary element 424 to advance distally, the proximal ends of pins 413 have advanced distally to extend through docking holes 85 of ring 80. In this position, the distal ends of pins 413 can exert lateral force on ring 80 (to spread or narrow the orifice through the central ring portion of ring 80). Pins 413 slide (distally or proximally) in spreading tubes 420. Tubes 420 are rigidly attached at one end to spreading base 414, and tubes 420 extend slidably through holes in cutting base 428. The distal end of each tube 420 terminates at a spreading cam element 415. Cam track 409 drives base 414 (and thus tubes 420) in the distal direction at the same time cam track 411 holds fixed the assembly comprising elements 445, 444, and 424, thus causing cam elements 415 (sometimes referred to as cam "beads") to engage and ride against a ramped proximal surface of element 424 (ramped surface 424A of element 424, best shown in FIG. 47A). Cam elements 415 spread away from each other as they engage and ride against the ramped proximal surface of element 424. Tubes 420 and pins 413 are flexible. As cam elements 415 spread apart from each other, they spread the distal ends of pins 413 away from each other, thereby causing the distal ends of pins 413 to spread the orifice through the central ring portion of ring 80 (which in turn widens the orifice in the vessel at the incision site where ring 80 is installed). The final, vertical segment of cam track 409 releases the tension on the spreader assembly (so that the relative spacing of the distal ends of pins 413 does not change following the spreading operation).

Pin link portion 402 of base 418 is coupled to tube 444, and thus base 418 moves (or remains fixed) together as a unit with primary element 424 (fixedly attached to the distal end of tube 444). The proximal ends of pins 413 are attached to base 418. Thus the distal ends of pins 413 move distally into engagement with ring 80 when cam 411 causes primary element 424 to move distally relative to ring 80 (to curl the tines of ring 80).

After the spreading operation, in completion of an operating cycle of tool 399 in response to a single pull on trigger 400), a mechanism (not shown) within tool 399 releases anvil stem 412A. This allows the surgeon to remove tool 399 (minus anvil 412 and stem 412A) from the vessel environment, while stem 412A and anvil 412 remain behind (with ring 80 which has been installed in the vessel and spread open by the desired amount). The surgeon then manipulates stem 412A to remove anvil 412 from the vessel through the spread-open ring 80.

FIG. 46 is a side elevational view of cam plate 408 of tool 399 of FIG. 42, showing cam tracks 409, 410, and 411.

Use of tool 399 or 499 reduces the ischemic time to complete a bypass, and also reduces overall operating room time required to complete various surgical procedures (which include one or more anastomosis steps). The small diameter of tool 399's distal end is a benefit to the surgeon, to allow the surgeon to visualize insertion and removal of the anvil. Tool 399 automates a large number of motions which the surgeon would otherwise need to perform manually.

In alternative embodiments, the inventive tool for installing an anastomosis ring in an incision includes a cam element which defines cam tracks, but is not a flat cam plate (such as plate 408). The cam element (which could be cylindrical or otherwise curved) is moved relative to other portions of the tool to cause various elements of the tool (engaged with the cam tracks) to respond to motion of the cam tracks by completing a timed, programmed, forceful action at the tool's distal end.

In alternative embodiments, the inventive tool for installing an anastomosis ring in an incision includes means for reloading a new anastomosis ring (following each installation) by transferring the new ring from a disposable, cartridge, or means for reloading a new anastomosis ring and a new anvil (following each installation).

FIG. 48 is a perspective view of ring installation (and incision lengthening) tool 499, which is a variation on tool 399 of FIGS. 42-47. Tool 499 differs from tool 399 in that it has a rear assembly 501 including an anvil lock mechanism which can be actuated to lock an anvil stem (e.g., stem 412A) with an anvil retraction link (which is also included within rear assembly 501) or to release the anvil stem from the anvil retraction link.

We will describe the anvil lock and release mechanism of tool 499 with reference to FIGS. 48-54. Tool 499 is identical to above-described tool 399, except in the respects described below.

The anvil assembly comprises anvil 412 and anvil stem 412A. As shown in FIG. 49, distal portion 412F of stem 412A defines two flat alignment faces and two grooves (for aligning stem 412A relative to cutting blades 426 and the other adjacent elements of the tool). Proximal end 412D of stem 412A is tapered for insertion into assembly 501. Protruding features 412C are provided for engaging the lock mechanism within assembly 501. As best shown in FIG. 50, the proximal face of anvil 412 has tine-forming pockets 412E (which are positioned to receive the tines of the inventive anastomosis ring) and cutting pad 412B (preferably made of elastomeric or plastic material) which the cutting blades strike during the incision lengthening step.

In use, anvil 412 is inserted into a small incision in a vessel (e.g., a small arteriotomy). Then, anvil retraction collet 450 (at the distal portion of tool 499) is lowered to receive anvil stem 412A (as shown in FIG. 49). Collet 450 protrudes distally from locking collar 451 of assembly 501 (as shown in FIGS. 49 and 52) but collet 450 can retract in the proximal direction into collar 451 of assembly 501. Anvil shaft 412B is inserted into engagement with collet 450 until its distal end 412D reaches a stop (in the position shown in FIG. 52), so that the assembly comprising shaft 412A and collet 450 engages retraction shaft 457.

Tool 499 includes an anvil traction trigger, which can be identical to trigger 406 of FIG. 42 but which is coupled to retraction shaft 457. Retraction shaft 457 has a protrusion 457A (shown in phantom view in FIG. 53) that is shaped for engaging stepped lock 454. Lock 454 (shown in FIG. 54) is biased against shaft 457 by leaf spring 500 (shown in FIGS. 48 and 53). The user manually displaces spring 500 away from lock 454 when it is desired to release anvil stem 412A from assembly 501. In alternative embodiments of the invention, a mechanism is provided for conveniently displacing spring 500 (or for controlling an element that performs a function equivalent to that of spring 50).

When anvil shaft 412B and collet 450 are in the position shown in FIG. 52, the surgeon pulls the anvil retraction trigger in the proximal direction, thus pulling collet 450, shaft 457, and anvil stem 412A together as a unit (in the proximal direction) relative to lock 454 until the protrusion of shaft 457 engages lock 454. The protrusion overcomes the biasing force exerted by spring 500 to displace lock 454 away from the main body of shaft 457. Then, when the protrusion has passed lock 454, lock 454 relaxes back into engagement with the main body of shaft 457, thereby locking anvil stem 412A to assembly 501.

A spring 456 (shown in phantom view in FIG. 53) is coupled between protrusion 457A and the proximal end of assembly 501. While shaft 457A retracts in the proximal direction relative to lock 454, spring 456 is compressed. Then, when the user displaces leaf spring 500 away from lock 454, spring 456 relaxes back to its elongated state, thereby pushing protrusion 457A (and shaft 457, collet 450, and anvil stem 412A) distally, to release shaft 412 from lock 454.

Coupling element 459 (omitted for clarity from FIG. 51, but shown in FIG. 53) fits around collar 451, such that element 459 is free to slide longitudinally relative to collar 451. Proximal end 459A of element 459 is attached to the distal end of pin 452. When anvil stem 412A is locked to assembly 501, the proximal end of pin 452 (which extends within body 501A of assembly 501) faces lock 454. Pin 452 (shown in FIG. 53), leaf spring 500 (shown in FIG. 53), and portions of body 501A, are omitted from FIG. 54, so that FIG. 54 shows groove 453 in element 451A and grooves 453A and 453B (defined by main body 501A of assembly 501). Grooves 453A and 453I are aligned with groove 453. Pin 452 fits in the aligned grooves 453, 453A, and 453B, with the proximal end of pin 452 facing lock 454.

Distal end 459B of element 459 is coupled to the tool's "cutting" cam follower 443 (shown in FIG. 44). Thus, when cam follower 443 retracts in the proximal direction, element 459 (and pin 452) retract together as a unit relative to collar 451 and body 501A of assembly 501. Tool 499 is configured so that when cam follower 453 has retracted element 459 and pin 452 sufficiently far in the proximal direction so that the proximal end of pin 452 engages ramped surface 455 of lock 454, the tool causes anvil 412 to advance a short distance distally away from the anastomosis ring. Specifically, when pin 452 has retracted into engagement with surface 455 and continues to retract proximally, the action of pin 452 on surface 455 moves lock 454 downward (perpendicularly to the distal direction) so as to reduce the locking force exerted by lock 454 on the anvil stem assembly. As this occurs, the biasing distal force exerted by spring 456 pushes shaft 457 (and thus anvil stem 412A) in the distal direction, thereby advancing anvil 412 slightly (e.g., by 0.020 inch) in the distal direction away from the installed anastomosis ring. The tool's cam tracks (409, 410, and 411) are shaped so as to cause this advancement of anvil 412 (distally away from the anastomosis ring) to occur just after the tines of the ring have been curled against the anvil but before the ring is spread by the tool's ring spreading assembly (i.e., the assembly comprising elements 413, 414, 415, and 420).

The tool's cam tracks (409, 410, and 411) are shaped so as to automatically release the anvil assembly from the rest of the tool following the ring spreading operation. Specifically, after the ring spreading operation, cam follower 453 has retracted element 459 and pin 452 sufficiently far in the proximal direction so that the proximal end of pin 452 engages the second ramped surface (surface 458) of lock 454. When pin 452 has retracted into engagement with surface 458 and continues to retract (in response to further retraction of cam follower 453), the action of pin 452 on surface 458 moves lock 454 downward (perpendicularly to the distal direction) sufficiently far to decouple lock 454 from the anvil assembly (thus terminating the locking force exerted by lock 454 on the anvil assembly). As this occurs, the biasing distal force exerted by spring 456 pushes shaft 457 (and thus anvil stem 412A) in the distal direction, thereby advancing anvil 412 slightly in the distal direction until spring 456 reaches its fully-extended relaxed state and the anvil assembly is decoupled from the rest of the tool. With the anvil assembly decoupled from lock 454 (and the rest of the tool), the tool (minus anvil stem 412A and anvil 412) is removed from the anastomosis site. The surgeon then manipulates the anvil stern to remove the anvil (through the installed anastomosis ring) from the anastomosis site in the manner described above.

In the operation of the ring installation tools 399 and 499 shown in FIGS. 42-54, the spreading pins 413 not only function to spread or narrow the orifice through the central portion of the ring, but also serve the function of holding and retaining the ring in position on the tool prior to installation. This occurs through one or both of friction between the pins 413 and openings in the anastomosis ring (e.g. the edges defining holes 53) through which they pass, and a slight outward pivoting of the pins. A feature of the installation tools described is that the pins 413 are well aligned and coordinated in operation so as to move the ring relatively uniformly so that the tines all strike the anvil at the proper (predetermined) points.

Another means of retaining an anastomosis ring in position on an installation tool is shown in FIG. 55. FIG. 55 assumes that the installation tool has an outer tube 404 such as that shown in FIG. 42. Here the ring 80 is of an embodiment such as that shown in FIG. 18, having docking members (flexible docking arms 84 of FIG. 18). A tubular-shaped compliant retaining collar 550 formed of rubber or another suitable elastic material is fitted over the ring 80 to hold it in place at the distal end 59 of tube 404. Docking arms 84 are bent upwards while the ring is held in place by collar 550, then return to their original position when the ring advances out of the tool and is installed at the anastomosis site by the action of spreading pins 413 as described above. Retaining collar 550 remains on the tool after installation of the ring and is removed after use. Ring 80 has a malleable ring portion from which flexible docking arms 84 extend, and defines pin-receiving openings. The installation tool includes (within tube 404) a set of spreading pins 413 (shown in phantom view in FIG. 55) and a pin driving assembly 413A. Assembly 413A is configured to position pins 413 so that they extend through the pin-receiving openings defined by ring 80, to then move the pins away from each other so as to spread open the malleable ring portion, and to then retract pins 413 away from the ring (after the ring portion has been spread).

Still another means of retaining an anastomosis ring in position on an installation tool is shown in FIGS. 56-57., and employs a wireform. FIG. 56 is a cross-sectional view of the distal end 59 of a ring installation tool using this embodiment. An anastomosis ring 80 is held in place at the top of (i.e. distal to) primary element 560 by wireform 565. The wireform has a generally circular base 568 and two or more arms 570 extending out from the base. Arms 570 engage the docking arms 84 (not shown) of ring 80. The base of wireform 565 is inserted in a generally circular slot 575 in the circumference of the base 580 of backer 585. Spreading pins 413 extend through holes or slots in backer 585, then through spreading tubes 590 (which correspond functionally to above-described spreading tubes 420 and cam elements 415) and ultimately through the holes 83 (not shown) in ring 80, as described previously.

When the trigger of the installation tool is pulled, the action of the mechanisms described above causes spreading pins 413 to move distally through tubes 590 and holes 83 in ring 80, while tubes 590 (and thus pins 413) move radially out and away from each other (to exert spreading force on ring 80). This action moves ring 80 away from the primary element 560 and disengages it from the arms 570 of wireform 565, installing the ring at the anastomosis site, as described above. Cam action of the tool (as in tools 399 and 499, described above), then causes the spreading pins to retract.

FIG. 57 shows an alternate construction of the distal end of tile ring installation tool. Here, the ring 80 is positioned and held on primary element 560 with a wireform (not shown) inserted in a slot in the circumference of tile backer 585, as in FIG. 56. The arms of the wireform are retained in place in slots 598 of backer 585. Spreading tubes 590 fit in slots 595 in the base of backer 585, which is preferably beveled. Spreading pins 413 move through the spreading tubes (and the spreading tubes move radially outward away from each other) as in the FIG. 56 embodiment.

Other means of retaining the ring in position at the distal end of an installation tool may be employed, for instance hooks appropriately situated so as to engage the docking arms of a ring.

In another aspect of the invention, instead of using a pair of incision-lengthening cutting blades (such as blades 426 in FIG. 45), a single cutting blade with two cutting edges may be employed. Such a blade is shown in FIG. 58. It has a generally Z-shaped cross-section and is prepared from a single, generally rectangular, sheet or plate of an appropriate metal, for example, surgical steel.

The blade, generally indicated as 600, has an upper rectangular shaped portion 602 and two generally rectangular shaped Cutting blades 604, 606 with an open space 608 between them. In operation this Cutting blade element, as is described above, is translated distally through the central orifice of the anastomosis ring (Such that the cutting blades 604, 606 are aligned with the incision in which the ring is to be installed) until the blades cut the tissue to extend the incision (thereby forming an extended incision of a precisely known overall length, which is slightly shorter than the length of the central orifice of the ring). Cutting blade 600 is then retracted. Cutting blade 600 is advanced and retracted by action of cam followers on a cutting blade base, as in the above-described embodiment of FIG. 45.

The cutting blade 600 is manufactured by cutting an appropriately sized slot 608 into a flat rectangular-shaped metal plate. The slot contains relief notches 610, 612 on either side. After the slot and notches are cut into the plate, the plate is bent twice, once at the relief notches, and once above them to provide the generally Z-shaped cutting blade 600.

FIGS. 59-61 depict an embodiment of the invention in which a compliant (e.g. elastomeric) member is utilized in combination with a backer (which is typically but not necessarily formed of a similar material) to retain an anastomosis ring in position in the installation tool prior to use.

FIG. 59 is a perspective view of this combination, as seen from behind the backer. As shown in FIG. 59, backer 620 is generally disc-shaped with a bowtie- or figure-eight-shaped cutout 624 through its center. Only part of the bowtie or figure eight cutout extends completely through the backer; a portion 626 at each end of the cutout is left to serve as a ledge or resting place for compliant member 622.

Compliant member 622 is shown in detail in FIG. 60. It has a central cutout 622A which corresponds generally to the shape of the ring driver of the installation tool (e.g. primary element 424 of FIG. 45) and to the central orifice of the ring (e.g. ring 80), and also includes holes 628 through which spreading pin extensions 413A extend. The proximal ends of the extensions 413A can be fitted onto spreading pins 413 of FIG. 59. Member 622 is placed on the ledges 626 of backer 620 and spreading pin extensions 413A are inserted through holes 628. Then as shown in FIG. 59, ring 80 is installed with the tines facing distally (downward in FIG. 59). As described hereinbelow "ring 80" and its parts refers to an embodiment of a ring as depicted in FIG. 18. However, any embodiment of the inventive ring may be used with FIG. 59 embodiment of the invention.

FIG. 61 is the reverse view of FIG. 59. It shows ring 80 with spreading pin extensions 413A passed through the aligned holes through ledge 626, hole 628, and holes in the ring (e.g. holes 83 of FIG. 18). As can be seen in FIG. 61, backer 620 has, on the distal side, a distally-protruding structure 620A. The central ring-shaped portion of ring 80 sits within a recess defined by this structure such that tines 81 are protected by the structure from damage while the ring is retained by the installation tool. The spreading pin extensions 413A (which extend through elements 620 and 622, and through holes in the ring) hold the ring in place primarily by friction. Pin extensions 413A are advanced, retracted, and spread by the force exerted thereon by pins 413 of the reusable portion of the installation tool.

Note that the combination assembly of ring, backer 620, compliant member 622, and spreading pin extensions 413A may be produced as a separate subassembly and packaged and dispensed for removable mounting at the distal end of a ring installation tool. The entire assembly can be removed from a reusable portion of an installation tool and discarded following a single ring installation. Alternatively, the spreading pin extensions can be omitted, and instead reusable spreading pins (e.g. pins 413) inserted through holes 628 to attach the single-use assembly to a reusable portion of an installation tool. Following installation of a ring, the spreading pins can be sterilized and re-used.

Another embodiment of this invention relates to loading devices for loading a ring installation tool with anastomosis rings and optionally with anvils.

One such loading device is shown in FIGS. 62 to 64. This loading device is comprised of a base and block generally indicated as 640 having a recess or cavity 642 in which are located the anastomosis ring 80 and optionally an anvil 60 having an anvil stem 61. Ring 80 is supported on loading pins 644 which protrude from base 640. The pins are situated so as to fit within holes 83 of ring 80 and the number of pins corresponds to the number of such holes. As indicated generally in FIG. 63, loading pins 644 are spring-mounted (on springs 644A). Ring 80 is placed on the pins 644 with tines 81 pointed downward due to the elevation of the loading pins from the bottom of loading base 640. The tines are not in contact with the base. The ring 80 and optionally anvil 60 are loaded via opening 656 onto the distal end of a barrel 650, which may be the distal end of anastomosis installation device such as those illustrated in FIGS. 42 and 48. For proper alignment with the ring, the distal end of barrel 650 has a key 652 which fits into a slot 654 located in the upper portion of the loading base 640 so as to properly align the distal end of the barrel with the ring and/or anvil.

By using loading device the anastomosis installation tool 650 is lowered onto the loading base 640 using key 652 and slot 654 for alignment. If an anvil is to be loaded, the installation tool or barrel is lowered over the top of stem 61 so that the stem becomes inserted into the barrel or tool through distal opening 656: As the device 650 is lowered onto the ring 80 (as shown in FIG. 64), spreading pins (such as above-described pins 413) become introduced into the holes 83 of the ring, displacing loading pins 644 downwardly as they enter holes 83. The spreading pins engage ring 80 so as to hold it in place at the distal end of element 650 and the anvil stem 61 is engaged by appropriate mechanisms contained within element 650 (for example, those shown in FIG. 49). The ring 80 and anvil 60 are then withdrawn from the loading device 640 and the installation tool is ready for use.

Another loading device is shown in FIGS. 65 to 67. In this device the anastomosis ring is held above the surface of a loading base by loading pins 664. The device comprises a loading base 660 having loading pins 664 contained within loading pin tubes 662. Anastomosis ring 80 is supported on the loading pins 664 by insertion of the pins 664 through holes in the ring. Mounting of the ring is done so that the ring's tines 81 extend downwardly. Below the ring, a base 660 has a central recess 666. An anvil (not shown) may be contained within this recess opening, as in the loading device shown in FIGS. 62-64.

As shown in FIG. 66, the anastomosis installation tool 650 is lowered onto the loading device containing the ring. For alignment purposes, the device or barrel may be equipped with a key and a slot similarly to the device shown in FIGS. 62-64. In any event, since the ring is elevated above the recess 666 of loading block 660 the alignment of the ring and anvil with the installation tool can be visually observed and adjusted as necessary. As with the device previously described, spreading pins 413 of the installation tool are lowered onto loading pins 664, thereby displacing pins 664 downward in tubes 662 (pins 664 can be spring loaded within tubes 662) so as to engage ring 80. Likewise, similarly to the device previously described, if an anvil is to be loaded with the ring, it is engaged by a mechanism located within the installation tool. The ring (and optionally the anvil) is then lifted off the loading pins 664 and tubes 662 and the installation tool is utilized to install the ring at an anastomosis site.

It is understood that while certain forms of the present invention have been illustrated and described herein, the invention is not to be limited to the specific forms or arrangements of parts described and shown or the specific methods described.

What is claimed is:

1. An apparatus for preparing a first organ having an orifice for anastomosis with a second organ, by installing at the orifice a ring consisting of a malleable ring portion, sized to extend around the orifice, and docking members and malleable tines extending out from the ring portion, said apparatus comprising:

a ring-mounting assembly configured to releasably mount the ring;
an anvil extending transversely across a distal end of an anvil stem;
an anvil mounting assembly configured to releasably mount the anvil in such a position that the anvil can be advanced into the first organ; and
a cam-driven assembly comprising a cam element having cam tracks and configured to advance the anvil mounting assembly toward the anvil, after the anvil has been positioned in the first organ and the ring has been positioned so that the ring portion extends around the orifice, to cause tips of the tines to pierce tissue of the first organ around the orifice and then to advance into engagement with the anvil, and to then continue to advance the ring toward the anvil thereby causing the tines to curl against the anvil after piercing the tissue around the orifice so as to evert said tissue around the orifice.

2. The apparatus of claim 1, wherein the apparatus also includes a housing in which the cam-driven assembly is mounted, and wherein said cam-driven assembly includes:
a trigger assembly; and
a set of cam followers;
wherein the cam followers are engaged with the cam tracks and the cam element is coupled to the trigger assembly such that actuation of the trigger assembly moves the cam element relative to the cam follower to cause said cam followers to move relative to the housing; and
elements coupled between the cam followers and the ring-mounting assembly, wherein the elements are configured to respond to motion of the cam followers to complete timed, programmed, forceful actions of the ring.

3. The apparatus of claim 2, wherein the cam element is a plate having openings that extend therethrough, said openings defining the cam tracks.

4. The apparatus of claim 2, wherein said elements include spreading pins having free ends that are configured to be releasably engaged with said ring, and wherein the cam-driven assembly is configured to respond to motion of at least one of the cam followers by causing the spreading pins to advance the ring toward the anvil, moving at least one of the spreading pins away from at least one other of the spreading pins to spread the ring portion, and then causing the spreading pins to retract away from the ring and the anvil.

5. The apparatus of claim 4, wherein the first organ is a blood vessel having a sidewall, the orifice is an incision in the sidewall, and the cam-driven assembly includes:
at least one incision-lengthening blade, wherein the cam-driven assembly is configured to respond to motion of at least one other one of the cam followers by causing the elements to advance the incision-lengthening blade distally into engagement with the sidewall to extend the incision, thereby forming an extended incision of precisely known overall length, at a tine after the tips of the tines have pierced said tissue but before the tines have been advanced into engagement with the anvil.

6. The apparatus of claim 4, wherein the elements are coupled between the cam followers and the ring-mounting assembly and between the cam followers and the anvil mounting assembly, the elements are configured to respond to motion of the cam followers to complete timed, programmed, forceful actions of the anvil and the ring, and the cam-driven assembly is configured to respond to motion of at least one other one of the cam followers by causing the elements to advance the anvil distally away from the ring after the tines of said ring have been curled against the anvil but before the ring portion has been spread by the spreading pins.

7. The apparatus of claim 6, wherein the cam-driven assembly is configured to respond to motion of said at least one other one of the cam followers by automatically releasing the anvil assembly from the apparatus after the spreading pins have spread the ring portion.

8. The apparatus of claim 6, wherein the first organ is a blood vessel having a sidewall, the orifice is an incision in the sidewall, and the cam-driven assembly includes:
at least one incision-lengthening blade, wherein the cam-driven assembly is configured to respond to motion of at least one other one-of the cam followers by causing the elements to advance the incision-lengthening blade distally into engagement with the sidewall to extend the incision, thereby forming an extended incision of precisely known overall length, at a time after the tips of the tines have pierced said tissue but before the tines have been advanced into engagement with the anvil.

9. The apparatus of claim 8, wherein the cam element defines a first one of the cam tracks which controls advancement and retraction of the spreading pins, a second one of the cam tracks which controls relative spacing between said at least one of the spreading pins away and said at least one other of the spreading pins, and a third one of the cam tracks which controls advancement and retraction of the incision-lengthening blade.

10. The apparatus of claim 1, wherein the anvil mounting assembly releasably holds the stem such that the anvil is positioned to be advanced into the first organ.

11. The apparatus of claim 10, wherein the ring has a first number of tines, and the anvil has a surface which defines a first number of recesses, each of the recesses being shaped and positioned to receive and curl a different one of the tines when said tines are advanced into engagement with said anvil.

12. An apparatus for preparing a first organ having an orifice for anastomosis with a second organ, by installing at the orifice a ring consisting of a malleable ring portion, sized to extend around the orifice, and docking members and malleable tines extending out from the ring portion, said apparatus comprising:
an anvil extending transversely across a distal end of an anvil stem;
a ring-mounting assembly configured to releasably mount the ring;
an anvil mounting assembly configured to releasably mount the anvil in such a position that the anvil can be advanced into the first organ; and
a cam-driven assembly including cam tracks and configured to advance the anvil mounting assembly toward the anvil, after the anvil has been positioned in the first organ and the ring has been positioned so that the ring portion extends around the orifice, to cause tips of the tines to pierce tissue of the first organ around the orifice and then to advance into engagement with the anvil, to then continue to advance the ring toward the anvil thereby causing the tines to curl against the anvil after piercing the tissue around the orifice so as to evert said tissue around the orifice, and to advance the anvil distally away from the ring after the tines of said ring have been curled against the anvil, before the ring portion is spread.

13. An apparatus for preparing a first organ having an orifice for anastomosis with a second organ, by installing at the orifice a ring consisting of a malleable ring portion, sized to extend around the orifice, and docking members and malleable tines extending out from the ring portion, said apparatus comprising:
a ring-mounting assembly configured to releasably mount the ring;

an anvil mounting assembly configured to releasably mount an anvil in such a position that the anvil can be advanced into the first organ; and a cam-driven assembly configured to advance the anvil mounting assembly toward the anvil, after the anvil has been positioned in the first organ and the ring has been positioned so that the ring portion extends around the orifice, to cause tips of the tines to pierce tissue of the first organ around the orifice and then to advance into engagement with the anvil, and to then continue to advance the ring toward the anvil thereby causing the tines to curl against the anvil after piercing the tissue around the orifice so as to evert said tissue around the orifice; wherein the apparatus also includes a housing in which the cam-driven assembly is mounted, and wherein said cam-driven assembly includes: a trigger assembly; a set of cam followers; a cam element defining cam tracks, wherein the cam followers are engaged with the cam tracks and the cam element is coupled to the trigger assembly such that actuation of the trigger assembly moves the cam element relative to the cam follower to cause said cam followers to move relative to the housing; and elements coupled between the cam followers and the ring-mounting assembly, wherein the elements are configured to respond to motion of the cam followers to complete timed, programmed, forceful actions of the ring; wherein said elements include spreading pins having free ends that are configured to be releasably engaged with said ring, and wherein the cam-driven assembly is configured to respond to motion of at least one of the cam followers by causing the spreading pins to advance the ring toward the anvil, moving at least one of the spreading pins away from at least one other of the spreading pins to spread the ring portion, and then causing the spreading pins to retract away from the ring and the anvil.

* * * * *